US007419995B2

(12) United States Patent  
Crew et al.

(10) Patent No.: US 7,419,995 B2
(45) Date of Patent: Sep. 2, 2008

(54) N-SUBSTITUTED BENZIMIDAZOYL C-KIT INHIBITORS AND COMBINATORIAL BENZIMIDAZOLE LIBRARY

(75) Inventors: Andrew Philip Crew, Farmingdale, NY (US); Matthew Cox, Farmingdale, NY (US); Radoslaw Laufer, Farmingdale, NY (US); Neil Anthony Pegg, Oxford (GB); Colin Peter Sambrook Smith, Oxford (GB); Yingchuan Sun, Farmingdale, NY (US); Robin David Wilkes, Oxford (GB); Jonathan Williams, Oxford (GB)

(73) Assignee: OSI Pharmaceuticals, Inc., Melville, NY (US)

( * ) Notice: Subject to any disclaimer, the term of this patent is extended or adjusted under 35 U.S.C. 154(b) by 374 days.

(21) Appl. No.: 11/290,028

(22) Filed: Nov. 30, 2005

(65) Prior Publication Data

US 2006/0116402 A1 Jun. 1, 2006

Related U.S. Application Data

(60) Provisional application No. 60/632,432, filed on Dec. 1, 2004.

(51) Int. Cl.
*A61K 31/4184* (2006.01)
*C07D 235/04* (2006.01)

(52) U.S. Cl. ............. 514/394; 548/301.7; 548/302.7; 548/304.4; 548/309.4; 514/385; 514/393

(58) Field of Classification Search ............. 548/301.7, 548/302.7, 304.4, 309.4; 514/385, 393, 394
See application file for complete search history.

(56) References Cited

U.S. PATENT DOCUMENTS

| | | | |
|---|---|---|---|
| 3,951,920 | A | 4/1976 | Senoo |
| 4,975,435 | A | 12/1990 | Campbell |
| 5,118,688 | A | 6/1992 | Campbell |
| 5,563,143 | A | 10/1996 | Cohan |
| 5,688,809 | A | 11/1997 | Macor |
| 5,814,651 | A | 9/1998 | Duplantier |
| 5,972,980 | A | 10/1999 | Cornicelli |
| 6,001,866 | A | 12/1999 | Cornicelli |
| 6,087,380 | A | 7/2000 | Hauel |
| 6,162,804 | A | 12/2000 | Bilodeau |
| 6,218,388 | B1 | 4/2001 | Boshelli |
| 6,316,474 | B1 | 11/2001 | McCauley |
| 6,326,379 | B1 | 12/2001 | Macor |
| 6,329,383 | B1 | 12/2001 | Hedgecock |
| 6,348,474 | B1 | 2/2002 | Kayakiri |
| 6,414,008 | B1 | 7/2002 | Hauel |
| 6,444,617 | B1 | 9/2002 | Takaishi |

(Continued)

FOREIGN PATENT DOCUMENTS

EP 0 846 689 1/2004

| | | |
|---|---|---|
| WO | WO 00/76501 | 12/2001 |
| WO | WO 02/059118 | 8/2002 |

OTHER PUBLICATIONS

Ma Y et al. (2004), "Combinatorial Synthesis of Substituted Biaryls and Heterocyclic Arylamines", Journal of Combinatorial Chemistry, vol. 6, No. 3, pp. 426-430.
Salvino J M et al. (2000), "Polymer-Supported Tetrafluorophenol: A New Activated Resin For Chemical Library Synthesis", Journal of Combinatorial Chemistry, vol. 2, No. 6, pp. 691-697.
Vourloumis D et al. (2003), "Solid-phase Synthesis of Benzimidazole Libraries Biased for RNA Targets", Tetrahedron Letters, vol. 44, No. 14, pp. 2807-2811.
Yan, Bing et al. (2003), "Quality Control in Combinatorial Chemistry: Determination of the Quantity, Purity, and Quantitative Purity of Compounds in Combinatorial Libraries", Journal of Combinatorial Chemistry, 5 (5), pp. 547-559.
International Search Report in PCT/US2005/043114.
International Preliminary Report on Patentability and Written Opinion in PCT/US2005/043114.

*Primary Examiner*—Golam M Shameem

(57) ABSTRACT

Compounds represented by Formula (I):

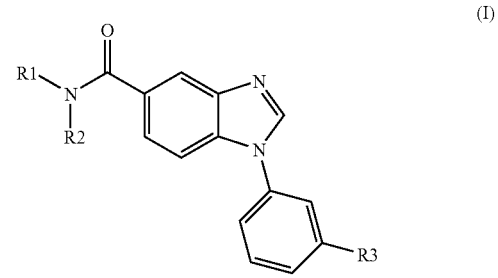

or a pharmaceutically acceptable salt or N-oxide thereof, are useful in the treatment of tumors. Combinatorial libraries composed of compounds represented by Formula (I) or benzimidazole compounds represented by Formula (II):

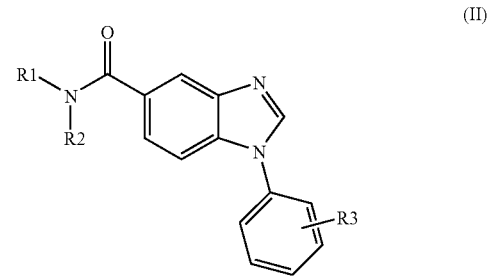

are useful in providing compounds to assay for such therapeutically useful compounds.

16 Claims, No Drawings

U.S. PATENT DOCUMENTS

| | | |
|---|---|---|
| 6,465,484 B1 | 10/2002 | Bilodeau |
| 6,469,039 B1 | 10/2002 | Hauel |
| 6,479,508 B1 | 11/2002 | Beaulieu |
| 6,512,000 B1 | 1/2003 | Anderskewitz |
| 6,534,503 B1 | 3/2003 | Dines |
| 6,534,535 B1 | 3/2003 | Zhu |
| 6,548,548 B2 | 4/2003 | Campbell |
| 6,558,893 B1 | 5/2003 | Parton |
| 6,583,169 B2 | 6/2003 | Horvath |
| 7,067,662 B2 | 6/2006 | Medina |
| 7,329,684 B2 | 2/2008 | Mjalli |
| 7,335,653 B2 | 2/2008 | Ungashe |
| 2002/0019395 A1 | 2/2002 | Zhu |
| 2002/0128232 A1 | 9/2002 | Henderson |
| 2003/0109714 A1 | 6/2003 | Wishart |
| 2005/0209176 A1 | 9/2005 | Meutermans |

US 7,419,995 B2

N-SUBSTITUTED BENZIMIDAZOYL C-KIT INHIBITORS AND COMBINATORIAL BENZIMIDAZOLE LIBRARY

This application claims the benefit of U.S. Patent Application No. 60/632,432 filed Dec. 1, 2004.

BACKGROUND OF THE INVENTION

The present invention is directed to N-substituted benzimidazolyl compounds. In particular, the present invention is directed to N-substituted benzimidazolyl compounds that are inhibitors of the c-Kit proto-oncogene (also known as KIT, CD-117, stem cell factor receptor, mast cell growth factor receptor). The present invention is also directed to (N1-substituted) benzimidazolyl compounds that are inhibitors of c-Kit.

The c-Kit proto-oncogene is believed to be important in embryogenesis, melanogenesis, hematopoiesis, and the pathogenesis of mastocytosis, gastrointestinal tumors, and other solid tumors, as well as certain leukemias, including AML. Accordingly, it would be desirable to develop novel compounds that are inhibitors of the c-Kit receptor.

Many of the current treatment regimes for hyperproliferative disorders (cancer) utilize compounds that inhibit DNA synthesis. Such compounds' mechanism of operation is to be toxic to cells, particularly to rapidly dividing tumor cells. Thus, their broad toxicity can be a problem to the subject patient. However, other approaches to anti-cancer agents that act other than by the inhibition of DNA synthesis have been explored to try to enhance the selectivity of the anti-cancer action and thereby reduce adverse side-effects.

It is known that a cell may become cancerous by virtue of the transformation of a portion of its DNA into an oncogene (i.e. a gene which, on activation, leads to the formation of malignant tumor cells). Many oncogenes encode proteins that are aberrant protein-tyrosine kinases capable of causing cell transformation. By a different route, the overexpression of a normal proto-oncogenic tyrosine kinase can also result in proliferative disorders, sometimes resulting in a malignant phenotype. Alternatively, co-expression of a receptor tyrosine kinase and its cognate ligand within the same cell type may also lead to malignant transformation.

Receptor tyrosine kinases are large enzymes which span the cell membrane and possess i) an extracellular binding domain for growth factors such as KIT ligand (also known as stem cell factor (SCF), Steel factor (SLF) or mast cell growth factor (MGF)), ii) a transmembrane domain, and iii) an intracellular portion which functions as a kinase to phosphorylate specific tyrosine residues in proteins. Binding of KIT ligand to KIT tyrosine kinase results in receptor homodimerization, the activation of KIT tyrosine kinase activity, and the subsequent phosphorylation of a variety of protein substrates, many of which are effectors of intracellular signal transduction, These events can lead to enhanced cell proliferation or promote enhanced cell survival. With some receptor kinases, receptor heterodimerization can also occur.

It is known that such kinases are frequently aberrantly expressed in common human cancers such as breast cancer, head and neck cancers, gastrointestinal cancer such as colon, rectal or stomach cancer, leukemia, and ovarian, bronchial, lung or pancreatic cancer. KIT kinase expression has been documented in a wide variety of human malignancies such as mastocytosis/mast cell leukemia, gastrointestinal stromal tumors (GIST), small cell lung carcinoma (SCLC), sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma. The kinase activity of KIT has been implicated in the pathophysiology of several of these—and additional tumors—including breast carcinoma, SCLC, GIST, germ cell tumors, mast cell leukemia, neuroblastoma, AML, melanoma and ovarian carcinoma.

Several mechanisms of KIT activation in tumor cells have been reported, including activating mutations, autocrine and paracrine activation of the receptor kinase by its ligand, loss of protein-tyrosine phosphatase activity, and cross activation by other kinases. The transforming mechanisms initiated by the activating mutations are thought to include dimer formation and increased intrinsic activity of the kinase domain, both of which result in constitutive ligand-independent kinase activation, and possibly altered substrate specificity. More than thirty activating mutations of the Kit protein have been associated with highly malignant tumors in humans.

Accordingly, it has been recognized that inhibitors of receptor tyrosine kinases are useful as selective inhibitors of the growth of mammalian cancer cells. For example, Gleevec™ (also known as imatinib mesylate, or STI571), a 2-phenylpyrimidine tyrosine kinase inhibitor that inhibits the kinase activity of the BCR-ABL fusion gene product, was recently approved by the U.S. Food and Drug Administration for the treatment of CML. Gleevec™, in addition to inhibiting BCR-ABL kinase, also inhibits the KIT kinase and PDGF receptor kinase, although it is not effective against all mutant isoforms of the KIT kinase. Kit ligand-stimulated growth of MO7e human leukemia cells is inhibited by Gleevec™, which also induces apoptosis under these conditions. By contrast, GM-CSF stimulated growth of MO7e human leukemia cells is not affected by Gleevec™. Further, in recent clinical studies using Gleevec™ to treat patients with GIST, a disease in which KIT kinase is involved in transformation of the cells, many of the patients showed marked improvement.

These studies demonstrate how KIT kinase inhibitors can treat tumors whose growth is dependent on KIT kinase activity. Other kinase inhibitors show even greater kinase selectivity. For example, the 4-anilinoquinazoline compound Tarceva™ inhibits only EGF receptor kinase with high potency, although it can inhibit the signal transduction of other receptor kinases, probably by virtue of the fact that these receptors heterodimerize with EGF receptor.

Although anti-cancer compounds such as those described above make a significant contribution to the art, there is a continuing need for improved anti-cancer pharmaceuticals, and it would be desirable to develop new compounds with better selectivity or potency, or with reduced toxicity or side effects.

U.S. Pat. Nos. 5,990,146 and 6,218,388 describe benzimidazoles for inhibiting protein tyrosine kinase mediated cellular proliferation. U.S. Pat. No. 6,348,032 describes method of inhibiting neoplastic cells with benzimidazole derivatives. International Patent Publication No. WO 01/21634 describes benzimidazole derivatives and combinatorial libraries thereof. International Patent Publication No. WO 01/57020 describes indole and benzimidazole inhibitors of factor Xa.

International Patent Publication No. WO 00/15222 describes fused pyridine inhibitors of cGMP phosphodiesterase. International Patent Publication No. WO 01/12600 describes inhibitors of Factor Xa. International Patent Publication No. WO 97/12613 describes method for treating and preventing inflammation and atherosclerosis.

U.S. Pat. No. 6,316,474 describes 2-benzyl and 2-heteroaryl benzimidazole NMDA/NR2b antagonists. U.S. Pat. No. 6,479,508 describes viral polymerase inhibitors. U.S. Pat. No. 6,444,617 describes fused-heterocycle dicarboxylic acid diamide derivatives or salts thereof, herbicide and usage thereof. U.S. Pat. Nos. 6,087,380, 6,414,008, and 6,469,039 describe disubstituted bicyclic heterocycles. U.S. Pat. No. 5,118,688 describes tetrahydropyridonquinolone derivatives. U.S. Pat. No. 4,975,435 describes certain 1H-pyrrolo[3,4-b]quinolin-1-one-9-amino-2,3-dihydro derivatives useful for treating anxiety. U.S. Pat. No. 6,548,524 describes orthosulfonamido bicyclic heteroaryl hydroxamic acids. U.S. Pat. No. 6,348,474 describes sulfonamide compounds.

U.S. Pat. Nos. 5,972,980 and 6,001,866 describe method for treating and preventing inflammation and atherosclerosis. U.S. Pat. No. 5,814,651 describes catechol diethers as selective PDEIV inhibitors. U.S. Pat. No. 6,329,383 describes 2-amino-5-pyrimidine acetic acid compounds. U.S. Pat. No. 5,688,809 describes 5-heteroarylindole derivatives. European Patent Application No. EP 0 846 689 describes benzimidazole compounds. International Patent Publication No. WO 00/59888 describes N-benzimidazolylmethyl- and N-indolylmethyl-benzamides and their use as CRF modulators. International Patent Publication No. WO 02/069965 describes benzimidazole derivatives as therapeutic agents. International Patent Publication No. WO 02/30886 describes heterocyclic angiogenesis inhibitors. U.S. Pat. No. 6,162,804 describes tyrosine kinase inhibitors. U.S. Pat. No. 6,465,484 describes angiogenesis inhibitors. International Patent Publication No. WO 00/12089 describes novel angiogenesis inhibitors.

German Patent Publication No. DE 2244908 describes selectively permeable polymeric membranes. European Patent Application No. EP 0 706 795 describes catechol diether compounds as inhibitors of TNF release. International Patent Publication No. WO 02/076960 describes transition metal mediated process. International Patent Publication No. WO 02/059118 describes process for N-(oxyalkylation) of carboxamides. International Patent Publication No. WO 02/04425 describes viral polymerase inhibitors. International Patent Publication No. WO 02/083143 describes CXCR3 antagonists. International Patent Publication No. WO 01/57019 describes indolone and benzimidazolone inhibitors of factor Xa. European Patent Application No. EP 1 085 372 describes photographic material having improved color reproduction. International Patent Publication No. WO 01/14342 describes aminocarbonyl-substituted benzimidazole derivatives. International Patent Publication No. WO 00/76501 describes IL-8 receptor antagonists.

Thus, it is desirable to develop compounds that exhibit Kit inhibition in order to treat oncology. Further, such compounds may be active in other kinases such as, for example, GIST, FLT3, Hematopoietic R-PTKs, PDGFR-beta or KDR to add efficacy in mast cell leukemias, small cell lung cancer (SCLC), mastocytosis, leukemias, myelodysplastic disorders, or angiogenic dependent diseases.

SUMMARY OF THE INVENTION

Compounds represented by Formula (I):

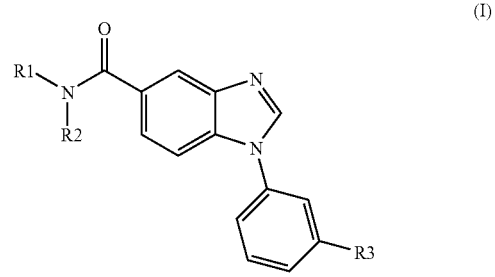

or a pharmaceutically acceptable salt or N-oxide thereof, are useful in the treatment of tumors. Combinatorial libraries composed of compounds represented by Formula (I) or benzimidazole compounds represented by Formula (II):

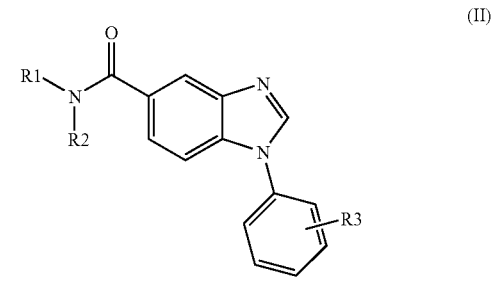

are useful in providing compounds to assay for such therapeutically useful compounds.

DETAILED DESCRIPTION OF THE INVENTION

The present invention is directed to a compound represented by Formula (I):

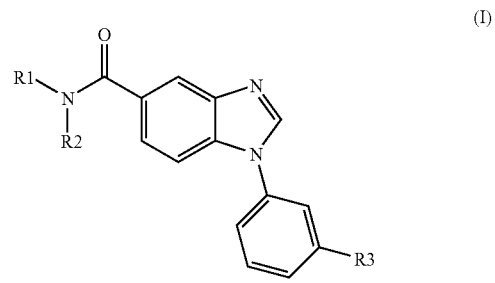

or a pharmaceutically acceptable salt or N-oxide thereof, wherein

R1 and R2 are independently
  $C_{0-8}$alkyl optionally substituted with a heterocyclyl substituent,
  $C_{0-8}$alkyl optionally substituted with 1-6 independent halo, —CONR$^{11}$R$^{12}$,
—NR$^{13}$CONR$^{11}$R$^{12}$, —NR$^{13}$CO$_2$R$^{11}$, —S(O)$_{0-2}$NR$^{11}$R$^{12}$, —NR$^{11}$S(O)$_{0-2}$R$^{12}$, CN, OH, or
optionally substituted aryl substituents;

—$C_{0-8}$alkyl-$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-S(O)$_{0-2}$—$C_{0-8}$alkyl; or
heterocyclyl optionally substituted with 1-4 independent $C_{0-8}$alkyl, cyclyl, or substituted cyclyl substituents;

or R1 and R2, taken together with the nitrogen to which they are joined, form a heterocyclic group, optionally substituted with 1-4 independent $C_{0-8}$alkyl, —$C_{0-8}$alkyl-O—$C_{0-8}$alkyl, —$C_{0-8}$alkyl-aryl, or —$C_{0-8}$alkyl-heteroaryl groups, provided that the heterocyclic group formed is not piperazine;

R3 is an aryl or hetaryl group, optionally substituted with 1-4 independent $C_{0-8}$alkyl, $C_{0-8}$alkyl-cyclyl, halo, OH, —$NR^{31}S(O)_{0-2}R^{32}$, —$S(O)_{0-2}NR^{31}R^{32}$, —$NR^{31}COR^{32}$, —$NR^{31}CONR^{32}R^{33}$, —$CONR^{31}R^{32}$, $S(O)_{0-2}R^{31}$, —O-aryl, —O-hetaryl, $NO_2$, CN, $CF_3$, $OCF_3$, $OCHF_2$;

$R^{11}$, $R^{12}$, $R^{13}$, $R^{31}$, $R^{32}$, and $R^{33}$ are each independently
$C_{0-8}$alkyl optionally substituted with a heterocyclyl substituent,
$C_{0-8}$alkyl optionally substituted with 1-6 independent halo, —$CON(C_{0-8}$alkyl$)(C_{0-8}$alkyl$)$, —$N(C_{0-8}$alkyl$)CON(C_{0-8}$alkyl$)(C_{0-8}$alkyl$)$, —$N(C_{0-8}$alkyl$)CO_2(C_{0-8}$alkyl$)$, $S(O)_{0-2}N(C_{0-8}$alkyl$)(C_{0-8}$alkyl$)$, —$NR^{11}S(O)_{0-2}(C_{0-8}$alkyl$)$, CN, OH, or optionally substituted aryl substituents;
—$C_{0-8}$alkyl-$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-S(O)$_{0-2}$—$C_{0-8}$alkyl; or
heterocyclyl optionally substituted with 1-4 independent $C_{0-8}$alkyl, cyclyl, or substituted cyclyl substituents; and
provided that R3 is not a tetrazolyl, 5-pyrimidinyl, or 4-biphenyl group.

In one aspect, the present invention is directed to a compound represented by Formula (I), or a pharmaceutically acceptable salt or N-oxide thereof, wherein R3 is an optionally substituted aryl group, and the other variables are as described above for Formula (I).

In an embodiment of this one aspect, the present invention is directed to a compound represented by Formula (I), or a pharmaceutically acceptable salt or N-oxide thereof, wherein R3 is an optionally substituted aryl group, R1 is heterocyclyl optionally substituted with 1-4 independent $C_{0-8}$alkyl, cyclyl, or substituted cyclyl substituents; and the other variables are as described above for Formula (I).

In another embodiment of this one aspect, the present invention is directed to a compound represented by Formula (I), or a pharmaceutically acceptable salt or N-oxide thereof, wherein R3 is an optionally substituted aryl group, R1 is $C_{0-8}$alkyl optionally substituted with a heterocyclyl substituent; or R1 is $C_{0-8}$alkyl optionally substituted with 1-6 independent halo, —$CONR^{11}R^{12}$, —$NR^{13}CONR^{11}R^{12}$, —$NR^{13}CO_2R^{11}$, —$S(O)_{0-2}NR^{11}R^{12}$, CN, OH, or optionally substituted aryl substituents; and the other variables are as described above for Formula (I).

In yet another embodiment of this one aspect, the present invention is directed to a compound represented by Formula (I), or a pharmaceutically acceptable salt or N-oxide thereof, wherein R3 is an optionally substituted aryl group, R1 is —$C_{0-8}$alkyl-N($C_{0-8}$alkyl)($C_{0-8}$alkyl); and the other variables are as described above for Formula (I).

In a second aspect, the present invention is directed to a compound represented by Formula (I), or a pharmaceutically acceptable salt or N-oxide thereof, wherein R3 is an optionally substituted hetaryl group, and the other variables are as described above for Formula (I).

In an embodiment of this second aspect, the present invention is directed to a compound represented by Formula (I), or a pharmaceutically acceptable salt or N-oxide thereof, wherein R3 is an optionally substituted hetaryl group, R1 is heterocyclyl optionally substituted with 1-4 independent $C_{0-8}$alkyl, cyclyl, or substituted cyclyl substituents; and the other variables are as described above for Formula (I).

In another embodiment of this second aspect, the present invention is directed to a compound represented by Formula (I), or a pharmaceutically acceptable salt or N-oxide thereof, wherein R3 is an optionally substituted hetaryl group, R1 is —$C_{0-8}$alkyl optionally substituted with a heterocyclyl substituent; or R1 is $C_{0-8}$alkyl optionally substituted with 1-6 independent halo, —$CONR^{11}R^{12}$, —$NR^{13}CONR^{11}R^{12}$, —$NR^{13}CO_2R^{11}$, —$S(O)_{0-2}NR^{11}R^{12}$, —$NR^{11}S(O)_{0-2}R^{12}$, CN, OH, or optionally substituted aryl substituents; and the other variables are as described above for Formula (I).

In yet another embodiment of this second aspect, the present invention is directed to a compound represented by Formula (I), or a pharmaceutically acceptable salt or N-oxide thereof, wherein R3 is an optionally substituted hetaryl group, R1 is —$C_{0-8}$alkyl-N($C_{0-8}$alkyl)($C_{0-8}$alkyl); and the other variables are as described above for Formula (I).

The compounds of the present invention include
1-(4'-cyano-1,1'-biphenyl-3-yl)-N-pyridin-3-ylmethyl-1H-benzimidazole-5-carboxamide,
N-(pyridin-3-ylmethyl)-1-(3-thien-3-ylphenyl)-1H-benzimidazole-5-carboxamide,
1-(3'-chloro-4'-fluoro-1,1'-biphenyl-3-yl)-N-(pyridin-3-ylmethyl)-1H-benzimidazole-5-carboxamide,
1-(3'-cyano-1,1'-biphenyl-3-yl)-N-(pyridin-3-ylmethyl)-1H-benzimidazole-5-carboxamide,
1-(3'-nitro-1,1'-biphenyl-3-yl)-N-(pyridin-3-ylmethyl)-1H-benzimidazole-5-carboxamide,
1-(2'-nitro-1,1'-biphenyl-3-yl)-N-(pyridin-3-ylmethyl)-1H-benzimidazole-5-carboxamide,
or a pharmaceutically acceptable salt or N-oxide thereof.

The compounds of the present invention also include
1-[3'-(acetylamino)-1,1'-biphenyl-3-yl]-N-methyl-1H-benzimidazole-5-carboxamide,
1-(3'-chloro-4'-fluoro-1,1'-biphenyl-3-yl)-N-methyl-1H-benzimidazole-5-carboxamide,
1-(1,1'-biphenyl-3-yl)-N-methyl-1H-benzimidazole-5-carboxamide,
N-methyl-1-(2'-phenoxy-1,1'-biphenyl-3-yl)-1H-benzimidazole-5-carboxamide,
N-methyl-1-{3'-[(methylsulfonyl)amino]-1,1'-biphenyl-3-yl}-1H-benzimidazole-5-carboxamide,
1-(1,1'-biphenyl-3-yl)-N-methyl-1H-benzimidazole-5-carboxamide,
N-methyl-1-(4'-methyl-1,1'-biphenyl-3-yl)-1H-benzimidazole-5-carboxamide,
1-(3'-fluoro-1,1'-biphenyl-3-yl)-N-methyl-1H-benzimidazole-5-carboxamide,
N-methyl-1-[4'-(methylsulfonyl)-1,1'-biphenyl-3-yl]-1H-benzimidazole-5-carboxamide,
or a pharmaceutically acceptable salt or N-oxide thereof.

Further, the compounds of the present invention include
N-(pyridin-3-ylmethyl)-1-[3-(1H-pyrrol-2-yl)phenyl]-1H-benzimidazole-5-carboxamide,
N-(pyridin-3-ylmethyl)-1-(3-pyridin-3-ylphenyl)-1H-benzimidazole-5-carboxamide,
1-[3-(1-benzyl-1H-pyrazol-4-yl)phenyl]-N-(pyridin-3-ylmethyl)-1H-benzimidazole-5-carboxamide, N-(pyridin-3-ylmethyl)-1-[3-(1H-pyrrol-3-yl)phenyl]-1H-benzimidazole-5-carboxamide,
1-[3-(1-methyl-1H-pyrrol-2-yl)phenyl]-N-(Pyridin-3-ylmethyl)-1H-benzimidazole-5-carboxamide,
N-(pyridin-3-ylmethyl)-1-[3-(1,3-thiazol-2-yl)phenyl]-1H-benzimidazole-5-carboxamide,
1-[3-(3,5-dimethylisoxazol-4-yl)phenyl]-N-tetrahydro-2H-pyran-4-yl-1H-benzimidazole-5-carboxamide,
N-tetrahydro-2H-pyran-4-yl-1-(3-thien-3-ylphenyl)-1H-benzimidazole-5-carboxamide,
N-tetrahydro-2H-pyran-4-yl-1-(3-pyrrol-2-ylphenyl)-1H-benzimidazole-5-carboxamide,
N-(1,3-benzodioxol-5-ylmethyl)-1-[3-(1H-pyrrol-1-yl)phenyl]-1H-benzimidazole-5-carboxamide,
or a pharmaceutically acceptable salt or N-oxide thereof.

Further, the compounds of the present invention also include

N-methyl-1-(3-thien-3-ylphenyl)-1H-benzimidazole-5-carboxamide,
N-methyl-1-[3-(1H-pyrrol-2-yl)phenyl]-1H-benzimidazole-5-carboxamide,
N-ethyl-1-(3-thien-3-ylphenyl)-1H-benzimidazole-5-carboxamide,
N-ethyl-1-[3-(1H-pyrrol-2-yl)phenyl]-1H-benzimidazole-5-carboxamide,
N-methyl-1-(3-pyridin-3-ylphenyl)-1H-benzimidazole-5-carboxamide,
1-[3-(1,3-benzodioxol-5-yl)phenyl]-N-methyl-1H-benzimidazole-5-carboxamide,
1-[3-(2,3-dihydro-1-benzofuran-5-yl)phenyl]-N-methyl-1H-benzimidazole-5-carboxamide,
1-[3-(5-chlorothien-2-yl)phenyl]-N-methyl-1H-benzimidazole-5-carboxamide,
N-methyl-1-(3-thien-2-ylphenyl)-1H-benzimidazole-5-carboxamide,
1-(3-thien-3-ylphenyl)-1H-benzimidazole-5-carboxamide,
N-(tert-butyl)-1-(3-thien-3-ylphenyl)-1H-benzimidazole-5-carboxamide,
1-[3-(3,5-dimethylisoxazol-4-yl)phenyl]-N-methyl-1H-benzimidazole-5-carboxamide,
1-[3-(3,5-dimethylisoxazol-4-yl)phenyl]-N-ethyl-1H-benzimidazole-5-carboxamide,
N-methyl-1-[3-(2-naphthyl)phenyl]-1H-benzimidazole-5-carboxamide,
1-[3-(1-benzothien-2-yl)phenyl]-N-methyl-1H-benzimidazole-5-carboxamide,
N-(pyridin-3-ylmethyl)-1-[3-(1H-pyrrol-1-yl)phenyl]-1H-benzimidazole-5-carboxamide,
or a pharmaceutically acceptable salt or N-oxide thereof.

The compounds of the present invention also include

N-[2-(dimethylamino)ethyl]-1-(3-thien-3-ylphenyl)-1H-benzimidazole-5-carboxamide,
N-[2-(dimethylamino)ethyl]-1-[3-(3,5-dimethylisoxazol-4-yl)phenyl]-1H-benzimidazole-5-carboxamide,
N-[2-(dimethylamino)ethyl]-1-(3-pyrrol-2-ylphenyl)-1H-benzimidazole-5-carboxamide,
or a pharmaceutically acceptable salt or N-oxide thereof.

Thus, the compounds of the present invention include 1-(4'-cyano-1,1'-biphenyl-3-yl)-N-pyridin-3-ylmethyl-1H-benzimidazole-5-carboxamide,
N-(pyridin-3-ylmethyl)-1-(3-thien-3-ylphenyl)-1H-benzimidazole-5-carboxamide,
N-(pyridin-3-ylmethyl)-1-[3-(1H-pyrrol-2-yl)phenyl]-1H-benzimidazole-5-carboxamide,
1-(3'-chloro-4'-fluoro-1,1'-biphenyl-3-yl)-N-(pyridin-3-ylmethyl)-1H-benzimidazole-5-carboxamide,
1-(3'-cyano-1,1'-biphenyl-3-yl)-N-(pyridin-3-ylmethyl)-1H-benzimidazole-5-carboxamide,
1-(3'-nitro-1,1'-biphenyl-3-yl)-N-(pyridin-3-ylmethyl)-1H-benzimidazole-5-carboxamide,
N-(pyridin-3-ylmethyl)-1-(3-pyridin-3-ylphenyl)-1H-benzimidazole-5-carboxamide,
1-[3-(1-benzyl-1H-pyrazol-4-yl)phenyl]-N-(pyridin-3-ylmethyl)-1H-benzimidazole-5-carboxamide,
N-(pyridin-3-ylmethyl)-1-[3-(1H-pyrrol-3-yl)phenyl]-1H-benzimidazole-5-carboxamide,
1-[3-(1-methyl-1H-pyrrol-2-yl)phenyl]-N-(Pyridin-3-ylmethyl)-1H-benzimidazole-5-carboxamide,
1-(2'-nitro-1,1'-biphenyl-3-yl)-N-(pyridin-3-ylmethyl)-1H-benzimidazole-5-carboxamide,
N-(pyridin-3-ylmethyl)-1-[3-(1,3-thiazol-2-yl)phenyl]-1H-benzimidazole-5-carboxamide,
N-methyl-1-(3-thien-3-ylphenyl)-1H-benzimidazole-5-carboxamide,
N-methyl-1-[3-(1H-pyrrol-2-yl)phenyl]-1H-benzimidazole-5-carboxamide,
N-ethyl-1-(3-thien-3-ylphenyl)-1H-benzimidazole-5-carboxamide,
N-ethyl-1-[3-(1H-pyrrol-2-yl)phenyl]-1H-benzimidazole-5-carboxamide,
N-methyl-1-(3-pyridin-3-ylphenyl)-1H-benzimidazole-5-carboxamide,
N-[2-(dimethylamino)ethyl]-1-(3-thien-3-ylphenyl)-1H-benzimidazole-5-carboxamide,
1-[3'-(acetylamino)-1,1'-biphenyl-3-yl]-N-methyl-1H-benzimidazole-5-carboxamide,
1-(3'-chloro-4'-fluoro-1,1'-biphenyl-3-yl)-N-methyl-1H-benzimidazole-5-carboxamide,
1-[3-(1,3-benzodioxol-5-yl)phenyl]-N-methyl-1H-benzimidazole-5-carboxamide,
1-(1,1'-biphenyl-3-yl)-N-methyl-1H-benzimidazole-5-carboxamide,
N-methyl-1-(2'-phenoxy-1,1'-biphenyl-3-yl)-1H-benzimidazole-5-carboxamide,
1-[3-(2,3-dihydro-1-benzofuran-5-yl)phenyl]-N-methyl-1H-benzimidazole-5-carboxamide,
N-methyl-1-{3'-[(methylsulfonyl)amino]-1,1'-biphenyl-3-yl}-1H-benzimidazole-5-carboxamide,
1-[3-(5-chlorothien-2-yl)phenyl]-N-methyl-1H-benzimidazole-5-carboxamide,
N-methyl-1-(3-thien-2-ylphenyl)-1H-benzimidazole-5-carboxamide,
1-(1,1'-biphenyl-3-yl)-N-methyl-1H-benzimidazole-5-carboxamide,
N-methyl-1-(4'-methyl-1,1'-biphenyl-3-yl)-1H-benzimidazole-5-carboxamide,
1-(3'-fluoro-1,1'-biphenyl-3-yl)-N-methyl-1H-benzimidazole-5-carboxamide,
1-(3-thien-3-ylphenyl)-1H-benzimidazole-5-carboxamide,
N-(tert-butyl)-1-(3-thien-3-ylphenyl)-1H-benzimidazole-5-carboxamide,
1-[3-(3,5-dimethylisoxazol-4-yl)phenyl]-N-methyl-1H-benzimidazole-5-carboxamide,
1-[3-(3,5-dimethylisoxazol-4-yl)phenyl]-N-ethyl-1H-benzimidazole-5-carboxamide,
N-[2-(dimethylamino)ethyl]-1-[3-(3,5-dimethylisoxazol-4-yl)phenyl]-1H-benzimidazole-5-carboxamide,
1-[3-(3,5-dimethylisoxazol-4-yl)phenyl]-N-tetrahydro-2H-pyran-4-yl-1H-benzimidazole-5-carboxamide,
N-tetrahydro-2H-pyran-4-yl-1-(3-thien-3-ylphenyl)-1H-benzimidazole-5-carboxamide, N-tetrahydro-2H-pyran-4-yl-1-(3-pyrrol-2-ylphenyl)-1H-benzimidazole-5-carboxamide,
N-methyl-1-[3-(2-naphthyl)phenyl]-1H-benzimidazole-5-carboxamide,
N-methyl-1-[4'-(methylsulfonyl)-1,1'-biphenyl-3-yl]-1H-benzimidazole-5-carboxamide,
1-[3-(1-benzothien-2-yl)phenyl]-N-methyl-1H-benzimidazole-5-carboxamide,
N-[2-(dimethylamino)ethyl]-1-(3-pyrrol-2-ylphenyl)-1H-benzimidazole-5-carboxamide,
N-(pyridin-3-ylmethyl)-1-[3-(1H-pyrrol-1-yl)phenyl]-1H-benzimidazole-5-carboxamide,
N-(1,3-benzodioxol-5-ylmethyl)-1-[3-(1H-pyrrol-1-yl)phenyl]-1H-benzimidazole-5-carboxamide,
or a pharmaceutically acceptable salt or N-oxide thereof.

The present invention is also directed to a combinatorial library comprising at least three compounds represented by Formula (II):

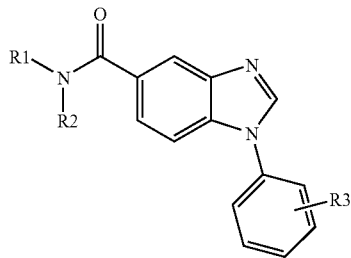

(II)

or a pharmaceutically acceptable salt or N-oxide thereof, wherein

R1 and R2 are independently
$C_{0-8}$alkyl optionally substituted with a heterocyclyl substituent,
$C_{0-8}$alkyl optionally substituted with 1-6 independent halo, —$CONR^{11}R^{12}$,
—$NR^{13}CONR^{11}R^{12}$, —$NR^{13}CO_2R^{11}$, —$S(O)_{0-2}NR^{11}R^{12}$, —$NR^{11}S(O)_{0-2}R^{12}$, CN, OH, or optionally substituted aryl substituents;
—$C_{0-8}$alkyl-$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-S(O)$_{0-2}$—$C_{0-8}$alkyl; or
heterocyclyl optionally substituted with 1-4 independent $C_{0-8}$alkyl, cyclyl, or
substituted cyclyl substituents;
or R1 and R2, taken together with the nitrogen to which they are joined, form a heterocyclic group, optionally substituted with 1-4 independent $C_{0-8}$alkyl, —$C_{0-8}$alkyl-O—$C_{0-8}$alkyl, —$C_{0-8}$alkyl-aryl, or —$C_{0-8}$alkyl-heteroaryl groups;
R3 is an aryl or hetaryl group, optionally substituted with 1-4 independent $C_{0-8}$alkyl, $C_{0-8}$alkyl-cyclyl, halo, OH, —$NR^{31}S(O)_{0-2}R^{32}$, —$S(O)_{0-2}NR^{31}R^{32}$, —$NR^{31}COR^{32}$, —$NR^{31}CONR^{32}R^{33}$, —$CONR^{31}R^{32}$, $S(O)_{0-2}R^{31}$, —O-aryl, —O-hetaryl, $NO_2$, CN, $CF_3$, $OCF_3$, $OCHF_2$;
$R^{11}$, $R^{12}$, $R^{13}$, $R^{31}$, $R^{32}$, and $R^{33}$ are each independently
$C_{0-8}$alkyl optionally substituted with a heterocyclyl substituent,
$C_{0-8}$alkyl optionally substituted with 1-6 independent halo, —$CON(C_{0-8}$alkyl)($C_{0-8}$alkyl), —$N(C_{0-8}$alkyl)$CON(C_{0-8}$alkyl)($C_{0-8}$alkyl), —$N(C_{0-8}$alkyl)$CO_2(C_{0-8}$alkyl), $S(O)_{0-2}N(C_{0-8}$alkyl)($C_{0-8}$alkyl), —$NR^{11}S(O)_{0-2}(C_{0-8}$alkyl), CN, OH, or optionally substituted aryl substituents;
—$C_{0-8}$alkyl-$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-S(O)$_{0-2}$—$C_{0-8}$alkyl; or
heterocyclyl optionally substituted with 1-4 independent $C_{0-8}$alkyl, cyclyl, or
substituted cyclyl substituents.

The present invention is also directed to a process to form a combinatorial library comprising at least three compounds represented by Formula (II):

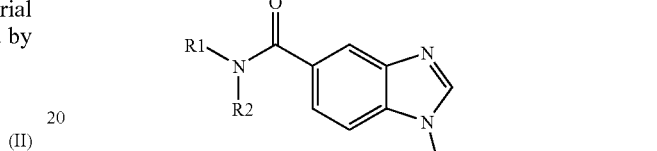

(II)

or a pharmaceutically acceptable salt or N-oxide thereof, wherein

R1 and R2 are independently
$C_{0-8}$alkyl optionally substituted with a heterocyclyl substituent,
$C_{0-8}$alkyl optionally substituted with 1-6 independent halo, —$CONR^{11}R^{12}$,
—$NR^{13}CONR^{11}R^{12}$, —$NR^{13}CO_2R^{11}$, —$S(O)_{0-2}NR^{11}R^{12}$, —$NR^{11}S(O)_{0-2}R^{12}$ CN, OH, or
optionally substituted aryl substituents;
—$C_{0-8}$alkyl-$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-S(O)$_{0-2}$—$C_{0-8}$alkyl; or
heterocyclyl optionally substituted with 1-4 independent $C_{0-8}$alkyl, cyclyl, or
substituted cyclyl substituents;
or R1 and R2, taken together with the nitrogen to which they are joined, form a heterocyclic group, optionally substituted with 1-4 independent $C_{0-8}$alkyl, —$C_{0-8}$alkyl-O—$C_{0-8}$alkyl, —$C_{0-8}$alkyl-aryl, or —$C_{0-8}$alkyl-heteroaryl groups;
R3 is an aryl or hetaryl group, optionally substituted with 1-4 independent $C_{0-8}$alkyl, $C_{0-8}$alkyl-cyclyl, halo, OH, —$NR^{31}S(O)_{0-2}R^{32}$, —$S(O)_{0-2}NR^{31}R^{32}$, —$NR^{31}CONR^{32}R^{33}$, —$CONR^{31}R^{32}$, $S(O)_{0-2}R^{31}$, —O-aryl, —O-hetaryl, $NO_2$, CN, $CF_3$, $OCF_3$, $OCHF_2$;
$R^{11}$, $R^{12}$, $R^{13}$, $R^{31}$, $R^{32}$, and $R^{33}$ are each independently
$C_{0-8}$alkyl optionally substituted with a heterocyclyl substituent,
$C_{0-8}$alkyl optionally substituted with 1-6 independent halo, —$CON(C_{0-8}$alkyl )($C_{0-8}$alkyl), —$N(C_{0-8}$alkyl)$CON(C_{0-8}$alkyl)($C_{0-8}$alkyl), —$N(C_{0-8}$alkyl)$CO_2(C_{0-8}$alkyl), $S(O)_{0-2}N(C_{0-8}$alkyl)($C_{0-8}$alkyl), —$NR^{11}S(O)_{0-2}(C_{0-8}$alkyl), CN, OH, or optionally substituted aryl substituents;
—$C_{0-8}$alkyl-$C_{3-8}$cycloalkyl,
—$C_{0-8}$alkyl-O—$C_{0-8}$alkyl,
—$C_{0-8}$alkyl-N($C_{0-8}$alkyl)($C_{0-8}$alkyl),
—$C_{0-8}$alkyl-S(O)$_{0-2}$—$C_{0-8}$alkyl; or heterocyclyl optionally substituted with 1-4 independent $C_{0-8}$alkyl, cyclyl, or substituted cyclyl substituents.

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

The terms "cycloalkyl", "carbocyclic ring", "cyclic", or "cyclyl" mean 3-10 membered mono or polycyclic aromatic, partially aromatic or non-aromatic ring carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-8}$cycloalkyl such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "carbamoyl" unless specifically described otherwise means —C(O)—NH— or —NH—C(O)—.

The term "aryl" is well known to chemists. The preferred aryl groups are phenyl and naphthyl.

The term "hetaryl" is well known to chemists. The term includes 5- or 6-membered heteroaryl rings containing 1-4 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The term "hetaryl" includes hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like.

Unless otherwise stated, the terms "heterocyclic ring", "heterocycle", "heterocyclic", and "heterocyclyl" are equivalent, and is defined as for cyclic but also contains one or more atoms chosen independently from N, O, and S (and the N and S oxides), provided such derivatives exhibit appropriate and stable valencies and excludes moieties containing O—O, $S(O)_n$—$S(O)_n$, $S(O)_n$—O bonds where n=0-2. The terms include 4-8-membered saturated rings containing one or two heteroatoms chosen from oxygen, sulfur, and nitrogen. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, azepane, azocane, [1,3]dioxane, oxazolidine, piperazine, homopiperazine, morpholine, thiomorpholine, and the like. Other examples of heterocyclic rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems, including het-het fused systems, and can include a carbocyclic ring that is partially or fully unsaturated, such as a benzene ring, to form benzofused heterocycles. For example, 3,4,-dihydro-1,4-benzodioxine, tetrahydroquinoline, tetrahydroisoquinoline and the like.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The invention also encompasses a pharmaceutical composition that is comprised of a compound of Formula I in combination with a pharmaceutically acceptable carrier.

Preferably, the composition is comprised of a pharmaceutically acceptable carrier and a non-toxic therapeutically effective amount of a compound of Formula I as described above (or a pharmaceutically acceptable salt or N-oxide thereof).

Moreover, within this preferred embodiment, the invention encompasses a pharmaceutical composition for the treatment of disease by the inhibition of the c-Kit kinase, which may be a wild-type or mutant form of the protein, comprising a pharmaceutically acceptable carrier and a non-toxic therapeutically effective amount of compound of Formula I as described above (or a pharmaceutically acceptable salt or N-oxide thereof).

The compounds and compositions of the present invention are effective for treating mammals such as, for example, humans.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrochloric, maleic, phosphoric, sulfuric, methanesulfonic, and tartaric acids.

The pharmaceutical compositions of the present invention comprise a compound represented by formula I (or a pharmaceutically acceptable salt or N-oxide thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts or N-oxides thereof, of this invention can be combined as the active ingredient in intimate admixture with a pharmaceutical carrier according to conventional pharmaceutical compounding techniques. The carrier may take a wide variety of forms depending on the form of preparation desired for administration. E.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt or N-oxide thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt or N-oxide of Formula I. The compounds of Formula I, or pharmaceutically acceptable salts or N-oxides thereof, can also be included in pharmaceutical compositions in combination with one or more other therapeutically active compounds.

The pharmaceutical compositions of this invention include a pharmaceutically acceptable liposomal formulation containing a compound of Formula I or a pharmaceutically acceptable salt or N-oxide thereof.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent or other such excipient. These excipients may be, for example, inert diluents such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer time. For example, a time delay material such as glyceryl monostearate or glyceryl distearate may be used.

In hard gelatin capsules, the active ingredient is mixed with an inert solid diluent, for example, calcium carbonate, calcium phosphate or kaolin. In soft gelatin capsules, the active ingredient is mixed with water or an oil medium, for example, peanut oil, liquid paraffin or olive oil. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material, which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt or N-oxide thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts or N-oxides thereof, may also be prepared in powder or liquid concentrate form.

Generally, dosage levels on the order of from about 0.01 mg/kg to about 750 mg/kg of body weight per day are useful in the treatment of the above-indicated conditions, or alternatively about 0.5 mg to about 75 g per patient per day. For example, breast cancer, head and neck cancers, and gastrointestinal cancer such as colon, rectal or stomach cancer may be effectively treated by the administration of from about 0.01 to 500 mg of the compound per kilogram of body weight per day, or alternatively about 0.5 mg to about 50 g per patient per day.

Similarly, leukemia, ovarian, bronchial, lung, and pancreatic cancer may be effectively treated by the administration of from about 0.01 to 500 mg of the compound per kilogram of body weight per day, or alternatively about 0.5 mg to about 50 g per patient per day.

Mastocytosis/mast cell leukemia, gastrointestinal stromal tumors (GIST), small cell lung carcinoma (SCLC), colon cancer, sinonasal natural killer/T-cell lymphoma, testicular cancer (seminoma), thyroid carcinoma, malignant melanoma, ovarian carcinoma, adenoid cystic carcinoma, acute myelogenous leukemia (AML), breast carcinoma, pediatric T-cell acute lymphoblastic leukemia, angiosarcoma, anaplastic large cell lymphoma, endometrial carcinoma, and prostate carcinoma may be effectively treated by the administration of from about 0.01 to 500 mg of the compound per kilogram of body weight per day, or alternatively about 0.5 mg to about 50 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention, or pharmaceutically acceptable salts or N-oxides thereof, can also be effectively administered in conjunction with other cancer therapeutic compounds. For example, cytotoxic agents and angiogenesis inhibiting agents can be advantageous co-agents with the compounds of the present invention. Accordingly, the present invention includes compositions comprising the compounds represented by Formula I, or a pharmaceutically acceptable salt or N-oxide thereof, and a cytotoxic agent or an angiogenesis-inhibiting agent. The amounts of each can be therapeutically effective alone—in which case the additive effects can overcome cancers resistant to treatment by monotherapy. The amounts of any can also be subtherapeutic—to minimize adverse effects, particularly in sensitive patients.

It is understood that the treatment of cancer depends on the type of cancer. For example, lung cancer is treated differently as a first line therapy than are colon cancer or breast cancer treated. Even within lung cancer, for example, first line therapy is different from second line therapy, which in turn is different from third line therapy. Newly diagnosed patients might be treated with cisplatinum containing regimens. Were that to fail, they move onto a second line therapy such as a taxane. Finally, if that failed, they might get a tyrosine kinase EGFR inhibitor as a third line therapy. Further, The regulatory approval process differs from country to country. Accordingly, the accepted treatment regimens can differ from country to country. Nevertheless, the compounds of the present invention, or pharmaceutically acceptable salts or N-oxides thereof, can be beneficially co-administered in conjunction or combination with other such cancer therapeutic compounds. Such other compounds include, for example, a variety of cytotoxic agents (alkylators, DNA topoisomerase inhibitors, antimetabolites, tubulin binders); inhibitors of angiogenesis; and different other forms of therapies including kinase inhibitors such as Tarceva, monoclonal antibodies, and cancer vaccines. Other such compounds that can be beneficially co-administered with the compounds of the present invention include doxorubicin, vincristine, cisplatin, carboplatin, gemcitabine, and the taxanes. Thus, the compositions of the present invention include a compound according to Formula I, or a pharmaceutically acceptable salt or N-oxide thereof, and an anti-neoplastic, anti-tumor, anti-angiogenic, or chemotherapeutic agent.

The compounds of the present invention, or pharmaceutically acceptable salts or N-oxides thereof, can also be effectively administered in conjunction with other therapeutic compounds, aside from cancer therapy. For example, therapeutic agents effective to ameliorate adverse side-effects can be advantageous co-agents with the compounds of the present invention.

I. Assay for Inhibition of c-Kit in Intact Cells

The ability of compounds to inhibit the tyrosine kinase activity of c-Kit was determined in a cell-based ELISA assay using the H526 cell line (ATCC #CRL-5811), which was originally derived from a human small cell lung cancer. The assay determines the ability of compounds to block ligand-stimulated tyrosine phosphorylation of the wild-type c-Kit receptor protein that is endogenously expressed in H526 cells. Cells are pre-incubated with compounds at various concentrations prior to addition of stem cell factor (SCF), the ligand for the c-Kit receptor tyrosine kinase. Cell lysates are then prepared and the c-Kit protein is captured onto a c-Kit antibody-coated 96-well ELISA plate. The phosphotyrosine content of the receptor protein is then monitored by quantitation of the degree of binding of an antibody that recognizes only the phosphorylated tyrosine residues within the captured protein. The antibody used has a reporter enzyme (e.g. horseradish peroxidase, HRP) covalently attached, such that binding of antibody to phosphorylated c-Kit can be determined quantitatively by incubation with an appropriate HRP substrate.

The stock reagents used are as follows:

Cell Lysis Buffer:
  50 mM Tris-HCl, pH 7.4
  150 mM NaCl
  10% Glycerol
  1% Triton X-100
  0.5 mM EDTA
  1 µg/mL leupeptin
  1 µg/mL aprotinin
  1 mM Sodium orthovanadate Anti c-Kit antibody:
  0.5 µg/mL anti c-Kit Ab-3 (Lab Vision, catalog #MS289P1) in 50 mM Sodium bicarbonate, pH 9.

ELISA Assay plates:
  ELISA assay plates are prepared by addition of 100 µL of anti c-Kit antibody to each well of a 96-well Microlite-2 plate (Dynex, catalog #7417), followed by incubation at 37° C. for 2 h. The wells are then washed twice with 300 µL wash buffer.

Plate Wash Buffer:
  PBS containing 0.5% Tween-20 (PBST)

Cell Assay Medium:
  RPMI with 0.1% BSA pY20-HRP:
  25 ng/mL pY20-HRP (Calbiochem, catalog #525320) in PBS, containing 0.5% Tween-20, 5% BSA, 1 mM Sodium orthovanadate HRP Substrate:
  Chemoluminescent detection reagent (Pierce, catalog #37075)

Assay Protocol:
  Cultures of H526 cells, growing in RPMI with 10% fetal calf serum, were collected by centrifugation, washed twice with PBS, and suspended in cell assay medium. Cells were then distributed into a V-bottom 96-well plate at $7.5 \times 10^4$ cells per well in 100 µL cell assay medium.

Compound dilutions were prepared from 10 mM DMSO stocks by dilution in cell assay medium, the final concentration of DMSO in the assay being 0.1%. To compound incubation wells, 50 µL of the test compound was added (compounds are assayed at concentrations between 0.1 nM and 100 µM); to positive and negative control wells, 50 µL cell assay medium containing 0.1% DMSO was added. The cells were then incubated with compound at 37° C. for 3 h. SCF (R&D Systems, catalog #255-SC-010) was then added in order to stimulate the Kit receptor and induce its tyrosine phosphorylation. Then, 10 µL of a 1.6 µg/mL solution of SCF in cell assay medium was added to all wells apart from the negative control wells, and the cells were incubated for an additional 15 min at 37° C. Following the addition of ice-cold PBS, the plate was centrifuged at 1000 rpm for 5 min, the medium removed by aspiration, and the cell pellet lysed by the addition of 120 µL ice-cold cell lysis buffer per well. The plate was kept on ice for 20 min and 100 µL of the cell lysates from each well were then transferred to the wells of an ELISA assay plate and incubated at 4° C. for 16 h.

Following incubation of the cell lysates in the ELISA plate, the wells were washed 4 times with 300 µL wash buffer, then 100 µL of the phosphotyrosine detection antibody pY20-HRP was added to each well and the plate incubated at rt for 2 h. The wells were then washed 4 times with 300 µL wash buffer. Then, 50 µL of the chemiluminescent HRP substrate was added to each well for luminometric quantitation of the amount of antiphosphotyrosine-HRP conjugate bound to the plate.

Comparison of the assay signals obtained in the presence of compound with those of the positive and negative controls (cells incubated in the presence or absence of SCF, with no compound added), allows the degree of inhibition of c-Kit receptor tyrosine phosphorylation to be determined over a range of compound concentrations. These inhibition values were fitted to a sigmoidal dose-response inhibition curve to determine the $IC_{50}$ values (i.e. the concentration of compound that inhibits SCF-induced tyrosine phosphorylation of the c-Kit protein by 50%).

II. Activated c-Kit Kinase Bench Assay cDNA encoding the c-Kit tyrosine kinase domain was isolated from K562 cells and cloned into a baculovirus expression vector for protein expression in insect cells as a fusion protein with GST (Glutathione S-Transferase). Following purification, the enzyme was incubated with ATP to generate a tyrosine phosphorylated, activated form of the enzyme, which was used in kinase assays to determine the ability of compounds to inhibit phosphorylation of an exogenous substrate by the c-Kit tyrosine kinase domain.

Phosphorylation of c-Kit Protein

The reagents used were as follows:

Column Buffer:
  50 mM HEPES pH 7.4
  125 mM NaCl
  10% Glycerol
  1 mg/mL BSA
  2 mM DTT
  200 µM $NaVO_3$ Phosphorylation Buffer:
  50 mM HEPES pH 7.4
  125 mM NaCl
  24 mM $MCl_2$
  1 mM $MnCl_2$
  1% Glycerol
  200 µM $NaVO_3$
  2 mM DTF
  2 mM ATP 75 µL purified GST-Kit tyrosine kinase protein (approximately 150 µg) is incubated with 225 µL phosphorylation buffer for 1 h at 30° C. In a cold room, a desalting column (e.g. Pharmacia PD-10 column) is equilibrated using 25 mL of column buffer. Phosphorylated protein is applied to the column followed by sufficient column buffer to equal 2.5 mL total (in this case 2.2 mL). The phosphorylated Kit protein is then eluted with 3.5 mL column buffer, and collected into a tube containing 3.5 mL glycerol (final concentration of 50% glycerol). After mixing, aliquots are stored at −20° C. or −70° C.

Kinase activity is determined in an ELISA-based assay that measures the ability of C-Kit to phosphorylate an exogenous substrate (poly Glu:Tyr) on tyrosine residues in the presence of ATP. Substrate phosphorylation is monitored by quantitation of the degree of binding of an antibody that recognizes only the phosphorylated tyrosine residues within the substrate following incubation with c-Kit. The antibody used has a reporter enzyme (e.g. horseradish peroxidase, HRP) covalently attached, such that binding of antibody to the phosphorylated substrate can be determined quantitatively by incubation with an appropriate HRP substrate (e.g. ABTS).

The stock reagents used are as follows:
13.31 µg/mL PGT stock solution: Add 66.7 µL 10 mg/mL PGT to 50 mL PBS.
1× wash buffer: Dilute 20× wash buffer (KPL #50-63-00) to 1× with $H_2O$.
Assay Buffer:
  50 mM Hepes, pH 7.4
  125 mM NaCl
  24 mM $MgCl_2$
  1 mM $MnCl_2$
  1% Glycerol
  200 µM Vanadate—add immediately prior to use
  2 mM DTT—add immediately prior to use
Assay buffer+ATP: Add 5.8 µL of 75 mM ATP to 12 mL of assay buffer.
Activated GST-c-kit(TK): Dilute 1:500 in assay buffer.
Block Buffer:
  PBS containing 0.5% Tween-20, 3% BSA
  200 µM Vanadate—add immediately prior to use
pY20-HRP:
  Add 6.2 µL of a 100 µg/mL stock of pY20-HRP to 10 mL of block buffer
ABTS substrate: KPL 3 50-66-06, use as provided
  Assay Protocol Each well of a 94-well immulon-4 microtitre plate is coated with 75 µL of 13.3 µg/mL PGT stock solution, incubated overnight at 37° C. and washed once with 250 µL 1× wash buffer.

To the negative control wells, 50 µL of assay buffer (without ATP) are added, all other wells contain 50 µL assay buffer +ATP. To positive and negative control wells, 10 µl 5% DMSO is added, other wells contain 10 µL of test compounds (at concentrations between 10 nM and 100 µM) dissolved in 5% DMSO.

30 µL of activated GST-c-Kit are added to initiate the assay, which is incubated at RT for 30 min, and then stopped by the addition of 50 µL/well of 0.5M EDTA. The plate is washed 3× with 1× wash buffer, and then 75 µL of a phospho-tyrosine-specific antibody-HRP conjugate (e.g. pY20-HRP, Calbiochem) in block buffer are added. The plate is incubated at RT for 2 h, and then washed 3× with 1× wash buffer. 100 µL of ABTS substrate are then added, the plate is incubated at rt for 30 min, and the reaction stopped by the addition of 100 µL of 1% SDS. The reaction is quantitated by measuring the OD at 405/490 nM on a microtitre plate reader.

Comparison of the assay signals obtained in the presence of compound with those of controls (in the presence and absence of ATP, with no compound added), allows the degree of inhibition of kinase activity to be determined over a range of compound concentrations. These inhibition values were fitted to a sigmoidal dose-response inhibition curve to determine the IC50 values (i.e. the concentration of compound that inhibits c-Kit protein tyrosine kinase activity by 50%).

The EXAMPLES of this invention either reduced the level of SCF-induced tyrosine phosphorylation of Kit in intact H526 cells as determined in assay I with IC50 values between 10 µM and 0.4 nM, or reduced the ability of Kit to phosphorylate poly(Glu:Tyr) in assay II by at least 50% at 10 µM compound concentrations.

EXPERIMENTAL

The EXAMPLES of the present invention were prepared according to the following procedures by the methods illustrated in the following schemes. Appropriate solvents, temperatures, pressures and other reaction conditions may be readily selected by one of ordinary skill in the art. Similarly, suitable starting materials may be commercially obtained or readily prepared by one skilled in the art.

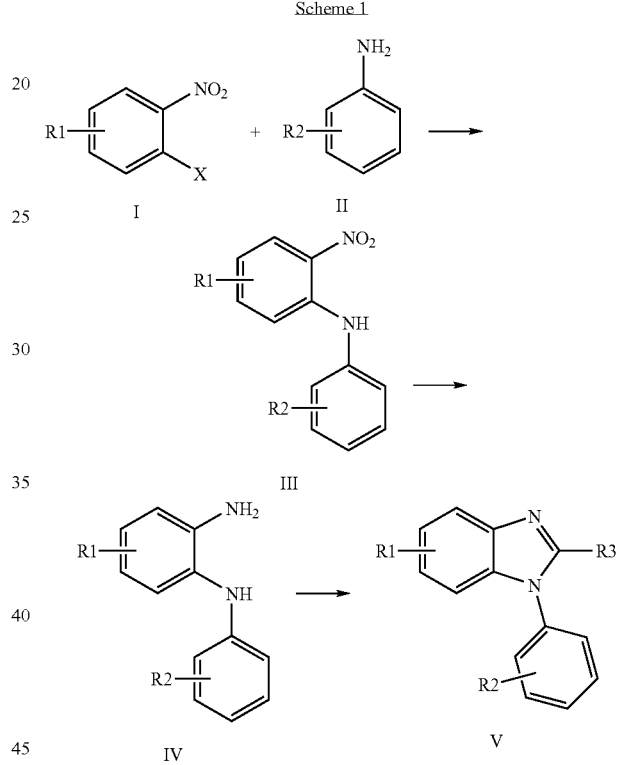

Scheme 1

In Scheme 1, diarylamines (III) may be produced from the condensation of nitrobenzenes (I, X═F, OMs, OTs) with substituted anilines (II). Coupling of the anilines (II) may also be achieved where X═I, Br, Cl, OTf by utilisation of Pd(0) mediated Buchwald-Hartwig-type conditions (such as those described in J. Organic Chem., (1996), 61(21), 7240) or with Cu(I) catalysts and base (e.g. $K_2CO_3$). Reduction of III to give the phenylenediamines (IV) may be achieved using for example, hydrogen in the presence of a suitable transition metal catalyst (palladium, platinum, ruthenium, nickel), iron, zinc or tin under acidic conditions, with sodium hydrosulphite or with tin(II)chloride dihydrate. Cyclisation of IV to the benzimidazoles (V) may be achieved by reaction with a corresponding carboxylic acid, acid halide, acid anhydride or an orthoformate (e.g. $(MeO)_3CH$)) and an acid such as formic or p-toluenesulphonic acid. Under certain conditions used to reduce III e.g. iron powder in formic acid, conversion to the benzimidazoles V may be achieved in one pot. Also, by inclusion of trimethyl orthoformate into a hydrogenation mixture with III, allows the direct conversion to V.

Scheme 2 below shows that formation of N-arylbenzimidazoles (V) may also be accomplished via the process outlined, whereby NIH benzimidazoles (VIII) may be arylated under Pd(0) mediated conditions as disclosed in J. Am. Chem. Soc., (2000), 122, 7600. Separation of the resulting regioisomers may be achieved by a number of means known to those skilled in the art including, but not limited to, chromatographic means or through crystallisation from a suitable solvent. Benzimidazoles (VIII) may be produced from the cyclisation of the anilides (VII) with acids such as, but not limited to, acetic, p-toluenesulphonic, hydrochloric, sulphuric or phosphoric acid. In turn the anilides (VII) can be prepared by reaction of o-phenylenediamines with acid halides or anhydrides or with carboxylic acids in the presence of appropriate coupling reagents known to those skilled in the art such as, but not limited to, EDC, DCC, HOAt, HOBt, HATU, TBTU, or CDI including solid supported versions of these solution phase reagents. Where R3=H, compounds such as VII may be prepared by formylation of VI with alkyl formates (e.g. methyl formate). In the processes described, conversion of VI into VII may also lead to the partial or complete conversion to VIII.

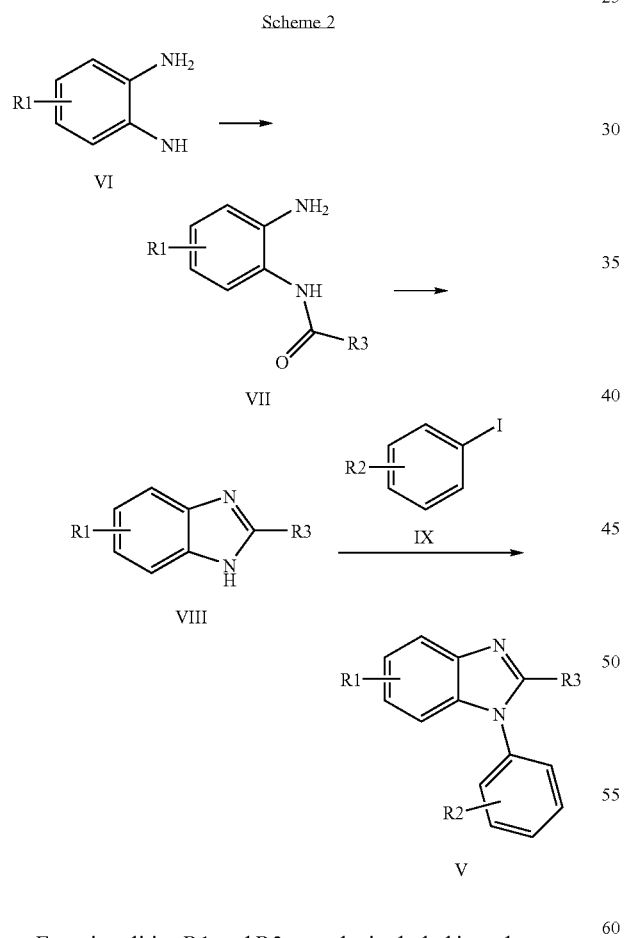

Functionalities R1 and R2, may be included into the target molecules through appropriate choice of starting materials, e.g. of type I, II, VI and IX. Where the final functionality is not available directly through this process, or where such functionality may be compromised during the subsequent chemistry to build the final molecule, alternative functionalities may be used and subsequently transformed into the final desired functionality by methods, and at points in the sequence, readily determined by one skilled in the art.

For example, a non-exhaustive list of such transformations includes the conversions: OMe→OH (BBr$_3$), NH$_2$→Cl (NaNO$_2$, CuCl), Br→CN (Pd$_2$(dba)$_3$, Zn(CN)$_2$, DPPF), Me→CO$_2$H (KMnO$_4$), CO$_2$H→CO$_2$Me (MeOH, H$_2$SO$_4$), OH→OAlkyl (Alkyl halide, base), CO$_2$H→CONR'R" (EDC, HOAt, DIPEA, HNR'R"), Br→CO$_2$Me (Pd$_2$(dba)$_3$, DPPF, CO(g), MeOH), Br→CO$_2$H (tBuLi, CO$_2$), Ar—H→Ar—Br (NBS), CN→CO$_2$H (conc. H$_2$SO$_4$), Br→NR'R" (Pd$_2$(dba)$_3$, DPPF, HNR'R").

Examples of the preparation of the target molecules claimed are shown below in Schemes 3 and 4.

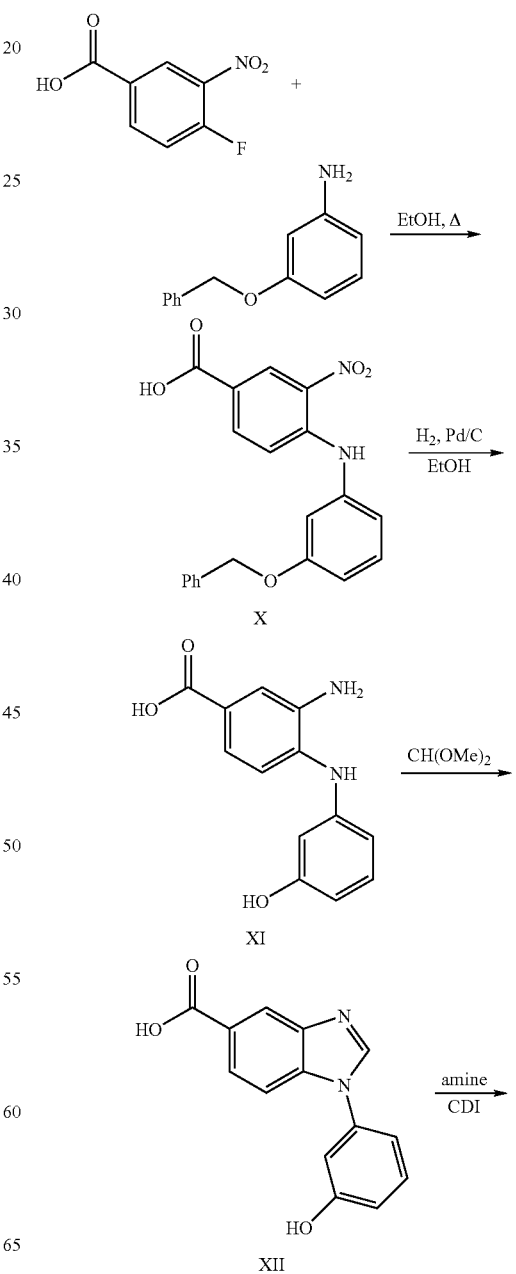

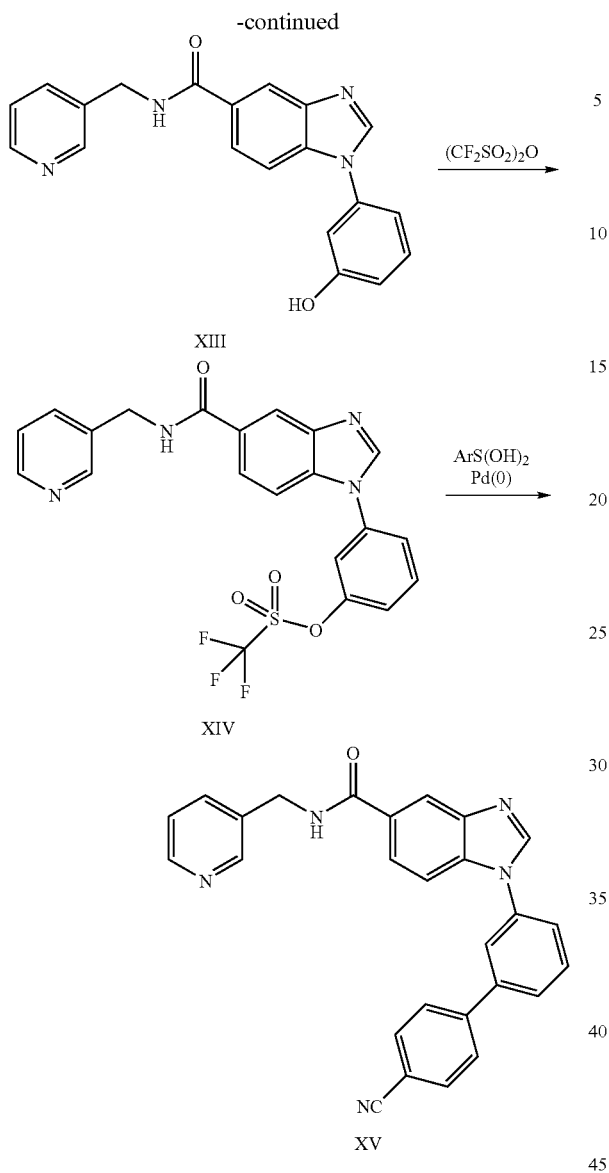
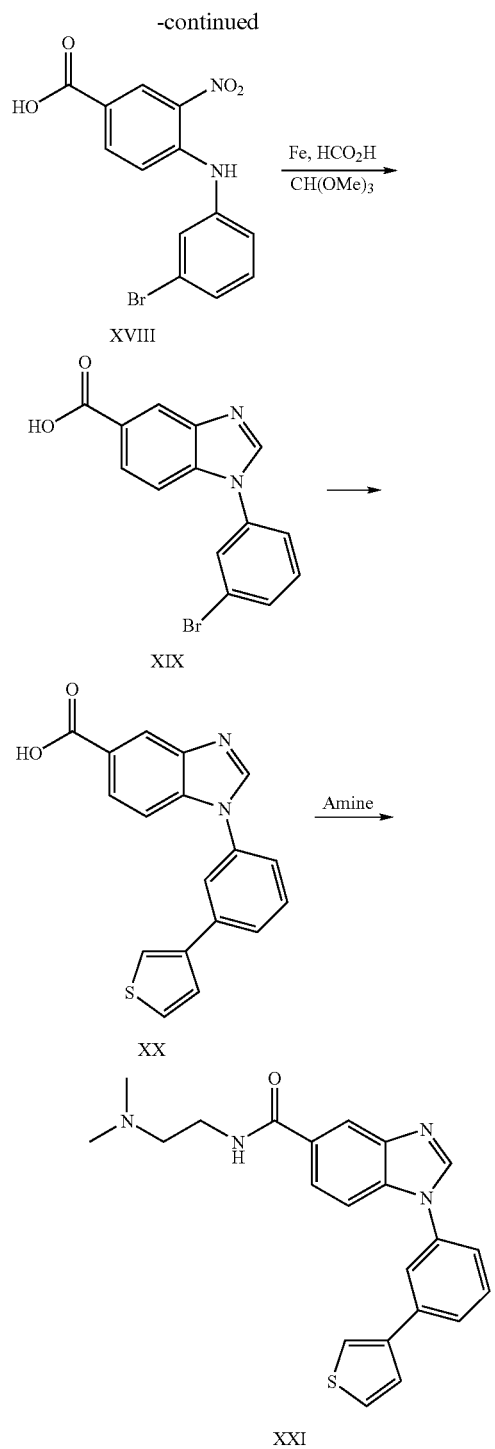

Condensation of 3-benzyloxyaniline with 4-fluoro-3-nitrobenzoic acid occurs through heating in ethanol to give X which may be reduced via catalytic hydrogenation over 10% Pd/C in ethanol to give the phenylenedianine (XI). Cyclisation of XI to the benzimidazole (XII) is achieved by heating with an excess of trimethylorthoformate. 1,1'-Carbonyldiimidazole mediated coupling with 3-pyridinylmethylamine gives amide XIII which can be converted to its triflate with triflic anhydride in the presence of base. This triflate then undergoes Pd(0) mediated coupling with 4-cyanophenylboronic acid to give XV.

Scheme 4

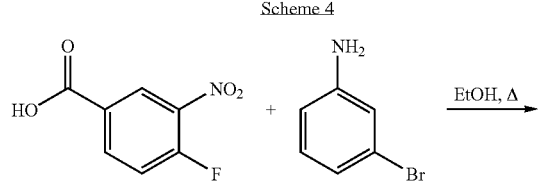

In Scheme 4 benzimidazole XIX is formed by a one-pot reduction-cyclisation procedure using iron in formic acid in the presence of trimethylorthofomate. This bromo derivative may then be coupled with arylboronic acids in the presence of Pd(0) catalysts as described above to generate intermediate biaryl molecules such as XX which in turn may be coupled with amines such as 2-(N,N-dimethylamino)ethylamine in the presence of reagents such as EDC and HOBt to provide the target molecules claimed such a XXI.

Definitions: EDC=ethyl dimethylaminopropylcarbodiimide hydrochloride, HOAt=1-hydroxyazabenzotriazole, HOBt=1-hydroxybenzotriazole, CDI=1,1'-carbonyldiimidazole, TBTU=O-benzotriazole-N,N,N',N'-tetramethyl uronium tetrafluoroborate, HATU=azabenzotriazolyl-N,N,N',N',-tetramethyluronium hexafluorophosphate, DIPEA=diisopropylethylamine, TEA=triethylamine, DMF=N,N-dimethylformamide, NMP=N-methylpyrrolidinone, DCM=dichloromethane, DMAP=4-dimethylaminopyridine, TFA=trifluoroacetic acid, Boc=tbutoxycarbonyl, Fmoc=fluorenylmethyloxycarbonyl, DMSO=dimethylsulphoxide, AcOH=acetic acid, OMs=$OSO_2Me$, OTs=$OSO_2$-(4-Me)Ph, OTf=$OSO_2CF_3$, DPPF=, $Pd_2(dba)_3$, NBS=N-bromosuccimimide, HCl (aq)= aqueous hydrochloric acid, DMA=N,N-dimethylacetamide, MeOH=methanol, EtOH=ethanol, HOAc=acetic acid, EtOAc=ethyl acetate, THF=tetrahydrofuran, hplc=high performance liquid chromatography, PS-TFP=polystyrene-supported tetrafluorophenol resin, PS-HOBt=polystyrene-supported 1-hydroxybenzotriazole resin, DIC=1,3-diisopropylcarbodiimide, IMS=industrial methylated spirit, NMM=N-methyl morpholine, Pd/C=palladium on carbon, $Pd(PPh_3)_4$=tetrakis(triphenylphosphine)palladium (0), $Cs_2CO_3$=cesium carbonate, $Pd_2(dba)_3$=tris(dibenzylideneacetone)dipalladium (0), BINAP=1,1'-binaphthyl, $Pd(OAc)_2$= palladium (II) acetate, $K_2CO_3$=potassium carbonate, MeCN=acetonitrile, DCC=1,3-dicyclohexylcarbodiimide, HPLC=high performance liquid chromatography, rt or r.t.=room temperature, MTP=microtitre plate, rin=minute(s), h=hour(s), d=day(s).

General Procedures for the Preparation of N-Substituted Benzimidazoles:

a) 4-Fluoro-3-nitrobenzoic acid (25.58 g, 138 mmol) and an aniline (138 mmol) were dissolved in ethanol (400 mL) and the mixture was heated at reflux under $N_2$ atmosphere for 16 h. On cooling to rt the resulting yellow/orange precipitate was isolated by filtration and washed with methanol to provide the 4-anilino-3-nitrobenzoic acid e.g. 4-{[3-bromophenyl]amino}-3-nitrobenzoic acid.

b) This crude intermediate was then dissolved in acetic acid (366 mL) and trimethyl orthoformate (232 mL) and iron powder (<10 micron, 21.5 g, 384 mmol) was added causing a modest exotherm. The resulting mixture was stirred at rt under a $N_2$ atmosphere for 16 h, after which the excess iron and associated oxides were removed by filtration and washed with $CH_2Cl_2$. The filtrate was concentrated and the resulting material triturated with methanol to give the N-arylbenzimidazole carboxylic acid e.g. 1-(3-Bromophenyl)-1H-benzimidazole-5-carboxylic acid. 1H NMR (DMSO-d6, 400 MHz): δ 7.61 (dd, 1H, J=8.4, 8.4 Hz), 7.71 (dd, 1H, J=8.4, 8.4 Hz), 7.73-7.78 (m, 2H), 7.96 (dd, 1H, J=8.8, 1.6Hz), 8.00 (dd, 1H, J=1.6, 1.6 Hz), 8.33 (d, 1H, J=0.8 Hz) and 8.74 (s, 1H); MS (ES+): m/z 317 [Br79MH+], 319 [Br81MH+].

c) A mixture of the N-arylbenzimidazole carboxylic acid (19.7 mmol), EDC (5.64 g, 29.5 mmol) and DMAP (0.24 g, 1.97 mmol) in DMF (100 mL) was treated with 3-aminomethylpyridine (3.19 g, 29.5 mmol) and the mixture stirred at rt for 16 h. The DMF was then removed in vacuo and the residue dissolved in DCM (150 mL) and the resulting solution washed with water (3×50 mL). The organic phase was dried ($MgSO_4$) and concentrated in vacuo and the crude product chromatographed over silica gel eluting with 1-10% MeOH/DCM. The material thus isolated was further purified by crystallisation to give the N-arylbenzimidazole carboxamide e.g. 1-(3-Bromophenyl)-N-pyridin-3-ylmethyl-1H-benzimidazole-5-carboxamide. 1H NMR (1:1 DMSO-d6: CDCl3, 400 MHz): δ 4.64 (d, 2H, J=5.9 Hz), 7.29 (dd, 1H, J=7.8, 4.8 Hz), 7.51-7.60 (m, 3H), 7.65 (ddd, 1H, J=7.5, 1.7.7, 1.7 Hz), 7.75 (dd, 1H, J=1.7, 1.7 Hz), 7.78 (ddd, 1H, J=7.9, 1.8, 1.8 Hz), 7.99 (dd, 1H, J=8.6, 1.5 Hz), 8.29 (s, 1H), 8.46 (d, 1H, J=1.2Hz), 8.49 (dd, 1H, J=4.8, 1.4Hz), 8.65 (d, 1H, J=1.7 Hz), 8.85 (t, 1H, J=5.8 Hz); MS (ES+): m/z 407 [Br79MH+], 409 [Br81MH+].

Alternatively:

a) 4-Fluoro-3-nitrobenzoic acid (21.6 mmol) and an aniline (43.2 mmol) in 15 mL of ethanol were stirred at reflux under argon for 5 h resulting in the formation of an orange precipitate. After 12 h the heterogeneous reaction mixture was poured into 50 mL of 1N HCl(aq) and diluted with 100 mL of water. The solution was stirred for 20 min then the precipitate filtered to yield the 4-anilino-3-nitrobenzoic Acid: e.g. 4-{[3-(benzyloxy)phenyl]amino}-3-nitrobenzoic acid.

b) A solution of the 4-anilino-3-nitrobenzoic acid (20.1 mmol) in THF (100 mL) was charged with 10% Pd/C (500 mg) and the reaction flask evacuated and subsequently charged with $H_2$ (g) three times. The mixture was stirred vigorously for 12 h after which time it was filtered through diatomaceous earth and the filtrate concentrated in vacuo to give the desired 3-amino-4-anilinobenzoic acid: e.g. 3-amino4-[(3-hydroxyphenyl)amino]benzoic acid.

c) A solution of the 3-amino-4-anilinobenzoic acid (20.1 mmol) in formic acid (40 mL) was charged with trimethylorthoformate (2.4 mL, 22.0 mmol) and heated at reflux for 3 h after which time the mixture was allowed to cool to rt and stirred for 12 h. The reaction mixture was then poured into 150 mL of $H_2O$ and stirred for 20 min yielding a precipitate which was isolated by filtration to give the 1-aryl-1H-benzimidazole-5-carboxylic acid: e.g. 1-(3-hydroxyphenyl)-1H-benzimidazole-5-carboxylic acid.

d) A solution of the 1-aryl-1H-benzimidazole-5-carboxylic acid (0.39 mmol) in DMF (5 mL) was treated with CDI (95 mg, 0.58 mmol) and stirred for 15 min resulting in the formation of a white precipitate. A primary or secondary amine (0.78 mmol) was then added and the mixture was stirred overnight prior to being poured into 75 mL $H_2O$ and any solid subsequently formed, isolated by filtration to give the 1-aryl-N-(substituted)-1H-benzimidazole-5-carboxamide. Where the desired product did not precipitate from the reaction solution or during the work up, it was isolated by addition of water, extraction into organic solvent (typically EtOAc), drying and concentration of the extracts, and the residue then purified by preparative HPLC or by normal phase chromatography over silica gel.

EXAMPLE R1

1-(4'-Cyano-1,1'-biphenyl-3-yl)-N-pyridin-3-ylmethyl-1H-benzimidazole-5-carboxamide A flask containing a mixture of 1-(3-bromophenyl)-N-pyridin-3-ylmethyl-1H-benzimidazole-5-carboxamide (prepared according to the general procedures described above, 80 mg, 0.20 mmol) and 4-cyanophenylboronic acid (57 mg, 0.39 mmol) was evacuated and refilled with $N_2$ (2×). To this was added $Pd(PPh_3)_4$ (34 mg, 0.029 mmol) in one portion with minimum exposure to air. The flask was again evacuated and refilled with $N_2$ (3×). Degassed solutions of DME-EtOH (4:1 v/v, 2 mL) and aq $Na_2CO_3$ (2M, 0.6 mL) were added via syringe and the solution was stirred under N2 for 10 min at rt and then at 85° C. for 19 h. The reaction was then cooled to rt, filtered, and purified using the Waters mass-directed HPLC purification system. Further recrystallization from acetonitrile yielded 1-(4'-cyano-1,1'-biphenyl-3-yl)-N-pyridin-3-ylmethyl-1H-benzimidazole-5-carboxamide as a white solid (18.5 mg, 22% yield). MS (ES+): m/z430 (100) [MH+]. 1H NMR (400 MHz, CD3OD): δ=8.66 (s, 1H), 8.61 (d, J=2.4Hz, 1H), 8.45 (dd, J=4.8 Hz, 1.2 Hz, 1H), 8.34 (dd, J=1.0 Hz, 0.4 Hz, 1H), 7.99 (t, J=1.6 Hz, 1H), 7.88-7.86 (m, 3H), 7.86-7.82 (m, 4H), 7.80 (t, J=8.0 Hz, 1H), 7.74 (d, J=8.8 Hz, 2H), 7.43 (dd, J=8.4 Hz, 5.2 Hz, 1H), 7.67 (s, 2H).

The following compounds were prepared according to the procedure described above for EXAMPLE R1 utilising the appropriate boronic acid derivatives.

EXAMPLE R2

N-(Pyridin-3-ylmethyl)-1-(3-thien-3-ylphenyl)-1H-benzimidazole-5-carboxamide

MS (ES+): m/z 411 [MH$^+$].

EXAMPLE R3

N-(Pyridin-3-ylmethyl)-1-[3-(1H-pyrrol-2-yl)phenyl]-1H-benzimidazole-5-carboxamide MS (ES+): m/z 394 (100) [MH+].

EXAMPLE R4

1-(3'-Chloro-4'-fluoro-1,1'-biphenyl-3-yl)-N-(pyridin-3-ylmethyl)-1H-benzimidazole-5-carboxamide MS (ES+): m/z 457 (100) [MH+].

EXAMPLE R5

1-(3'-Cyano-1,1'-biphenyl-3-yl)-N-(pyridin-3-ylmethyl)-1H-benzimidazole-5-carboxamide MS (ES+): m/z 430 (100) [MH+].

EXAMPLE R6

1-(3'-Nitro-1,1'-biphenyl-3-yl)-N-(pyridin-3-ylmethyl)-1H-benzimidazole-5-carboxamide MS (ES+): m/z 449 (100) [MH+].

EXAMPLE R7

N-(Pyridin-3-ylmethyl)-1-(3-pyridin-3-ylphenyl)-1H-benzimidazole-5-carboxamide

MS (ES+): m/z 406 (100) [MH+].

EXAMPLE R8

1-[3-(1-Benzyl-1H-pyrazol-4-yl)phenyl]-N-(pyridin-3-ylmethyl)-1H-benzimidazole-5-carboxamide MS (ES+): m/z 485 (100) [MH+].

EXAMPLE R9

N-(Pyridin-3-ylmethyl)-1-[3-(1H-pyrrol-3-yl)phenyl]-1H-benzimidazole-5-carboxamide t-BuLi (1.7M, 0.60 mL, 1.0 mmol) was added dropwise to a solution of 3-bromo-1-triisopropylsilanyl-1H-pyrrole (144 mg, 0.476 mmol) in THF (2 mL) at −78° C. The reaction mixture was stirred for 40 min at that temperature before B(OMe)$_3$ (0.27 mL, 2.38 mmol) was added to it rapidly. The reaction was stirred for 19 min at −78° C. and then the cooling bath was removed. After reaching rt the reaction mixture was concentrated under reduced pressure to afford crude boron intermediate as a white solid to which was added 1-(3-bromophenyl)-N-pyridin-3-ylmethyl-1H-benzimidazole-5-carboxamide (86 mg), DME (3.5 mL), 2M aq Na$_2$CO$_3$ (1.0 mL). The mixture was purged by passing a slow stream N$_2$. Pd(PPh$_3$)$_4$ (56 mg, 0.048 mmol) was added quickly with minimum exposure to air. The mixture was purged again by passing a slow stream N$_2$ before it was heated at reflux for 18 h under N$_2$ then cooled to rt, filtered through Celite, concentrated under reduced pressure and purified by column chromatography (SiO$_2$, 0 to 9% MeOH in CH$_2$Cl$_2$). The material was recrystallized (CH$_3$CN) to provide the title compound as a white solid. MS (ES+): m/z 394.44 (100) [MH$^+$].

EXAMPLE R10

1-[3-(1-methyl-1H-pyrrol-2-yl)phenyl]-N-(Pyridin-3-ylmethyl)-1H-benzimidazole-5-carboxamide A mixture of 1-(3-bromophenyl)-N-pyridin-3-ylmethyl-1H-benzimidazole-5-carboxamide (85 mg, 0.209 mmol), Pd(PPh$_3$)$_2$Cl$_2$ (28 mg, 0.040 mmol) and Ag$_2$O (45 mg, 0.196 mmol) was added in one portion to a flask charged with 1-methyl-2-tributylstannanyl-1H-pyrrole (0.391 g, 1.06 mmol). The flask was evacuated and backfilled with N$_2$ (2×) then charged with anhydrous DMF (3.0 mL). After stirring at rt for 5 min the reaction mixture was heated to 90° C. under N$_2$ for 2 d. Later, the reaction was cooled to rt and treated with 1 M aq KF (3 mL) and stirred overnight at rt. Then filtered through Celite (using MeOH to rinse the Celite) and purified by MDPS to provide the product as a white solid. MS (ES+): m/z 408.46 (100) [MH$^+$].

EXAMPLE R11

1-(2'-Nitro-1,1'-biphenyl-3-yl)-N-(pyridin-3-ylmethyl)-1H-benzimidazole-5-carboxamide was prepared according to the procedure described above for EXAMPLE R1 utilising 2-nitrophenylboronic acid. MS (ES+): m/z 450 (100) [MH+].

EXAMPLE R12

N-(Pyridin-3-ylmethyl)-1-[3-(1,3-thiazol-2-yl)phenyl-1H-benzimidazole-5-carboxamide A flask containing a mixture of 1-(3-bromophenyl)-N-pyridin-3-ylmethyl-1H-benzimidazole-5-carboxamide (80 mg, 0.196 mmol, 4049-79-2), Pd(PPh$_3$)$_2$Cl$_2$ (16 mg, 0.0196 mmol) and Ag$_2$O (45 mg, 0.196 mmol) was evacuated and backfilled with N$_2$ (2×) and charged with anhydrous DMF (0.5 mL). 2-Tributylstannanylthiazole (367 mg, 0.306 mmol) was added via syringe from a vial that was later rinsed with two portions of DMF (2×0.75 mL), each portion was added to the reaction mixture. After stirring at rt for 5 min the reaction mixture was heated to 100° C. under N$_2$ for 21 h. Later, the reaction was cooled to rt, diluted with MeOH to ~50 mL, treated with 1M aq KF (4 mL) and stirred overnight at rt. Then filtered through Celite (using MeOH to rinse the Celite) purified by preparative TLC (9:1 DCM:MeOH) to obtain crude

EXAMPLE R13

N-Methyl-1-(3-thien-3-ylphenyl)-1H-benzimidazole-5-carboxamide

MS (ES+): 334.1 (100%) [MH+].

EXAMPLE R14

N-Methyl-1-[3-(1H-pyrrol-2-yl)phenyl]-1H-benzimidazole-5-carboxamide

MS (ES+): m/z 317.2 (100%) [MH+].

EXAMPLE R15

N-Ethyl-1-(3-thien-3-ylphenyl)-1H-benzimidazole-5-carboxamide

MS (ES+): m/z 348.1 (100%) [MH+].

EXAMPLE R16

N-Ethyl-1-[3-(1H-pyrrol-2-yl)phenyl]-1H-benzimidazole-5-carboxamide

MS (ES+): m/z 331.2 (100%) [MH+].

EXAMPLE R17

N-methyl-1-(3-pyridin-3-ylphenyl)-1H-benzimidazole-5-carboxamide

MS (ES+): m/z 329.2 (100%) [MH+].

EXAMPLE R18

N-[2-Dimethylamino)ethyl]-1-(3-thien-3-ylphenyl)-1H-benzimidazole-5-carboxamide

MS (ES+): m/z 391.2 (100%) [MH+].

EXAMPLE R19

1-[3'-(Acetylamino)-1,1'-biphenyl-3-yl]-N-methyl-1H-benzimidazole-5-carboxamide

MS (ES+): m/z 385.1 (100%) [MH+].

EXAMPLE R20

1-(3'-Chloro-4'-fluoro-1,1'-biphenyl-3-yl)-N-methyl-1H-benzimidazole-5-carboxamide MS (ES+): m/z 380.1(100%) [MH+].

EXAMPLE R21

1-[3-(1,3-Benzodioxol-5-yl)phenyl]-N-methyl-1H-benzimidazole-5-carboxamide

MS (ES+): m/z 372.1 (100%) [MH+].

EXAMPLE R22

1-(1,1'-Biphenyl-3-yl)-N-methyl-1H-benzimidazole-5-carboxamide

MS (ES+): m/z 404.2 (100%) [MH+].

EXAMPLE R23

N-Methyl-1-(2'-phenoxy-1,1'-biphenyl-3-yl)-1H-benzimidazole-5-carboxamide

MS (ES+): m/z 420.1 (100%) [MH+].

EXAMPLE R24

1-[3-(2,3-Dihydro-1-benzofuran-5-yl)phenyl]-N-methyl-1H-benzimdazole-5-carboxamide MS (ES+): m/z 370.1 (100%) [MH+].

EXAMPLE R25

N-Methyl-1-{3'-[(methylsulfonyl)amino]-1,1'-biphenyl-3-yl}-1H-benzimidazole-5-carboxamide MS (ES+): m/z 421.1 (100%) [MH+].

EXAMPLE R26

1-[3-(5-Chlorothien-2-yl)phenyl]-N-methyl-1H-benzimidazole-5-carboxamide

MS (ES+): m/z 367.9 (100%) [MH+].

EXAMPLE R27

N-Methyl-1-(3-thien-2-ylphenyl)-1H-benzimidazole-5-carboxamide

To a solution of 1-(3-bromophenyl)-N-methyl-1H-benzimidazole-5-carboxamide (20 mg, 0.06 mmol) and thiophene-2-boronic acid (9.0 mg. 0.073 mmol) in anhydrous DMF (0.6 mL) was added Pd(PPh$_3$)$_4$ (3.5 mg, 0.003 mmol) followed by a solution of Na$_2$CO$_3$ (19 mg, 0.18 mmol) in water (0.16 mL). The reaction was irradiated in the microwave for 10 min (200 W, 150° C.). After cooling, the reaction mixture was filtered through Celite and washed with EtOAc (15 mL). The combined organic layer was washed with saturated aqueous NaHCO$_3$ solution (10 mL) followed by saturated aqueous solution brine (3×10 mL), dried (MgSO$_4$) and evaporated to dryness. The crude product was purified by solid-phase extraction (Isolute SAX, followed by Isolute SCX), giving N-methyl-1-(3-thien-2-ylphenyl)-1H-benzimidazole-5-carboxamide as an off-white solid; 1H NMR (400 MHz, MeOH-d4): δ 8.57 (s, 1H), 8.27 (d, J=2 Hz, 1H), 7.89-7.86 (m, 2H), 7.78 (d, J=7.8 Hz, 1H), 7.66-7.62 (m, 2H), 7.52-7.54 (m, 2H), 7.45 (d, J=5.1 Hz, 1H), 7.12 (dd, J=3.5 Hz, 1.5 Hz, 1H), 2.97 (s, 3H); MS (ES+): m/z 333.9 (100%) [MH+].

material which was purified by MDPS to provide the product as a white solid. MS (ES+): m/z 412.31 (100) [MH+].

EXAMPLE R28

1-(1,1'-Biphenyl-3-yl)-N-methyl-1H-benzimidazole-5-carboxamide

MS (ES+): m/z 327.9 (100%) [MH$^+$].

EXAMPLE R29

N-Methyl-1-(4'-methyl-1,1'-biphenyl-3-yl)-1H-benzimidazole-5-carboxamide

MS (ES+): m/z 342.0 (100%) [MH$^+$].

EXAMPLE R30

1-(3'-Fluoro-1,1'-biphenyl-3-yl)-N-methyl-1H-benzimidazole-5-carboxamide

MS (ES+): m/z 345.9 (100%) [MH$^+$].

EXAMPLE R31

1-(3-Thien-3-ylphenyl)-1H-benzimidazole-5-carboxamide

MS (ES+): m/z 320.0 (100%) [MH$^+$].

EXAMPLE R32

N-(tert-Butyl)-1-(3-thien-3-ylphenyl)-1H-benzimidazole-5-carboxamide

MS (ES+): m/z 376.1 (100%) [MH$^+$].

EXAMPLE R33

1-[3-(3,5-Dimethylisoxazol-4-yl)phenyl]-N-methyl-1H-benzimidazole-5-carboxamide

MS (ES+): m/z 347.2 (100%) [MH$^+$].

EXAMPLE R34

1-[3-(3,5-Dimethylisoxazol-4-yl)phenyl]-N-ethyl-1H-benzimidazole-5-carboxamide

MS (ES+): m/z 361.2 (100%) [MH$^+$].

EXAMPLE R35

N-[2-(Dimethylamino)ethyl]-1-[3-(3,5-dimethylisoxazol-4-yl)phenyl]-1H-benzimidazole-5-carboxamide MS (ES+): m/z 404.2 (100%) [MH$^+$].

EXAMPLE R36

1-[3-(3,5-Dimethylisoxazol-4-yl)phenyl]-N-tetrahydro-2H-pyran-4-yl-1H-benzimidazole-5-carboxamide MS (ES+): m/z 417.2 (100%) [MH$^+$].

EXAMPLE R37

N-Tetrahydro-2H-pyran-4-yl-1-(3-thien-3-ylphenyl)-1H-benzimidazole-5-carboxamide MS (ES+): m/z 404.1 (100%) [MH$^+$].

EXAMPLE R38

N-Tetrahydro-2H-pyran-4-yl-1-(3-pyrrol-2-ylphenyl)-1H-benzimidazole-5-carboxamide MS (ES+): m/z 387.2 (100%) [MH$^+$].

EXAMPLE R39

N-Methyl-1-[3-(2-naphthyl)phenyl]-1H-benzimidazole-5-carboxamide

MS (ES+): m/z 378.1 (100%) [MH$^+$].

EXAMPLE R40

N-Methyl-1-[4'-(methylsulfonyl)-1,1'-biphenyl-3-yl]-1H-benzimidazole-5-carboxamide MS (ES+): m/z 406.1 (100%) [ME$^+$].

EXAMPLE R41

1-[3-(1-Benzothien-2-yl)phenyl]-N-methyl-1H-benzimidazole-5-carboxamide

MS (ES+): m/z 383.9 (100%) [MH+].

EXAMPLE R42

N-[2-(Dimethylamino)ethyl]-1-(3-pyrrol-2-ylphenyl)-1H-benzimidazole-5-carboxamide MS (ES+): m/z 374.2 (100%) [MH$^+$].

EXAMPLE R43

N-(Pyridin-3-ylmethyl)-1-[3-(1H-pyrrol-1-yl)phenyl]-1H-benzimidazole-5-carboxamide MS (ES+): m/z 394.4 (100%) [MH$^+$].

EXAMPLE R44

N-(1,3-Benzodioxol-5-ylmethyl)-1-[3-(1H-pyrrol-1-yl)phenyl]-1H-benzimidazole-5-carboxamide MS (ES+): m/z 437.4 (100%) [MH$^+$].

Combinatory Library and Process

The EXAMPLES of the combinatory library of the present invention were prepared according to the polymer-assisted solution phase synthesis (resin 'capture and release') methods illustrated in the following schemes. Appropriate solvents, temperatures, pressures and other reaction conditions may be readily selected by one of ordinary skill in the art. Similarly, suitable starting materials may be commercially obtained or readily prepared by one skilled in the art.

Scheme C1

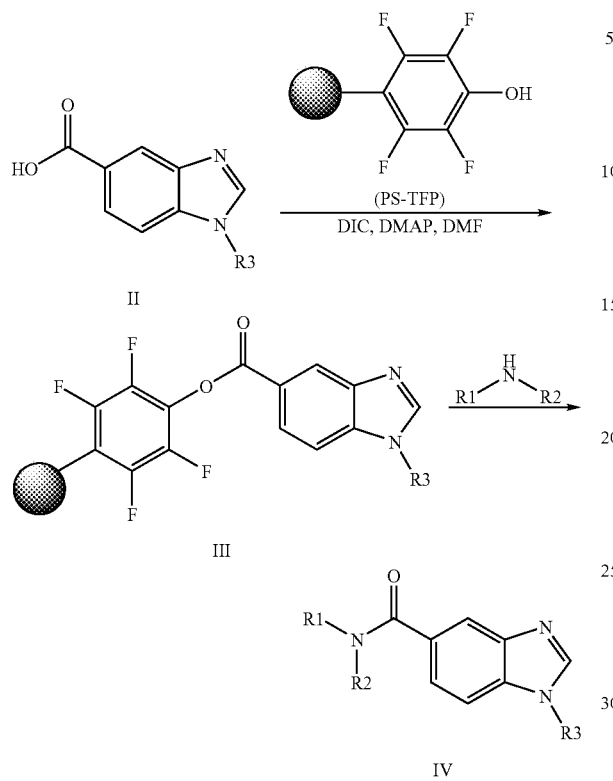

II

III

IV

In Scheme C1, N1-substituted benzimidazole-5-carboxamides (IV) may be produced from the attachment of N1-substituted benzimidazole-5-carboxylic acids (II) to commercially available polystyrene-supported tetrafluorophenol resin (PS-TFP) (Salvino, J. W. et al. *J. Comb. Chem.* 2000, 2, 691-697) by use of conventional condensation reagents. DIC with DMAP is the preferred coupling reagent combination. Other polymer-supported reagents which provide stable active esters, such as polymer-supported 1-hydroxybenzotriazole (PS-HOBt) and polymer-supported nitrophenols, are alternative resins that might be used in place of PS-TFP.

Resin loading may typically be estimated by weight gain, although $^{19}$F NMR can also be employed to provide a more accurate determination of the efficiency of loading. Typically loadings of >80% may be achieved. These resin-bound activated esters are relatively stable and may be stored in the fridge under an inert atmosphere.

Reaction of the polymer-supported benzimidazole carboxylic acid (III) with limiting amounts of primary and secondary amines typically ensures a single, clean reaction product, the desired benzimidazoles (IV). The effectiveness of release of the product is dependent on the nucleophilicity of the amine and as a result cleavage reactions may be run over extended reaction times.

The benzimidazole acids (II) required as building blocks for the process may be prepared by a number of methods, including but not limited to those described above in Schemes 1, 2, and 3, as well as the Schemes described below. Examples of the preparation of representative members of the target libraries using the process described are shown below in Schemes C4 to C7.

Scheme C4

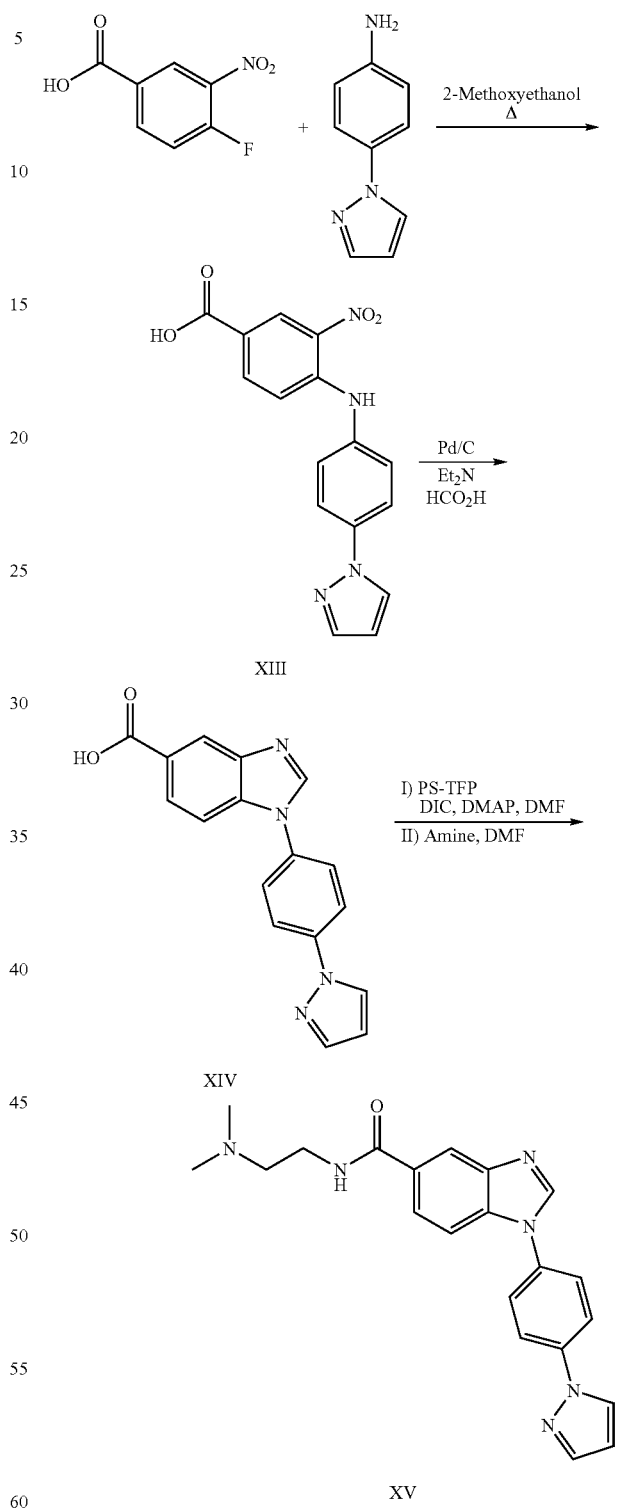

XIII

XIV

XV

4-Pyrazolyl-aniline may be heated with 4-fluoro-3-nitrobenzoic acid in 2-methoxyethanol to give (XIII) which undergoes reductive cyclisation using 10% Pd/C in triethylamine with formic acid to give the benzimidazole (XIV). DIC/DMAP-mediated loading of the resultant benzimidazole carboxylic acid (XIV) onto PS-TFP provided the supported benzimidazole acid, which is cleaved with a range of amines to provide the corresponding benzimidazole carboxamides. The example shown gives benzimidazole (XV) by use of N,N-dimethylethyenediamine as the cleaving amine.

mides. The example shown gives benzimidazole (XVIII) by using isonipecotamide as the cleaving amine.

The intermediate bromo benzimidazoles such as (XVII) may be further transformed by a variety of metal-catalysed coupling procedures to provide for example biaryl, aryl-heteroaryl or arylamine benzimidazole carboxylic acids, examples of which are shown in Schemes 6 & 7. Whilst metal-catalysed arylations proceed effectively on the benzimidazole acids, the corresponding benzimidazole methyl esters are preferred for metal-catalysed aminations. The derivatised benzimidazole carboxylic acids may be loaded onto PS-TFP and subsequently cleaved with a range of amines to provide the corresponding benzimidazole carboxamides. In the examples shown, cleavage of the respective resin-bound acids with 4-aminotetrahydropyran gave benzimidazole (XX) or with ethylamine gave benzimidazoles (XXIV) and (XXVI).

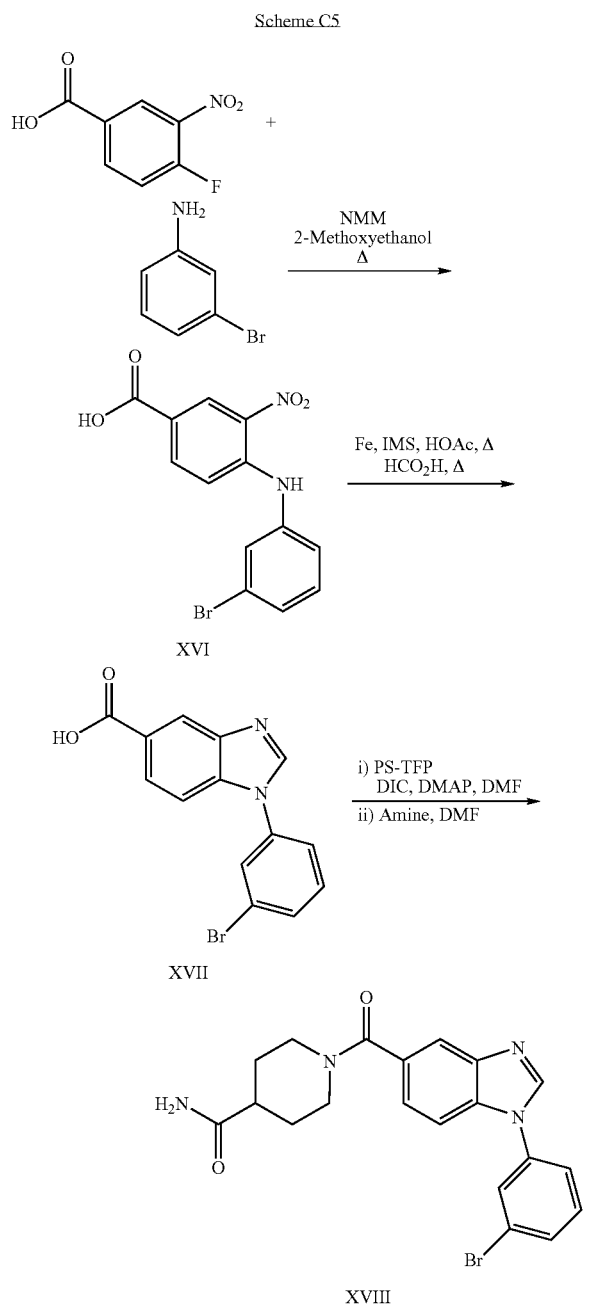

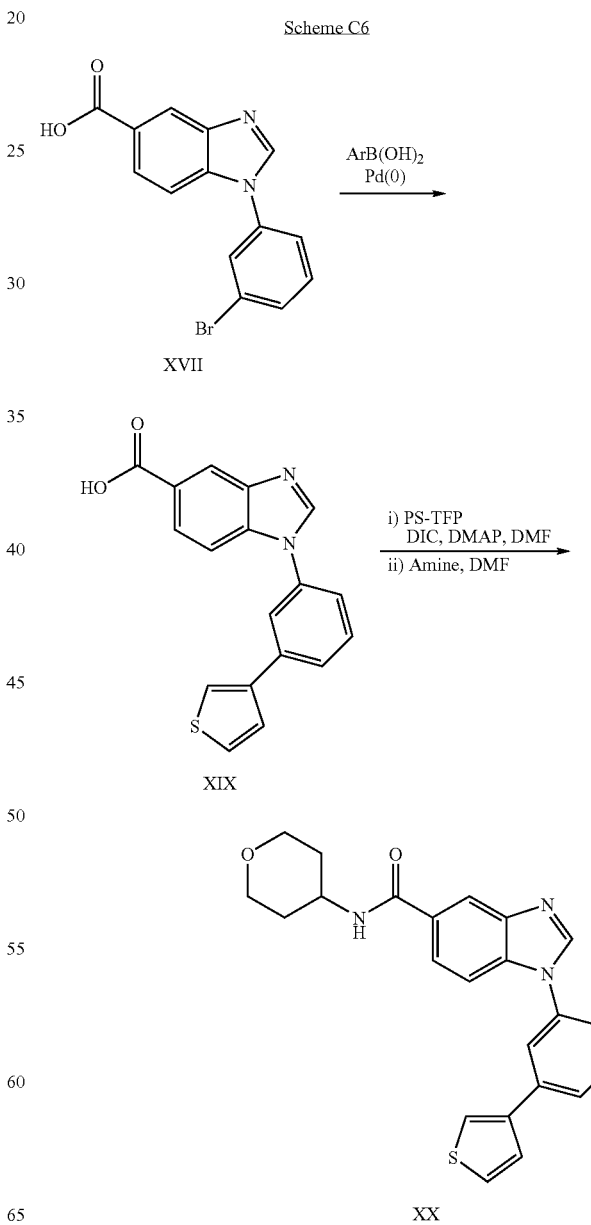

Condensation of 3-bromoaniline with 4-fluoro-3-nitrobenzoic acid occurs through heating with NMM in 2-methoxyethanol to give (XVI) which may react by a one-pot reduction-cyclisation procedure, using iron/acetic acid in IMS followed by formic acid, to give the benzimidazole (XVII). DIC/DMAP-mediated loading of the resultant benzimidazole carboxylic acid (XVII) onto PS-TFP provides the supported benzimidazole acid, which may be cleaved with a range of amines to provide the corresponding benzimidazole carboxa-

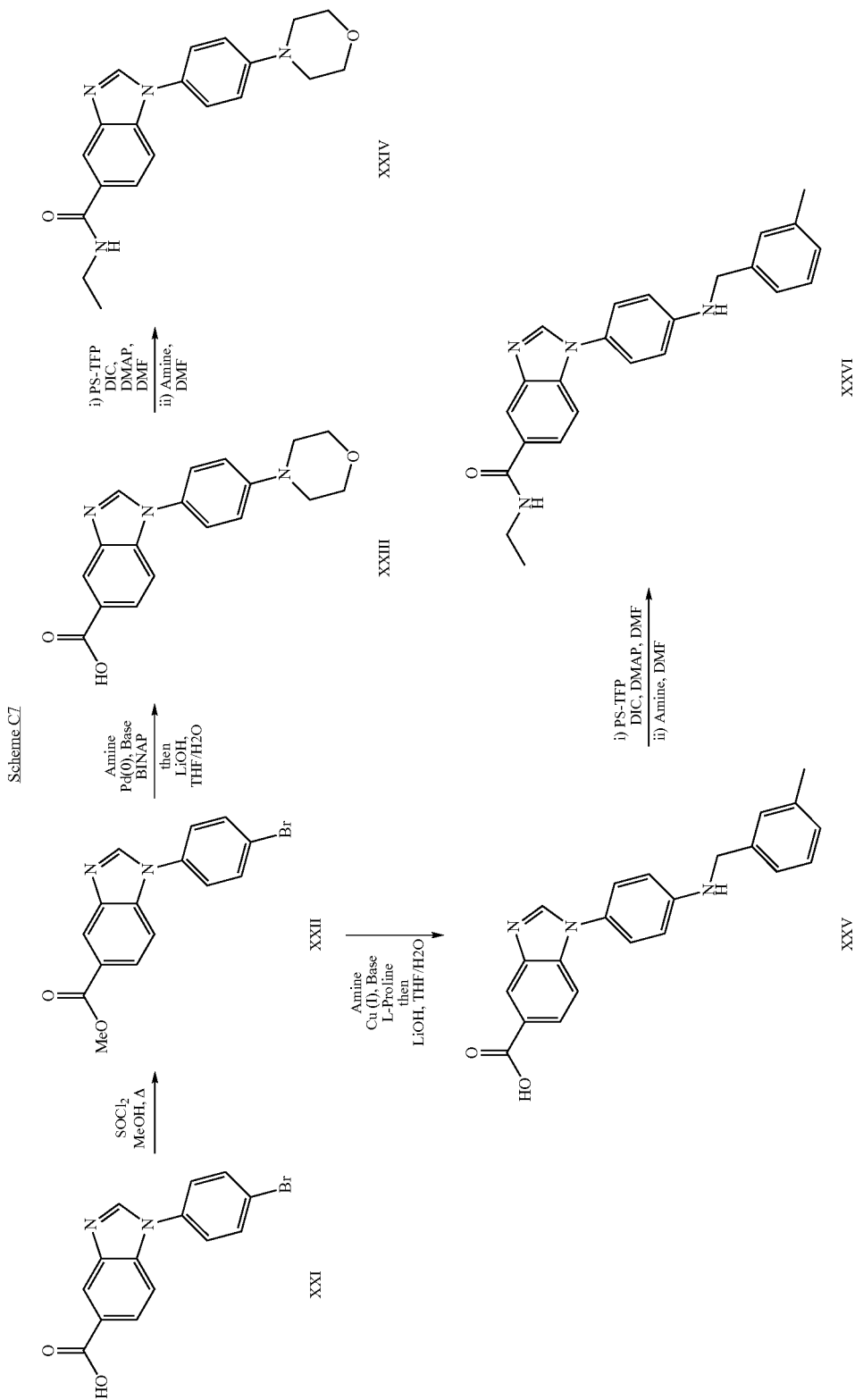

General Procedures for the Preparation of Ni-Substituted Benzimidazole-5-carboxylic Acids a) 4-Fluoro-3-nitrobenzoic acid (0.27 mol), an aniline (0.32 mol) and NMM (32.5 mL) in 2-methoxyethanol (750 mL) were stirred at reflux under argon for 24 h. The suspension was concentrated under reduced pressure and the residue was sonicated with 1M HCl (aq) over 1.5 h. The resultant orange solid was isolated by filtration, washed with water dried, then sonicated with t-butyl methyl ether, isolated by filtration and dried. Where necessary, the product was further purified by recrystallisation to yield the 4-anilino-3-nitrobenzoic acid: e.g. 4-(3-bromophenyl amino)-3-nitrobenzoic acid. (In some cases, for example with heteroaromatic anilines, NMN may be omitted from the reaction mixture).

b) To a stirred solution of the 4-anilino-3-nitrobenzoic acid (0.099 mol) in IMS (or ethanol) (300 mL) was added iron dust (33.2 g, 0.594 mol) and glacial acetic acid (300 mL). The resulting mixture was heated at reflux for 3 h, then concentrated to dryness under reduced pressure. Formic acid (300 mL) was added and the reaction mixture was heated at reflux overnight. The reaction mixture was poured onto ice and diluted with water (up to 2000 mL) and stirred for 30 min. The resultant gelatinous mixture was filtered and the residue washed with water. The crude product was suspended in water and basified with 2M. aqueous sodium hydroxide (to pH 10-12) and then MeOH (500 mL) and DMF (100 mL) were added. The suspension was filtered through Celite and decolorising charcoal was added to the solution and the suspension was again filtered through Celite. The filtrate was concentrated in vacuo and the resultant solid residue was suspended in water and acidified with 2M. aqueous hydrochloric acid (to pH 2-3). The mixture was sonicated for 1.5 hours. The resultant precipitate was filtered off, washed with water and dried to give the desired 1-aryl-1H-benzimidazole-5-carboxylic acid: e.g. 1-(3-bromophenyl)-1H-benzimidazole-5-carboxylic acid; $^1$H NMR (DMSO-d6, 400 MHz): δ 12.9 (br. s), 8.74 (s, 1H), 8.33 (d, 1H, J=0.8 Hz), 8.00 (dd, 1H, J=1.6, 1.6 Hz), 7.96 (dd, 1H, J=8.8, 1.6 Hz), 7.78-7.73 (m, 2H), 7.71 (dd, 1H, J=8.4, 8.4Hz) and 7.61 (dd, 1H, J=8.4, 8.4 Hz); MS (ES+): m/z 317.1/319.1 [MH$^+$; Br79/81] at R$_t$ 3.22 min.; m.p. 289-290° C.

Alternatively, a stirred solution of the 4-anilino-3-nitrobenzoic acid (5.5 g, 0.017 mol), triethylamine (16 ml) and 10% Pd on carbon (0.2 g) was warmed to 60° C. before formic acid (10 ml) was added dropwise. The resulting solution was stirred at reflux for 20 hours under nitrogen. The hot mixture was filtered through a pad of Celite, and the cake was washed with hot DMF and EtOH. The filtrate was concentrated under reduced pressure, the residue was triturated with water, isolated by filtration, sonicated with MeCN, washed with t-butyl methyl ether and dried to give the desired 1-aryl-1H-benzimidazole-5-carboxylic acid (in some cases, column chromatographic purification of the desired product was required): e.g. 1-(4-pyrazol-1-yl-phenyl)-1H-benzoimidazole-5-carboxylic acid; $^1$H NMR (DMSO-d6, 400 MHz): δ 12.80 (br. s, 1H), 8.72 (s, 1H), 8.62 (d, J=2.3Hz, 1H), 8.34 (s, 1H), 8.10 (d, J=8.7 Hz, 2H), 7.96 (d, J=8.7 Hz, 1H), 7.84 (d, J=8.7 Hz, 2H), 7.81 (m, 1H), 7.71 (d, J=8.7 Hz, 1H), 6.60 (m, 1H); MS (ES+): m/z 305.2 [MH$^+$] at R$_t$ 2.89 min.; m.p. 278-279 ° C.

c) 1-(Aryl/heteroaryl-phenyl)-1H-benzimidazole-5-carboxylic acids

A 250 mL Schlenk-type flask was charged with the 1-bromophenyl-1H-benzimidazole-5-carboxylic acid (3.0 g, 9.45 mmol), an aryl/heteroaryl boronic acid (1.5 g, 11.71 mmol), Pd(PPh$_3$)$_4$ (0.55 g, 5 mol %) and DMF (90 mL). The mixture was stirred at r.t. for 15 min under nitrogen, before a solution of sodium carbonate (4.8 g) in water (12 mL) was added under nitrogen. The mixture was refluxed for 24 h and filtered while still hot through Celite. After the Celite was washed twice with hot DMF, the combined filtrate was concentrated in vacuo. The resultant residue was dissolved in water and acidified (to pH 4) with 1 M HCl (aq). The resultant precipitate was filtered off, washed with water and dried. This crude product was sonicated with acetonitrile, filtered off, washed with t-butyl methyl ether and dried to give the desired 1-aryl/heteroaryl-phenyl-1H-benzimidazole-5-carboxylic acid: e.g. 1-(3-thiophen-3-yl-phenyl)-1H-benzimidazole-5-carboxylic acid; $^1$H NMR (400 MHz, d6-DMSO): δ 12.84 (br. s, 1H), 8.78 (s, 1H), 8.37 (s, 1H), 8.08 (s, 1H), 8.05 (s, 1H), 7.98 (d, J=9 Hz, 1H), 7.88 (d, J=9 Hz, 1H), 7.78-7.60 (m, 5H); MS (ES+): m/z 321.2 (100%) [MH$^+$] at R$_t$ 3.31 min.; m.p. 274-275° C.

d) 1-(Amin-yl-phenyl)-1H-benzimidazole-5-carboxylic acids a. Thionyl chloride (10 mL, 0.137 mol) was added dropwise to a stirred suspension of the 1-bromophenyl-1H-benzimidazole-5-carboxylic acid (20 g, 0.063 mol) in MeOH (200 mL) at 0-5° C. The reaction was stirred at reflux for 18 h and then concentrated under reduced pressure. The solid residue was triturated with cold water, basified with aqueous ammonium hydroxide solution and extracted with DCM. The extract was washed with water, aqueous brine solution, dried over MgSO$_4$ and concentrated in vacuo to give the corresponding 1-bromophenyl-1H-benzimidazole-5-carboxylic acid methyl ester: e.g. 1-(4-bromophenyl)-1H-benzimidazole carboxylic acid methyl ester.

b. Palladium-Catalysed Amination: A mixture of the 1-bromophenyl-1H-benzimidazole-5-carboxylic acid methyl ester (5.0 g, 0.0151 mol), the amine (2.0 g, 0.0227 mol), Cs$_2$CO$_3$ (8.6 g, 0.0264 mol), Pd$_2$(dba)$_3$ (0.28 g, 0.3 mmol, 2 mol %) and BINAP (0.56 g, 0.91 mmol, 6 mol %) in dioxane (100 mL) was stirred at 90° C. for 64 h. The reaction mixture was poured onto water and extracted several times with EtOAc. The combined extracts were washed with water, aqueous brine solution, dried over MgSO$_4$ and concentrated in vacuo to give the crude 1-(amino-yl-phenyl)-1H-benzimidazole-5-carboxylic acid methyl ester product, which was purified by flash chromatography: e.g. 1-(4-morpholin-4-yl-phenyl)-1H-benzimidazole 5-carboxylic acid methyl ester. (Pd(OAc)$_2$ (2 mol %) and toluene, in place of Pd$_2$(dba)$_3$ and dioxane respectively, may also be employed for this reaction).

c. or Copper-Catalysed Amination: A mixture of the 1-bromophenyl-1H-benzimidazole-5-carboxylic acid methyl ester (3.0 g, 9.0 mmol), the amine (1.63 g, 13.5 mmol), KCO$_3$ (2.49 g, 18.0 mmol), copper (I) iodide (0.171 g, 0.9 mmol) and L-proline (0.21 g, 1.8 mmol) in DMSO (40 mL) was stirred at 90° C. for 63 h. The cooled mixture was partitioned between 5% aqueous ammonium chloride solution and EtOAc. The organic layer was separated, and the aqueous phase back extracted with EtOAc. The combined organic extracts were washed with aqueous brine solution, dried over MgSO$_4$, and concentrated in vacuo to give the crude 1-(amino-yl-phenyl)-1H-benzimidazole-5-carboxylic acid methyl ester product, which was purified by flash chromatography: e.g. 1-[4-(3-Methyl-benzylamino)-phenyl]-1H-benzimidazole-5-carboxylic acid methyl ester.

d. A mixture of the 1-(amin-yl-phenyl)-1H-benzimidazole-5-carboxylic acid methyl ester (3.0 g, 8.9 mmol) and lithium hydroxide (0.64 g, 26.7 mmol) in 2:1 THF/water (30 mL) was stirred at 60° C. for 5 h and was then concentrated under reduced pressure. The residue was diluted with water and acidified with 5% aqueous hydrochloric acid. The resultant solid was filtered off, washed with water and dried to afford the desired 1-(amino-yl-phenyl)-1H-benzimidazole-5-carboxylic acid: e.g. 1-(4-morpholin-4-yl-phenyl)-1H-benzimidazole 5-carboxylic acid; $^1$H NMR (DMSO-d6, 250 MHz): δ 12.85 (br. s, 1H), 8.58 (s, 1H), 8.32 (s, 1H), 7.92 (d, J=8.6 Hz, 1H), 7.60 (d, J=8.5 Hz, 1H), 7.56 (d, J=8.6 Hz, 1H), 7.13 (d, J=8.5 Hz, 1H), 3.74 (t, J=4.6 Hz, 4H), 3.37 (t, J=4.3 Hz, 4H); MS (ES+): m/z 322.2 [MH$^+$] (100%) at $R_t$ 2.86 min.; m.p. 269-270 C. And e.g. 1-[4-(3-methyl-benzylamino)-phenyl]-1H-benzoimidazole-5-carboxylic acid; 1H NMR (DMSO-d6, 400 MHz): δ 12.80 (br. s, 1H), 8.48 (s, 1H), 8.30 (s, 1H), 7.90 (d, J=8.5 Hz, 1H), 7.50 (d, J=8.5 Hz, 2H), 7.31 (d, J=8.7 Hz, 2H), 7.27-7.17 (m, 3H), 7.06 (d, J=6.9 Hz, 1H), 6.76 (d, J=8.7 Hz, 2H), 6.67 (br. t, NH), 4.30 (d, J=4.4 Hz, 2H), 2.30 (s, 3H); MS (ES+): m/z 357.2 [MH$^+$] (100%) at Rt 3.69 min.; m.p. 217-218° C.

e. Alternatively, for the preparation of water soluble acids the following modified work-up was preferred: after removal of organic solvent from the reaction mixture, Amberlyst IR-120 (plus) ion-exchange resin was added in portions to a stirred aqueous solution of the residue until the solution reached pH 6. The mixture was filtered, and the resin was washed with MeOH. The combined filtrates were concentrated to dryness under reduced pressure and residual water was removed by co-distillation with toluene. The crude oily residue was sonicated and then stirred in MeCN overnight to typically give a crystalline material that was filtered off, washed with MeCN and dried in vacuo to furnish the desired 1-(amino-yl-phenyl)-1H-benzimidazole-5-carboxylic acid.

The above describes the various processes to form the building blocks for use in the general procedure to make a combinatorial library of benzimidazoles from the building blocks.

General Procedures for the Preparation of N1-Substituted Benzimidazole-5-Carboxamides A flask containing a mixture of PS-TFP (1.32 mmol/g, 350 mg, 0.462 mmol), the N1-substituted-1H-benzimidazole-5-carboxylic acid (222 mg, 0.693 mmol) and DMAP (33 mg, 0.277 mmol) was charged with DMF (ca. 10 mL) and shaken at r.t. for 10 min. DIC (262 mg, 2.079 mmol) was added and the reaction shaken at r.t. for 3d. The reaction was filtered and the resin washed with DMF (35 mL), THF (15 mL) and DCM (15 mL) before being dried in a vacuum oven overnight.

A portion of the polymer-bound N1-substituted 1H-benzimidazole-5-carboxylic acid (86 mg, 0.075 mmol) was treated with a solution of the amine (300 μL; 0.2 mol/mL; ca. 0.9 eq.) in DMF (1 mL) for 3 d at r.t. The reaction was filtered, the resin washed with DMF (0.9 mL). The filtrate was concentrated in vacuo to yield the desired N1-substituted benzimidazole-5-carboxamide: e.g. N-methyl-1-(3-thien-3-ylphenyl)-1H-benzimidazole-5-carboxamide; $^1$H NMR (500 MHz, d$_6$-DMSO): δ 8.75 (s, 1H), 8.50 (d, 1H), 8.30 (s, 1H), 8.10 (s, 1H), 8.05 (s, 1H), 7.85 (m, 2H), 7.7 (m, 5H), 2.85 (d, 3H); MS (ES+): m/z 334.1 (100%) [MH$^+$]; $R_t$ 3.40 min.

Where cleavage from resin failed to provide the desired amide product in the required >85% purity (as determined by UV detection at 220 nm), the compound was purified by either UV or mass-directed HPLC.

Automated Synthesis Details

The resin (0.075 mmol) was delivered to the required number of wells of a 96-well MTP using either a Titan™ resin dispenser or an Argoscoop™, and DMF (0.7 mL) was added to each well using a liquid handler (e.g. Tecan Genesis™). Next, 300 μL of each amine (from stock solutions of amines at 0.2 mmol/mL) was added to the appropriate wells using a liquid handler (e.g. Tecan Genesis™). The 96-well MTP was heat sealed and shaken at r.t. for 3d. The liquid was then aspirated from the resin using a liquid handler equipped with filter probes (e.g. Zinsser Analytic LISSY™) and the resin was washed with DMF (900 μL). For LCMS analysis, 20 μL of this solution was taken and diluted with MeOH (80 μl). Finally, the bulk of the reaction solutions were dried down using a Genevac™. A portion (15-20%) of the library was analysed by $^1$H NMR, using either a conventional probe (Varian Mercury 400 spectrometer operating at 400 MHz or a Bruker AMX2 500 spectrometer operating at 500 MHz) or a Flowprobe (Flow-injection samples were run on a Bruker BEST system comprising the Bruker AMX2 500 spectrometer, a Gilson 215 autosampler, a heated transfer line and a Bruker 4 mm FI-SEI NMR probe. The BEST system was controlled by XWINNMR software V2.6).

Purification Details

Mass-Directed Purification

The Mass-directed Purification system consisted of a Micromass Platform LC mass spectrometer, a Waters 600 HPLC pump, a Waters Reagent Manager, a Waters 2700 autosampler, a Waters 996 PDA detector, a Waters Fraction Collector II and Waters Xterra Prep MS C18 columns (19×50 mm). Compounds were eluted with variable water/acetonitrile +0.1% formic acid gradients running over a period of 8 min. The flow rate was 20 mL/min. The system was controlled by MassLynx and FractionLynx software V3.5.

UV-directed Purification

UV-directed Purification was carried out on a 4 channel Biotage Parallex Flex system equipped with 4 Waters Xterra Prep MS C18 columns (19×50 mm). Compounds were eluted using a water/acetonitrile+0.1% formic acid gradient with a cycle time of 10 min and a flow rate of 20 mL/min. LW detection was at 220 nm and 254 nm. The system was controlled by Biotage Parallex Flex software V2.9.

Library Monomers

Amines

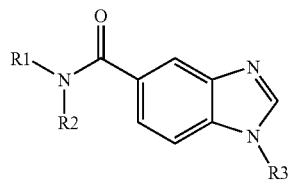

The amines (R1R2NH) used for all subsets of the library were:
1. (aminomethyl)cyclopropane
2. 2-(2-aminoethyl)pyridine
3. 2-(aminomethyl)pyridine
4. 4-(2-aminoethyl)morpholine
5. tetrahydrofurfurylamine
6. veratrylamine
7. 1-(2-aminoethyl)-2-imidazolone
8. 5-amino-2-methoxyphenol
9. 3-aminobenzyl alcohol
10. 4-amino-m-cresol
11. 5-chloro-2-methylbenzylamine 12. 2-(aminomethyl)-5-methylpyrazine
13. 3-(2-aminoethyl)pyridine
14. 4-(trifluoromethyl)piperidine hydrochloride
15. 3-picolylmethylamine
16. 1-(3-aminopropyl)imidazole
17. 1-(3-aminopropyl)-2-pyrrolidinone
18. isopropylamine
19. 2-methylbenzylamine
20. 3-methylbenzylamine
21. 3-fluorobenzylamine
22. 4-fluorobenzylamine
23. N,N-dimethyl-1,3-propanediamine
24. 4-(3-aminopropyl)morpholine
25. DL-1-amino-2-Propanol
26. cyclopropylamine
27. 2-methoxyethylamine
28. histamine
29. piperonylamine
30. 1-phenylpiperazine
31. 4-piperazinoacetophenone
32. 1-(2-pyridyl)piperazine
33. 4-hydroxy-4-phenylpiperidine
34. 4-acetyl-4-phenylpiperidine hydrochloride
35. 1-(3-methoxyphenyl)piperazine
36. 1-(4-methoxyphenyl)piperazine
37. 1-methylpiperazine
38. 1-(2-methoxyphenyl)piperazine
39. 1-(2-hydroxyethyl)piperazine
40. 1-(2,4-dimethoxyphenyl)piperazine
41. 1-piperazinepropanol
42. 1-(2-morpholinoethyl)piperazine
43. 1-(4-hydroxyphenyl)piperazine
44. 1-(2-furoyl)piperazine
45. 1-ethylpiperazine
46. 1-acetylpiperazine
47. 2-piperazin-1-yl-1-pyrrolidin-1-ylethanone
48. N,N-dimethylethylenediamine
49. 4-benzylpiperidine
50. 4-cyano-4-phenylpiperidine hydrochloride
51. 1-(2-dimethylaminoethyl)piperazine
52. 4-benzyl-4-hydroxypiperidine
53. 1-(4-pyridyl)piperazine
54. N-(3-hydroxyphenyl)piperazine
55. N-(2-hydroxyphenyl)piperazine
56. 1-(2-cyanophenyl)piperazine
57. 4-(hydroxymethyl)piperidine
58. 4-hydroxypiperidine
59. 4-piperidinopiperidine
60. 4-(1-pyrollidino)piperidine
61. isonipecotamide
62. piperidine
63. N,N-diethylnipecotamide
64. 3-piperidinemethanol
65. 3-hydroxypiperidine
66. 4-piperazinoindole
67. 1-(2-pyrazinyl)piperazine
68. 4-(aminomethyl)pyridine
69. 4-(trifluoromethoxy)benzylamine
70. 4-methoxybenzylamine
71. 4-chlorobenzylamine
72. 1-(tetrahydro-2-furoyl)piperazine
73. 1-(2-(6-methylpyridyl))piperazine
74. 1-(4-cyanophenyl)piperazine
75. 3-chloro-4-methylbenzylamine
76. pyrrolidine
77. diethylamine
78. 4-piperazinoindole
79. 1,2,3,6-tetrahydropyridine
80. 2-(2-methylaminoethyl)pyridine
81. 1-methyl-4-(methylamino)piperidine
82. 1-(2-Pyrrolidinylmethyl)pyrrolidine
83. N,N,N'-trimethylethylenediamine
84. 2,6-dimethylmorpholine
85. 8-aza-1,4-dioxaspiro[4.5]decane(4-piperidone ethylene ketal)
86. N-(4-aminophenyl)-N-methylacetamide
87. 2-(4-aminophenyl)ethanol
88. 3-fluoro-P-anisidine
89. p-toluidine
90. 3,4-ethylenedioxyaniline
91. 1-acetyl-6-aminoindoline
92. 4-fluoroaniline
93. 3-fluoro-4-methylaniline
94. p-anisidine
95. 3-chloro-4-fluoroaniline
96. m-anisidine
97. 3,4-difluoroaniline
98. 3-methoxybenzylamine
99. 4-methylbenzylamine
100. 3-chloro-4-methylaniline
101. 3-(trifluoromethyl)benzylamine
102. 2-chlorobenzylamine
103. 3,5-dimethoxybenzylamine
104. 2-fluorobenzylamine
105. 3-(trifluoromethoxy)benzylamine
106. 4-aminoacetanilide
107. 3-amino-o-cresol
108. N1-(4-amino-2-methylphenyl)acetamide
109. 1-(2-piperidinoethyl)piperazine
110. 1-morpholin-4-yl-2-piperazin-1-yl-ethanone
111. 1-(4-pyridylmethyl)piperazine
112. N,N-dimethyl-2-piperazin-1-yl-acetamide
113. 1-(3-dimethylaminopropyl)piperazine
114. 1-(3-morpholinopropyl)piperazine
115. 1-(3-pyrrolidinopropyl)piperazine
116. 1-(2-ethoxyethyl)piperazine
117. 1-pyridin-2-ylmethylpiperazine
118. (4-fluorophenyl)piperazin-1-ylmethanone
119. (3-fluorophenyl)piperazin-1-ylmethanone
120. 2-aminobenzyl alcohol
121. 4-aminotetrahydropyran
122. ethylamine
123. methylamine
124. benzylamine
125. cyclohexanemethylamine
126. 3-(aminomethyl)pyridine
127. butylamine
128. 2-piperidineethanol
129. morpholine
130. 1-(3-methoxyphenyl)piperazine
131. n-methylcyclohexylamine
132. 2,4-dimethoxyaniline Library Subset A: Simple functionalised Phenyls at R3 Benzimidazole-5Carboxylic Acid Building Blocks

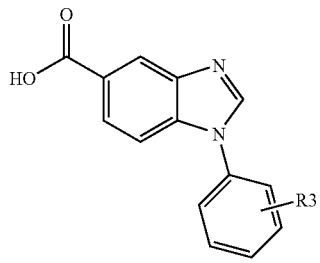

Anilines (R3NH$_2$) used to install R3:

A. Aniline
B. 3-Bromoaniline
C. 4-Bromoaniline
D. 3'-Aminoacetophenone
E. 3'-Aminoacetanilide
F. 4'-Aminoacetanilide
G. Methyl 3-aminobenzoate
H. Methyl 4-aminobenzoate

TABLE 1

Tabulated in Table 1 below is a combinatorial library—Subset A, formed by the process of the present invention. The data is presented in a format [M + H]$^+$ (R$_t$).

Subset A

| R1R2NH Amine | Benzimidazole Carboxylic acid Building Block derived from anilines A-F | | | | | |
|---|---|---|---|---|---|---|
| | A | B | C | D | E | F |
| 1 | 292.5 (3.05) | 370.0/372.0 (3.55) | 370.0/372.0 (3.55) | 334.3 (2.55) | 349.3 (2.85) | 349.2 (2.85) |
| 2 | 343.3 (2.45) | N/A | N/A | 385.3 (2.45) | 400.4 (2.40) | N/A |
| 3 | 329.3 (2.55) | 407.0/409.0 (2.95) | 407.1/409.1 (2.85) | 371.3 (2.40) | 386.3 (2.40) | N/A |
| 4 | 351.3 (2.50) | N/A | 429.1/431.1 (2.85) | 393.3 (2.40) | 408.4 (2.45) | N/A |
| 5 | 322.3 (2.95) | N/A | 400.0/402.0 (3.45) | 364.3 (2.55) | 379.3 (2.20) | 379.2 (2.80) |
| 6 | 388.3 (3.20) | N/A | 466.0/468.1 (3.55) | 430.4 (3.20) | 445.3 (2.95) | 445.2 (3.05) |
| 7 | N/A | 428.1/430.1 (3.10) | N/A | 392.3 (2.70) | 407.4 (2.60) | N/A |
| 8 | 360.3 (3.05) | 438.0/440.0 (3.45) | 438.1/440.1 (3.45) | 402.3 (2.20) | 417.3 (2.85) | 417.2 (2.85) |
| 9 | 344.3 (3.15) | 422.0/424.0 (3.55) | 422.1/424.1 (3.55) | 386.3 (2.85) | 401.3 (3.05) | 401.2 (2.95) |
| 10 | 344.3 (3.00) | 422.0/424.0 (3.40) | 422.0/424.0 (3.45) | 386.3 (2.65) | 401.3 (2.80) | 401.2 (2.80) |
| 11 | N/A | N/A | N/A | 418.3/420.3 (3.60) | 433.3/435.4 (3.40) | 433.2/435.2 (3.45) |
| 12 | 344.3 (3.05) | N/A | N/A | N/A | 401.3 (2.80) | 401.2 (2.70) |
| 13 | N/A | 421.1/423.1 (2.70) | 421.1/423.1 (2.75) | N/A | 400.3 (2.35) | N/A |
| 14 | 374.3 (3.60) | 452.0/454.1 (3.85) | 452.0/454.1 (3.85) | 416.3 (3.55) | 431.3 (3.35) | 431.1 (3.30) |
| 15 | 343.3 (2.45) | 421.0/423.0 (2.85) | 421.1/423.1 (3.10) | 385.3 (2.30) | 400.3 (2.35) | 400.2 (2.55) |
| 16 | 346.3 (2.45) | 424.1/426.1 (2.80) | 424.1/426.1 (2.70) | 388.3 (2.40) | 403.4 (2.35) | N/A |
| 17 | 363.3 (2.80) | N/A | N/A | 405.4 (2.60) | 420.4 (2.65) | 420.2 (2.70) |
| 18 | 280.2 (3.10) | N/A | 358.0/360.0 (3.50) | 322.3 (2.90) | 337.3 (2.95) | 337.2 (2.90) |
| 19 | 342.3 (3.50) | 420.1/422.1 (3.95) | 420.0/422.1 (3.80) | 384.3 (3.40) | 399.3 (3.20) | N/A |
| 20 | 342.3 (3.45) | N/A | N/A | 384.3 (3.40) | 399.4 (3.20) | N/A |
| 21 | 346.3 (3.30) | 424.0/426.0 (3.75) | 424.0/426.0 (3.75) | 388.3 (3.25) | 403.3 (3.20) | N/A |
| 22 | 346.3 (3.50) | 424.0/426.0 (3.70) | 424.0/426.0 (3.70) | 388.3 (3.55) | 403.4 (3.20) | 403.1 (3.15) |
| 23 | 323.3 (2.40) | N/A | N/A | 365.3 (2.40) | 380.4 (2.40) | N/A |
| 24 | 365.3 (2.35) | N/A | N/A | 407.4 (2.35) | 422.4 (2.30) | N/A |
| 25 | 296.2 (2.75) | 374.0/376.0 (3.25) | 374.1/376.1 (3.15) | 338.3 (2.75) | 353.3 (2.70) | N/A |
| 26 | 278.2 (2.80) | N/A | 356.0/358.0 (3.35) | 320.3 (2.80) | 335.3 (2.65) | 335.2 (2.70) |
| 27 | 296.2 (2.95) | N/A | N/A | 338.3 (2.70) | 353.3 (2.65) | N/A |
| 28 | N/A | N/A | N/A | 374.3 (2.35) | 389.3 (2.25) | N/A |
| 29 | 372.3 (3.30) | 450.1/452.1 (3.70) | 450.1/452.1 (3.85) | 414.3 (3.30) | 429.3 (3.05) | 429.2 (3.25) |
| 30 | 383.3 (3.60) | 461.1/463.1 (4.00) | N/A | 425.4 (3.55) | 440.4 (3.35) | 440.2 (3.25) |
| 31 | 425.3 (3.30) | 503.1/505.1 (3.70) | 503.1/505.1 (3.60) | 467.4 (3.20) | 482.4 (3.10) | 482.2 (3.10) |
| 32 | 384.3 (2.65) | N/A | 462.1/464.1 (2.75) | 426.4 (2.60) | 441.4 (2.40) | 441.2 (2.40) |
| 33 | 398.3 (3.15) | 476.1/478.1 (3.55) | 476.1/478.1 (3.50) | 440.4 (3.10) | 455.4 (2.95) | N/A |
| 34 | 424.3 (3.70) | 502.1/504.1 (4.05) | 502.1/504.1 (3.95) | 466.4 (3.60) | 481.4 (3.45) | 481.2 (3.40) |
| 35 | 413.3 (3.40) | 491.1/493.1 (3.90) | 491.1/493.1 (4.00) | 455.4 (3.35) | N/A | 470.2 (3.40) |
| 36 | 413.4 (3.25) | N/A | 491.2/493.1 (3.55) | 455.4 (3.20) | N/A | 470.3 (3.00) |
| 37 | 321.3 (2.35) | 399.1/401.1 (2.75) | 399.1/401.1 (2.70) | 363.3 (2.35) | 378.4 (2.40) | 378.2 (2.30) |
| 38 | 413.3 (3.30) | N/A | 491.1/493.1 (3.75) | 455.4 (3.25) | 470.4 (3.10) | 470.2 (3.15) |
| 39 | 351.3 (2.25) | 429.1/431.1 (2.55) | 429.0/431.0 (2.55) | 393.3 (2.25) | 408.3 (2.15) | 408.2 (2.15) |
| 40 | N/A | N/A | N/A | 485.4 (3.10) | 500.5 (2.90) | N/A |
| 41 | 365.3 (2.20) | 443.1/445.1 (2.60) | 443.0/445.0 (2.55) | 407.4 (2.20) | 422.3 (2.15) | 422.3 (2.20) |
| 42 | 420.4 (2.40) | 498.2/500.2 (2.80) | 498.2/500.2 (2.80) | 462.4 (2.50) | 477.5 (2.35) | 477.3 (2.40) |
| 43 | 399.3 (2.80) | 477.1/479.1 (3.35) | 477.1/479.1 (3.25) | 441.4 (2.70) | 456.4 (2.60) | 456.2 (2.70) |
| 44 | 401.3 (2.95) | 479.1/481.1 (3.30) | 479.1/481.1 (3.30) | 443.3 (2.90) | 458.4 (2.80) | 458.2 (2.75) |
| 45 | 335.3 (2.25) | 413.1/415.1 (2.65) | 413.1/415.1 (2.60) | 377.3 (2.30) | 392.3 (2.20) | 392.3 (2.20) |
| 46 | 349.3 (2.80) | 427.1/429.1 (3.25) | 427.1/429.1 (3.25) | 391.3 (2.85) | 406.4 (2.70) | N/A |
| 47 | 418.4 (2.50) | 496.2/498.2 (2.75) | 496.2/498.2 (2.70) | 460.4 (2.55) | 475.4 (2.40) | N/A |
| 48 | 309.3 (2.30) | N/A | N/A | 351.3 (2.30) | 366.3 (2.25) | N/A |
| 49 | N/A | N/A | N/A | 438.4 (3.65) | 453.4 (3.45) | N/A |
| 50 | 407.3 (3.50) | 485.1/487.1 (3.80) | N/A | 449.3 (3.50) | 464.4 (3.35) | 464.2 (3.25) |

TABLE 1-continued

Tabulated in Table 1 below is a combinatorial library—Subset A, formed by the process of the present invention. The data is presented in a format [M + H]⁺ (R$_t$).

Subset A

| R1R2NH Amine | Benzimidazole Carboxylic acid Building Block derived from anilines A-F | | | | | |
|---|---|---|---|---|---|---|
| | A | B | C | D | E | F |
| 51 | 378.4 (2.25) | 456.2/458.2 (2.75) | 456.2/458.2 (2.75) | 420.4 (2.45) | 435.4 (2.35) | 435.3 (2.35) |
| 52 | N/A | N/A | N/A | 454.4 (3.20) | 469.4 (3.05) | N/A |
| 53 | N/A | 462.1/464.1 (2.75) | 462.1/464.1 (2.70) | 426.4 (2.50) | 441.4 (2.40) | N/A |
| 54 | 399.3 (2.70) | 477.1/479.1 (3.40) | 477.1/479.1 (3.40) | 441.4 (3.05) | 456.4 (2.85) | 456.2 (2.90) |
| 55 | 399.3 (2.90) | N/A | 477.1/479.1 (3.65) | 441.4 (3.25) | 456.4 (3.10) | 456.2 (3.05) |
| 56 | 408.3 (3.00) | 486.1/488.1 (4.00) | 486.1/488.1 (3.85) | 450.4 (3.35) | 465.4 (3.25) | 465.2 (3.30) |
| 57 | 336.3 (2.75) | N/A | N/A | 378.3 (2.65) | 393.4 (2.60) | N/A |
| 58 | 322.3 (2.60) | N/A | N/A | 364.3 (2.60) | 379.3 (2.45) | N/A |
| 59 | 389.4 (2.45) | N/A | N/A | 431.4 (2.60) | N/A | N/A |
| 60 | 375.4 (2.40) | 453.1/455.1 (2.75) | 453.1/455.1 (2.70) | 417.4 (2.35) | 432.4 (2.35) | 432.2 (2.30) |
| 61 | 349.3 (2.60) | 427.1/429.1 (2.95) | 427.1/429.1 (3.00) | 391.3 (2.75) | 406.4 (2.60) | N/A |
| 62 | 306.3 (3.10) | 384.0/386.0 (3.50) | 384.0/386.0 (3.55) | 348.3 (3.05) | 363.3 (2.80) | 363.1 (2.90) |
| 63 | 405.4 (3.25) | 483.1/485.1 (3.60) | 483.1/485.1 (3.65) | 447.4 (3.20) | 462.4 (2.95) | 462.2 (3.05) |
| 64 | 336.3 (2.75) | N/A | N/A | 378.3 (2.70) | 393.3 (2.60) | N/A |
| 65 | 322.3 (2.85) | N/A | 400.1/402.1 (3.05) | 364.3 (2.65) | 379.3 (2.60) | N/A |
| 66 | 422.4 (3.25) | 500.1/502.1 (3.60) | 500.1/502.1 (3.60) | 464.4 (3.20) | 479.4 (3.00) | N/A |
| 67 | 385.3 (3.15) | N/A | 463.1/465.1 (3.55) | 427.4 (3.10) | 442.4 (3.00) | 442.2 (2.95) |
| 68 | 329.3 (2.60) | 407.1/409.1 (2.75) | 407.1/409.1 (2.75) | 371.3 (2.40) | 386.3 (2.35) | 386.2 (2.35) |
| 69 | 412.3 (3.90) | 490.0/492.0 (4.00) | 490.0/492.0 (4.00) | 454.3 (3.75) | 469.3 (3.65) | 469.1 (3.15) |
| 70 | 358.3 (2.80) | 436.1/438.1 (3.65) | 436.1/438.1 (3.65) | 400.3 (3.20) | 415.3 (3.05) | 415.2 (3.10) |
| 71 | 362.2/364.3 (3.60) | 440.0/442.0 (4.00) | 440.0/442.0 (3.85) | 404.3/406.3 (3.70) | 419.3/421.3 (3.30) | 419.1/421.2 (3.15) |
| 72 | 405.3 (2.80) | 483.1/485.1 (3.35) | 483.1/485.1 (3.20) | 447.4 (2.70) | 462.4 (2.60) | N/A |
| 73 | 398.4 (2.60) | 476.1/478.1 (2.80) | 476.1/478.1 (2.80) | 440.4 (2.50) | 455.4 (2.50) | 455.3 (2.45) |
| 74 | 408.3 (3.45) | 486.1/488.1 (3.70) | 486.1/488.1 (3.70) | 450.4 (3.30) | N/A | 465.2 (3.15) |
| 75 | 376.3/378.3 (3.65) | 454.1/456.0 (4.00) | 454.0/456.0 (3.95) | 418.3/420.3 (3.65) | 433.3/435.4 (3.40) | N/A |
| 76 | 292.3 (3.10) | N/A | N/A | N/A | 349.3 (2.90) | N/A |
| 77 | 294.3 (3.00) | 372.0/374.0 (3.50) | 372.0/374.0 (3.45) | 336.3 (2.95) | 351.3 (2.80) | 351.1 (2.75) |
| 78 | 422.4 (4.30) | 500.1/502.1 (3.60) | 500.1/502.1 (3.60) | 464.4 (3.40) | 479.4 (3.10) | 479.2 (3.05) |
| 79 | 304.3 (3.05) | 382.0/384.1 (3.50) | 382.1/384.1 (3.40) | 346.3 (3.10) | 361.3 (2.90) | 361.2 (2.85) |
| 80 | 357.3 (2.40) | 435.1/437.1 (2.75) | 435.1/437.1 (2.75) | 399.3 (2.35) | 414.4 (2.35) | 414.2 (2.35) |
| 81 | 349.3 (2.40) | 427.1/429.1 (2.80) | 427.1/429.1 (2.75) | 391.4 (2.40) | 406.4 (2.35) | 406.3 (2.35) |
| 82 | 375.4 (2.40) | 453.1/455.1 (2.80) | 453.1/455.1 (2.90) | 417.4 (2.35) | 432.4 (2.40) | 432.2 (2.45) |
| 83 | 323.3 (2.50) | 401.1/403.1 (2.60) | 401.1/403.1 (2.65) | 365.3 (2.40) | 380.4 (2.30) | N/A |
| 84 | 336.3 (2.95) | 414.1/416.1 (3.40) | 414.1/416.1 (3.40) | 378.3 (2.55) | 393.3 (2.75) | N/A |
| 85 | 364.3 (3.10) | N/A | 442.1/444.1 (3.55) | 406.3 (2.70) | 421.3 (2.95) | N/A |
| 86 | N/A | N/A | 463.1/465.1 (3.60) | N/A | N/A | 442.2 (3.00) |
| 87 | N/A | 436.1/438.1 (3.40) | 436.1/438.1 (3.45) | 400.3 (3.05) | N/A | 415.2 (2.85) |
| 88 | 362.3 (3.65) | 440.1/442.1 (3.90) | 440.1/442.1 (3.95) | 404.3 (3.50) | 419.3 (3.40) | 419.2 (3.10) |
| 89 | 328.3 (3.55) | 406.1/408.1 (3.85) | 406.1/408.1 (3.90) | 370.3 (3.50) | 385.3 (3.25) | 385.2 (3.30) |
| 90 | 372.3 (3.50) | 450.1/452.1 (3.90) | 450.1/452.1 (3.75) | 414.3 (3.55) | 429.4 (3.25) | 429.2 (3.25) |
| 91 | 397.3 (3.20) | 475.1/477.1 (3.60) | 475.1/477.1 (3.55) | 439.4 (3.25) | 454.4 (3.05) | 454.2 (3.00) |
| 92 | 332.3 (3.50) | 410.1/412.1 (3.80) | 410.0/412.0 (3.80) | 374.3 (3.45) | 389.3 (3.25) | 389.1 (3.15) |
| 93 | N/A | 424.1/426.1 (4.05) | 424.1/426.1 (4.15) | 388.3 (3.85) | 403.4 (3.45) | N/A |
| 94 | 344.3 (3.35) | N/A | N/A | 386.3 (3.30) | 401.3 (3.10) | N/A |
| 95 | 366.3/368.3 (3.75) | N/A | N/A | N/A | 423.3/425.3 (3.50) | N/A |
| 96 | 344.3 (3.65) | N/A | N/A | N/A | 401.3 (3.40) | N/A |
| 97 | N/A | N/A | 428.0/430.0 (3.95) | N/A | N/A | N/A |
| 98 | 358.3 (3.35) | 436.1/438.1 (3.85) | 436.1/438.1 (3.75) | 400.3 (3.30) | 415.3 (3.05) | N/A |
| 99 | 342.3 (3.70) | 420.1/422.1 (3.85) | 420.0/422.1 (3.75) | 384.3 (3.50) | 399.3 (3.40) | 399.2 (3.20) |
| 100 | 362.3/364.3 (3.85) | N/A | 440.0/442.0 (4.30) | 404.3/406.3 (3.50) | 419.3/421.3 (3.55) | N/A |
| 101 | N/A | 474.0/476.0 (3.90) | 474.0/476.0 (3.95) | N/A | N/A | 453.1 (3.40) |
| 102 | 362.2/364.2 (3.50) | 440.0/442.0 (4.00) | 440.0/442.0 (3.90) | 404.3/406.3 (3.45) | 419.3/421.3 (3.25) | 419.1/421.2 (3.25) |
| 103 | 388.3 (3.55) | N/A | N/A | N/A | 445.3 (3.35) | 445.2 (3.10) |
| 104 | N/A | N/A | N/A | 388.3 (3.30) | 403.3 (3.10) | 403.2 (3.25) |
| 105 | N/A | N/A | N/A | 454.4 (3.80) | 469.4 (3.45) | 469.1 (3.50) |
| 106 | 371.3 (2.95) | 449.1/451.1 (3.35) | 449.1/451.1 (3.35) | 413.3 (3.00) | 428.4 (2.70) | 428.2 (2.80) |
| 107 | N/A | N/A | 422.1/424.1 (3.55) | N/A | N/A | 401.2 (2.95) |
| 108 | 385.3 (3.00) | 463.1/465.1 (3.35) | 463.1/465.1 (3.35) | 427.3 (2.95) | 442.4 (2.70) | 442.2 (2.85) |
| 109 | 418.4 (2.30) | 496.2/498.2 (2.70) | N/A | 460.5 (2.30) | 475.5 (2.25) | N/A |
| 110 | 434.4 (2.35) | N/A | N/A | N/A | N/A | N/A |
| 111 | 398.4 (2.50) | N/A | N/A | N/A | 455.4 (2.50) | N/A |
| 112 | 392.4 (2.20) | 470.1/472.1 (2.65) | 470.1/472.1 (2.60) | 434.4 (2.40) | 449.4 (2.20) | N/A |
| 113 | 392.4 (2.10) | 470.1/472.1 (2.30) | 470.1/472.1 (2.40) | 434.4 (1.95) | 449.4 (2.00) | 449.3 (2.05) |
| 114 | 434.4 (2.25) | 512.2/514.2 (2.50) | 512.2/514.2 (2.50) | 476.5 (2.15) | 491.4 (2.15) | 491.3 (2.20) |
| 115 | 418.4 (2.05) | N/A | N/A | N/A | N/A | 475.3 (2.05) |
| 116 | 379.4 (2.50) | 457.1/459.1 (2.85) | 457.1/459.1 (2.85) | 421.4 (2.50) | 436.4 (2.45) | 436.2 (2.45) |

TABLE 1-continued

Tabulated in Table 1 below is a combinatorial library—Subset A, formed by the process of the present invention. The data is presented in a format [M + H]$^+$ (R$_t$).

Subset A

| R1R2NH | Benzimidazole Carboxylic acid Building Block derived from anilines A-F | | | | | |
|---|---|---|---|---|---|---|
| Amine | A | B | C | D | E | F |
| 117 | 398.4 (2.40) | N/A | N/A | 440.4 (2.35) | N/A | N/A |
| 118 | 429.3 (3.15) | 507.1/509.1 (3.45) | 507.1/509.1 (3.50) | 471.4 (2.65) | 486.4 (2.90) | 486.2 (2.95) |
| 119 | 429.3 (3.30) | 507.1/509.1 (3.15) | 507.1/509.1 (3.65) | 471.4 (3.15) | 486.4 (3.15) | 486.2 (3.10) |
| 120 | N/A | N/A | 422.1/424.1 (3.60) | 386.3 (3.05) | N/A | 401.2 (3.00) |
| 124 | 328.2 (3.30) | 406.2/408.2 (3.60) | 406.2/408.2 (3.55) | 370.3 (3.25) | 385.2 (3.00) | N/A |
| 125 | N/A | 412.3/414.3 (3.90) | 412.3/414.3 (3.90) | 376.3 (3.55) | 391.3 (3.30) | N/A |
| 126 | 329.3 (2.30) | 407.4/409.4 (2.70) | 407.2/409.2 (2.65) | 371.2 (2.50) | 386.3 (2.30) | N/A |
| 127 | 294.2 (3.35) | 372.2/374.2 (3.70) | 372.2/374.2 (3.70) | 336.3 (3.35) | 351.3 (3.10) | N/A |
| 128 | 350.3 (2.85) | 428.3/430.3 (3.20) | 428.3/430.3 (3.20) | 392.3 (2.90) | 407.4 (2.70) | N/A |
| 129 | 308.2 (2.70) | 386.2/388.2 (3.10) | 386.2/388.2 (3.10) | 350.3 (2.75) | 365.3 (2.55) | N/A |
| 130 | 413.4 (3.30) | 491.3/493.3 (3.65) | 491.3/493.3 (3.65) | 455.4 (3.35) | 470.3 (3.15) | N/A |
| 131 | 334.2 (3.60) | 412.3/414.3 (3.90) | 412.3/414.2 (3.95) | 376.3 (3.55) | 391.3 (3.30) | N/A |
| 132 | 374.3 (3.35) | 452.3/454.3 (3.65) | N/A | 416.3 (3.30) | 431.3 (3.10) | N/A |
| Total | 111 | 84 | 96 | 116 | 116 | 73 |

Total = # of compounds prepared from each benzimidazole-5-carboxylic acid building block Library Subset B: Biaryls from Commercially Available Anilines Benzimidazole-5-Carboxylic Acid Building Blocks

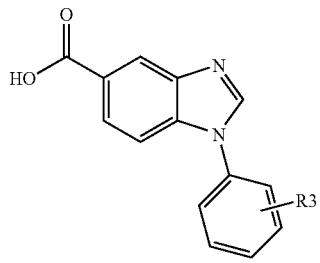

Anilines (R3NH$_2$) used to install R3:
I. 5-(3-Aminophenyl)tetrazole
J. 3-(1H-Pyrrol-1-yl)aniline
K. 4-(1H-Pyrazol-1-yl)aniline
L. 4-(1,2,3-Thiadiazol-4-yl)aniline

TABLE 2

Tabulated in Table 2 below is a combinatorial library—Subset B, formed by the process of the present invention. The data is presented in a format [M + H]$^+$ (R$_t$).

Subset B

| R1R2NH | Benzimidazole Carboxylic acid Building Block derived from anilines I-L | | | |
|---|---|---|---|---|
| Amine | I | J | K | L |
| 1 | 360.3 (2.90) | N/A | 358.3 (3.20) | N/A |
| 2 | 411.3 (2.40) | 408.4 (2.80) | 409.4 (2.60) | N/A |
| 3 | 397.3 (2.60) | N/A | 395.3 (2.60) | N/A |
| 4 | 419.4 (2.35) | 416.4 (2.85) | 417.4 (2.65) | N/A |
| 5 | 390.4 (2.75) | 387.3 (3.30) | 388.3 (3.05) | N/A |
| 6 | 456.4 (3.05) | 453.4 (3.60) | 454.4 (3.25) | N/A |
| 7 | 418.4 (2.60) | 415.4 (3.10) | 416.3 (2.80) | N/A |
| 8 | 428.3 (2.90) | 425.3 (3.45) | 426.3 (3.15) | N/A |
| 9 | 412.3 (3.05) | 409.3 (3.60) | 410.3 (3.30) | N/A |
| 10 | N/A | 409.3 (3.45) | 410.3 (3.10) | N/A |
| 11 | 444.4/446.4 (3.40) | 441.4/443.4 (3.95) | 442.4/444.4 (3.70) | N/A |

TABLE 2-continued

Tabulated in Table 2 below is a combinatorial library—Subset B, formed by the process of the present invention. The data is presented in a format [M + H]$^+$ (R$_t$).

Subset B

| R1R2NH | Benzimidazole Carboxylic acid Building Block derived from anilines I-L | | | |
|---|---|---|---|---|
| Amine | I | J | K | L |
| 12 | 412.3 (2.75) | 409.3 (3.35) | 410.3 (3.05) | N/A |
| 13 | 411.3 (2.35) | 408.4 (2.70) | 409.3 (2.60) | N/A |
| 14 | 442.3 (3.35) | N/A | 440.3 (3.70) | N/A |
| 15 | N/A | N/A | 409.3 (2.60) | N/A |
| 16 | 414.4 (2.60) | 411.4 (2.80) | 412.3 (2.60) | N/A |
| 17 | 431.4 (2.75) | 428.4 (3.20) | 429.4 (2.95) | N/A |
| 18 | N/A | 345.3 (3.60) | 346.3 (3.25) | N/A |
| 19 | 410.4 (3.25) | 407.4 (3.85) | 408.3 (3.50) | N/A |
| 20 | N/A | 407.4 (3.75) | 408.3 (3.55) | N/A |
| 21 | 414.3 (3.20) | 411.3 (3.75) | 412.3 (3.45) | N/A |
| 22 | 414.4 (3.35) | 411.3 (3.95) | 412.3 (3.50) | N/A |
| 23 | 391.4 (2.35) | 388.4 (2.80) | 389.4 (2.60) | N/A |
| 24 | 433.4 (2.40) | 430.4 (2.75) | 431.4 (2.50) | N/A |
| 25 | N/A | 361.3 (3.30) | 362.3 (2.95) | N/A |
| 26 | 346.3 (2.65) | 343.3 (3.35) | 344.3 (3.00) | N/A |
| 27 | 364.3 (2.75) | 361.3 (3.25) | 362.3 (2.95) | N/A |
| 28 | N/A | 397.3 (2.65) | 398.3 (2.45) | N/A |
| 29 | 440.4 (3.15) | 437.4 (3.65) | 438.4 (3.35) | N/A |
| 30 | N/A | 448.4 (4.00) | 449.4 (3.70) | N/A |
| 31 | 493.4 (3.15) | 490.4 (3.70) | 491.4 (3.40) | N/A |
| 32 | 452.4 (2.55) | 449.4 (2.95) | 450.4 (2.65) | N/A |
| 33 | 466.4 (3.00) | 463.4 (3.50) | 464.4 (3.25) | N/A |
| 34 | N/A | 489.4 (4.05) | 490.4 (3.70) | N/A |
| 35 | 481.4 (3.20) | N/A | 479.4 (3.50) | N/A |
| 36 | N/A | 478.4 (3.65) | 479.4 (3.35) | N/A |
| 37 | 389.4 (2.35) | 386.4 (2.75) | 387.3 (2.50) | N/A |
| 38 | 481.4 (3.25) | 478.4 (3.75) | 479.4 (3.40) | N/A |
| 39 | 419.3 (2.20) | 416.4 (2.75) | 417.4 (2.45) | N/A |
| 40 | N/A | 508.5 (3.55) | N/A | N/A |
| 41 | 433.4 (2.25) | 430.4 (2.65) | 431.4 (2.30) | N/A |
| 42 | 488.5 (2.30) | 485.5 (2.60) | 486.5 (2.60) | N/A |
| 43 | 467.4 (2.65) | 464.4 (3.20) | 465.4 (2.90) | N/A |
| 44 | 469.4 (2.85) | 466.4 (3.40) | 467.4 (3.10) | N/A |
| 45 | 403.4 (2.25) | 400.4 (2.60) | 401.4 (2.40) | N/A |
| 46 | 417.4 (2.75) | 414.4 (3.30) | 415.3 (3.00) | N/A |
| 47 | 486.4 (2.45) | 483.4 (2.90) | 484.4 (2.65) | N/A |
| 48 | 377.7 (2.30) | 374.3 (2.70) | 375.3 (2.45) | 393.2 (2.75) |
| 49 | N/A | 461.4 (4.05) | N/A | N/A |

TABLE 2-continued

Tabulated in Table 2 below is a combinatorial library—Subset B, formed by the process of the present invention. The data is presented in a format [M + H]$^+$ (R$_t$).
Subset B

| R1R2NH | Benzimidazole Carboxylic acid Building Block derived from anilines I-L | | | |
|---|---|---|---|---|
| Amine | I | J | K | L |
| 50 | 475.4 (3.35) | N/A | 473.4 (3.60) | N/A |
| 51 | N/A | 443.4 (2.80) | 444.4 (2.50) | N/A |
| 52 | 480.4 (3.10) | 477.4 (3.65) | 478.4 (3.35) | N/A |
| 53 | 452.4 (2.45) | 449.4 (2.85) | 450.4 (2.60) | N/A |
| 54 | 467.4 (2.90) | 464.4 (3.50) | 465.4 (3.15) | N/A |
| 55 | 467.4 (3.10) | N/A | 465.4 (3.45) | N/A |
| 56 | N/A | N/A | 474.4 (3.50) | N/A |
| 57 | 404.4 (2.65) | 401.4 (3.20) | 402.3 (2.85) | N/A |
| 58 | N/A | 387.4 (3.05) | 388.3 (2.75) | N/A |
| 59 | N/A | 454.4 (2.90) | 455.4 (2.70) | N/A |
| 60 | 443.4 (2.35) | 440.4 (2.70) | 441.4 (2.50) | N/A |
| 61 | 417.4 (2.55) | 414.3 (3.05) | 415.3 (2.75) | N/A |
| 62 | 374.3 (2.95) | 371.3 (3.55) | 372.3 (3.15) | N/A |
| 63 | 473.4 (3.10) | 470.4 (3.65) | 471.4 (3.30) | N/A |
| 64 | 404.4 (2.65) | 401.3 (3.25) | 402.3 (2.85) | N/A |
| 65 | 390.3 (2.60) | 387.3 (3.15) | 388.3 (3.00) | N/A |
| 66 | 490.4 (3.05) | N/A | 488.4 (3.30) | N/A |
| 67 | 453.4 (3.00) | 450.4 (3.60) | 451.4 (3.25) | N/A |
| 68 | 397.3 (2.45) | 394.3 (2.85) | 395.3 (2.55) | N/A |
| 69 | 480.4 (3.55) | 477.4 (4.05) | 478.3 (3.95) | N/A |
| 70 | 426.4 (3.10) | 423.3 (3.65) | 424.3 (3.05) | N/A |
| 71 | 430.3/ 432.3 (3.55) | 427.4/ 429.4 (4.05) | N/A | N/A |
| 72 | 473.4 (2.65) | 470.4 (3.20) | 471.4 (2.80) | N/A |
| 73 | 466.4 (2.50) | 463.4 (2.95) | 464.4 (2.70) | N/A |
| 74 | 476.4 (3.20) | N/A | 474.4 (3.40) | N/A |
| 75 | 444.4/ 446.4 (3.15) | N/A | 442.4/ 444.4 (3.25) | N/A |
| 76 | 360.3 (2.95) | 357.3 (3.60) | 358.3 (3.15) | N/A |
| 77 | 362.3 (2.90) | 359.3 (3.20) | 360.3 (3.10) | N/A |
| 78 | 490.4 (3.10) | 487.4 (3.45) | 488.3 (3.25) | N/A |
| 79 | 372.3 (2.90) | 369.3 (3.55) | 370.3 (3.25) | N/A |
| 80 | N/A | 422.4 (2.85) | 423.4 (2.55) | N/A |
| 81 | 417.4 (2.40) | 414.4 (2.60) | 415.4 (2.55) | N/A |
| 82 | 443.4 (2.45) | 440.4 (2.85) | 441.4 (2.55) | N/A |
| 83 | 391.4 (2.30) | 388.4 (2.80) | N/A | N/A |
| 84 | 404.4 (2.80) | 401.3 (3.45) | 402.3 (3.10) | N/A |
| 85 | 432.4 (3.00) | 429.3 (3.60) | 430.3 (3.20) | N/A |
| 87 | 426.3 (2.90) | 423.3 (3.50) | N/A | N/A |
| 88 | 430.4 (3.10) | 427.4 (3.90) | 428.4 (3.75) | N/A |
| 89 | 396.4 (3.10) | 393.4 (3.90) | 394.4 (3.60) | N/A |
| 90 | N/A | 437.4 (3.90) | 438.4 (3.50) | N/A |
| 92 | 400.3 (2.95) | N/A | 398.3 (3.55) | N/A |
| 93 | N/A | N/A | 412.4 (3.80) | N/A |
| 94 | N/A | 409.3 (3.70) | 410.3 (3.45) | N/A |
| 95 | N/A | 431.3/ 433.3 (4.05) | N/A | N/A |
| 96 | 412.4 (3.30) | 409.4 (3.85) | 410.4 (3.70) | N/A |
| 98 | 426.4 (3.20) | 423.4 (3.70) | 424.3 (3.40) | N/A |
| 99 | 410.4 (3.30) | 407.4 (3.90) | 408.4 (3.75) | N/A |
| 100 | 430.3/ 432.3 (3.55) | 427.4/ 429.4 (4.15) | N/A | N/A |
| 102 | 430.3/ 432.3 (3.25) | 427.3/ 429.4 (3.85) | 428.3/ 430.3 (3.60) | N/A |
| 103 | 456.3 (3.25) | 453.4 (3.80) | 454.4 (3.65) | N/A |
| 104 | 414.4 (3.15) | 411.4 (3.75) | 412.3 (3.45) | N/A |
| 105 | 480.4 (3.65) | 477.4 (4.15) | 478.4 (3.75) | N/A |
| 106 | 439.4 (2.80) | 436.3 (3.35) | 437.3 (3.10) | N/A |
| 108 | 453.4 (2.85) | 450.4 (3.40) | 451.4 (3.10) | N/A |
| 109 | 486.5 (2.25) | 483.5 (2.70) | 484.5 (2.50) | N/A |
| 110 | 502.4 (2.30) | N/A | 500.4 (2.50) | N/A |
| 111 | 466.4 (2.45) | 463.4 (2.90) | N/A | N/A |
| 112 | 460.4 (2.25) | 457.4 (2.15) | 458.4 (2.40) | N/A |
| 113 | 460.4 (2.05) | 457.4 (2.45) | 458.4 (2.00) | N/A |
| 114 | 502.4 (2.20) | 499.5 (2.55) | 500.5 (2.15) | N/A |
| 115 | 486.4 (2.05) | 483.5 (2.50) | 484.5 (2.25) | N/A |
| 116 | 447.4 (2.45) | 444.4 (2.80) | 445.4 (2.65) | N/A |
| 118 | 497.4 (2.95) | 494.4 (3.50) | 495.4 (3.20) | N/A |
| 119 | 497.4 (3.15) | 494.4 (3.70) | 495.4 (3.40) | N/A |
| 121 | N/A | N/A | N/A | 406.2 (solvent front) |
| 122 | N/A | N/A | N/A | 350.1 (3.10) |
| 124 | 396.3 (3.05) Known cmpd | 393.3 (3.65) | 394.3 (3.30) | N/A |
| 125 | 402.3 (3.35) | 399.4 (3.90) | 400.4 (3.60) | N/A |
| 126 | 397.3 (2.35) | 394.3 (2.75) | 395.3 (2.50) | N/A |
| 127 | 362.3 (3.15) | 359.3 (3.80) | 360.3 (3.45) | N/A |
| 128 | N/A | 415.3 (3.35) | 416.3 (2.95) | N/A |
| 129 | 376.3 (2.60) | 373.3 (3.25) | 374.3 (2.90) | N/A |
| 130 | 481.4 (3.20) | 478.4 (3.75) | 479.4 (3.45) | N/A |
| 131 | 402.3 (3.35) | 399.4 (4.00) | 400.3 (3.65) | N/A |
| 132 | N/A | N/A | 440.4 (3.40) | N/A |
| Total | 100 | 107 | 114 | 3 |

Total = # of compounds prepared from each benzimidazole-5-carboxylic acid building block Library Subset B1: Biaryls from Suzuki Reaction of Boronic Acids with Benzimidazole Carboxylic Acids Derived from Bromoaniline Benzimidazole-5-Carboxylic Acid Building Blocks

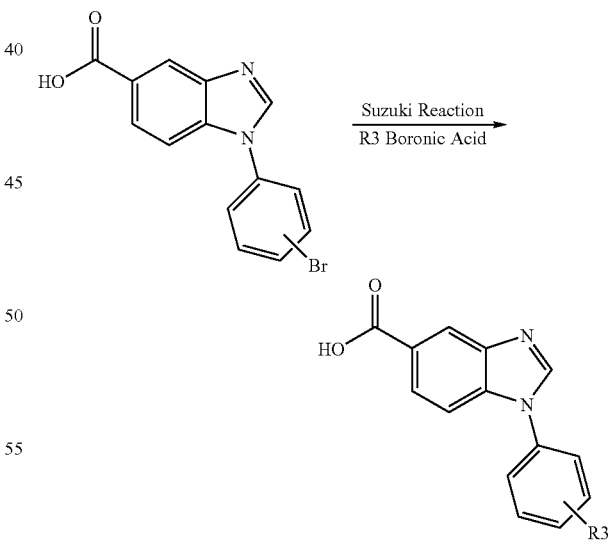

R3 Boronic acids used with 3-bromophenyl benzimidazole-5-carboxylic acid include:

M. Thiophene-3-boronic acid

O. 1-(t-Butoxycarbonyl)-2-pyrrole boronic acid*

P. 4,4,5,5-Tetramethyl-2-(1H-pyrazol-4-yl)-1,3,2-dioxaborolane

Q. 3,5-Dimethylisoxazole-4-boronic acid
R. Pyridine-3-boronic acid

* With 1-(t-Butoxycarbonyl)-2-pyrrole boronic acid, the Boc protecting group on the pyrrole nitrogen was removed during reaction and work-up to give the desired benzimidazole-5-carboxylic acid. The resultant unprotected benzimidazole-5-carboxylic acid building blocks were subsequently loaded onto PS-TFP and used for the process outlined, without further need for protection of the pyrrole N.

R3 Boronic acids used with 4-bromophenyl benzimidazole-5-carboxylic acid include:

N'. Thiophene-2-boronic acid
O'. 1-(t-Butoxycarbonyl)-2-pyrrole boronic acid*
P'. 4,4,5,5-Tetramethyl-2-(1H-pyrazol-4-yl)-1,3,2-dioxaborolane
Q'. 3,5-Dimethylisoxazole-4-boronic acid
R'. Pyridine-3-boronic acid

* With 1-(t-Butoxycarbonyl)-2-pyrrole boronic acid, the Boc protecting group on the pyrrole nitrogen was removed during reaction and work-up to give the desired benzimidazole-5-carboxylic acid. The resultant unprotected benzimidazole-5-carboxylic acid building blocks were subsequently loaded onto PS-TFP and used for the process outlined, without further need for protection of the pyrrole N.

-continued

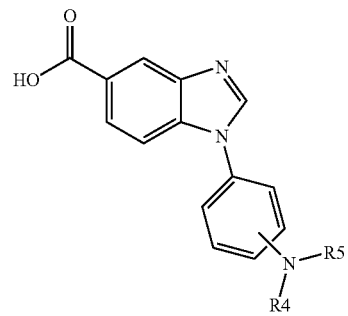

TABLE 3

Tabulated in Table 3 below is a combinatorial library—Subset B1, formed by the process of the present invention. The data is presented in a format $[M + H]^+$ ($R_t$).
Subset B1

| R1R2NH | Benzimidazole Carboxylic acid Building Block derived from reaction of N1-Bromophenyls with R3 boronic acids | | | | |
|---|---|---|---|---|---|
| Amine | M | N' | O* | O'* | P |
| 48 | 391.2 (2.90) | 391.2 (2.80) | 374.3 (2.75) | 374.2 (2.65) | 375.2 (2.45) |
| 121 | 404.2 (3.50) | 404.1 (3.45) | 387.2 (3.45) | 387.2 (solvent front) | 388.2 (2.85) |
| 122 | 348.1 (3.50) | 348.1 (3.45) | 331.2 (3.45) | 331.2 (3.20) | 332.2 (2.85) |
| 123 | 334.1 (3.65) | 334.1 (3.35) | 317.2 (3.20) | 317.1 (3.10) | 318.2 (2.75) |
| Total | 4 | 4 | 4 | 4 | 4 |

| R1R2NH | Benzimidazole Carboxylic acid Building Block derived from reaction of N1-Bromophenyls with R3 boronic acids | | | | |
|---|---|---|---|---|---|
| Amine | P' | Q | Q' | R | R' |
| 48 | 375.2 (2.35) | 404.2 (2.80) | 404.2 (2.60) | 386.2 (2.40) | 386.2 (2.15) |
| 121 | N/A | 417.2 (3.15) | 417.3 (solvent front) | 399.2 (2.70) | 399.2 (2.60) |
| 122 | 332.2 (3.00) | 361.2 (3.20) | 361.2 (3.35) | 343.2 (2.65) | 343.2 (2.60) |
| 123 | 318.2 (2.70) | 347.2 (3.10) | 347.2 (3.10) | 329.2 (2.70) | 329.1 (2.45) |
| Total | 3 | 4 | 4 | 4 | 4 |

Total = # of compounds prepared from each benzimidazole-5-carboxylic acid building block Library Subset C: Aryl Amines from Amination Reactions of R4R5NH Amines Listed with Benzimidazole Carboxylic Acid Derived from Bromoaniline Benzimidazole-5-Carboxylic Acid Building Blocks

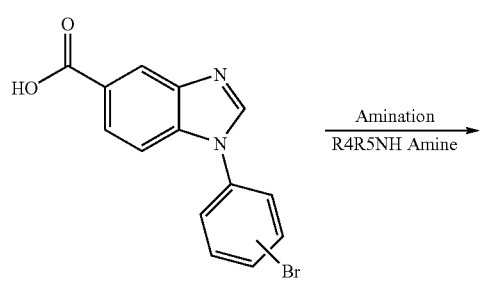

R4R5NH Amines used with 3-bromophenyl benzimidazole-5-carboxylic acid include:

S. Morpholine
U. 3-Chlorobenzylamine—No examples
V. 3-(Aminomethyl)pyridine
W. 2,6-Dimethylaniline—No examples R4R5NH Amines used with 4-bromophenyl benzimidazole-5-carboxylic acid include:

S'. Morpholine
T'. 3-Methylbenzylamine
U'. 3-Chlorobenzylamine—No examples
V'. 3-(Aminomethyl)pyridine
W'. 2,6-Dimethylaniline—No examples

TABLE 4

Tabulated in Table 4 below is a combinatorial library—Subset C, formed by the process of the present invention. The data is presented in a format [M + H]+ ($R_t$).

Subset C

| R1R2NH | Benzimidazole Carboxylic acid Building Block derived from reaction of N1-Bromophenyls with R4R5NH amine | | | | |
|---|---|---|---|---|---|
| Amine | S | S' | T' | V | V' |
| 48 | N/A | 394.3 (solvent front) | 428.3 (3.00) | N/A | 415.1 (2.15) |
| 121 | 407.3 (solvent front) | 407.2 (3.05) | 441.2 (3.65) | 428.2 (2.75) | 428.2 (2.60) |
| 122 | 351.2 (solvent front) | 351.2 (2.85) | 385.2 (3.70) | 372.1 (2.50) | 372.1 (2.40) |
| 123 | 337.2 (solvent front) | 337.2 (2.75) | 371.2 (3.40) | N/A | N/A |
| Total | 3 | 4 | 4 | 2 | 3 |

Total = # of compounds prepared from each benzimidazole-5-carboxylic acid building block Accordingly, the present invention includes a combinatorial library comprising at least three benzimidazoles formed by the reaction:

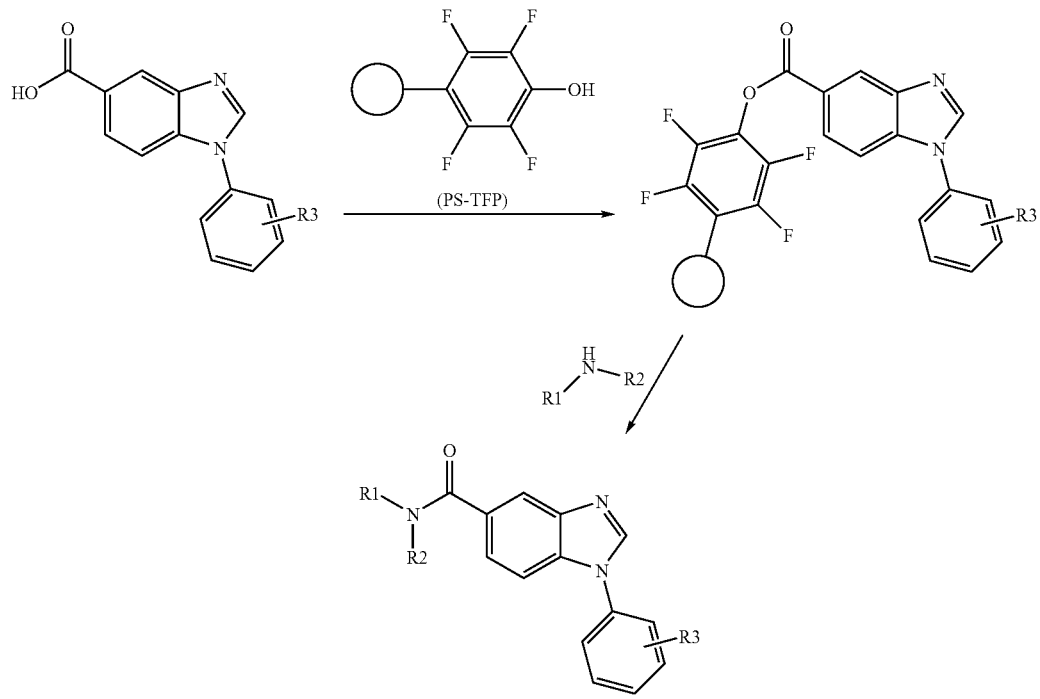

wherein
R1 and R2 are independently
  $C_{0-8}$alkyl optionally substituted with a heterocyclyl substituent,
  $C_{0-8}$alkyl optionally substituted with 1-6 independent halo, —$CONR^{11}R^{12}$, —$NR^{13}CONR^{11}R^{12}$, —$NR^{13}CO_2R^{11}$, —$S(O)_{0-2}$ $NR^{11}R^{12}$, —$NR^{11}S(O)_{0-2}R^{12}$, CN, OH, or optionally substituted aryl substituents;
  —$C_{0-8}$alkyl-$C_{3-8}$cycloalkyl,
  —$C_{0-8}$alkyl-O—$C_{0-8}$alkyl,
  —$C_{0-8}$alkyl-N($C_{0-8}$alkyl)($C_{0-8}$alkyl),
  —$C_{0-8}$alkyl-S(O)$_{0-2}$—$C_{0-8}$alkyl; or heterocyclyl optionally substituted with 1-4 independent $C_{0-8}$alkyl, cyclyl, or substituted cyclyl substituents;

or R1 and R2, taken together with the nitrogen to which they are joined, form a heterocyclic group, optionally substituted with 1-4 independent $C_{0-8}$alkyl, —$C_{0-8}$alkyl-O—$C_{0-8}$alkyl, —$C_{0-8}$alkyl-aryl, or —$C_{0-8}$alkyl-heteroaryl groups;

R3 is an aryl or hetaryl group, optionally substituted with 1-4 independent $C_{0-8}$alkyl, $C_{0-8}$alkyl-cyclyl, halo, OH, —$NR^{31}S(O)_{0-2}R^{32}$, —$S(O)_{0-2}NR^{31}R^{32}$, —$NR^{31}COR^{32}$, —$NR^{31}CONR^{32}R^{33}$, —$CONR^{31}R^{32}$, $S(O)_{0-2}R^{31}$, —O-aryl, —O-hetaryl, $NO_2$, CN, $CF_3$, $OCF_3$, $OCHF_2$;

$R^{11}$, $R^{12}$, $R^{13}$, $R^{31}$, $R^{32}$, and $R^{33}$ are each independently
  $C_{0-8}$alkyl optionally substituted with a heterocyclyl substituent, $C_{0-8}$alkyl optionally substituted with 1-6 independent halo, —CON($C_{0-8}$alkyl)($C_{0-8}$alkyl), —N($C_{0-8}$alkyl) CON($C_{0-8}$alkyl)($C_{0-8}$alkyl), —N($C_{0-8}$alkyl)$CO_2$ ($C_{0-8}$alkyl), $S(O)_{0-2}$N($C_{0-8}$alkyl)($C_{0-8}$alkyl), —$NR^{11}S(O)_{0-2}$($C_{0-8}$alkyl), CN, OH, or optionally substituted aryl substituents;

—$C_{0-8}$alkyl-$C_{3-8}$cycloalkyl,

—$C_{0-8}$alkyl-O—CO8alkyl,

—$C_{0-8}$alkyl-N($C_{0-8}$alkyl)($C_{0-8}$alkyl),

—$C_{0-8}$alkyl-$S(O)_{0-2}$—$C_{0-8}$alkyl; or heterocyclyl optionally substituted with 1-4 independent $C_{0-8}$alkyl, cyclyl, or substituted cyclyl substituents.

The present invention includes a combinatorial library comprising at least three benzimidazoles formed from the reaction of a polymer-supported benzimidazole carboxylic acid with an amine selected from (aminomethyl)cyclopropane; 2-(2-aminoethyl)pyridine; 2-(aminomethyl)pyridine; 4-(2-aminoethyl)morpholine; tetrahydrofurfurylamine; veratrylamine; 1-(2-aminoethyl)-2-imidazolone; 5-amino-2-methoxyphenol; 3-aminobenzyl alcohol; 4-amino-m-cresol; 5-chloro-2-methylbenzylamine; 2-(aminoethyl)-5-methylpyrazine; 3-(2-aminoethyl)pyridine; 4-(trifluoromethyl)piperidine; 3-picolylmethylamine; 1-(3-aminopropyl)imidazole; 1-(3-aminopropyl)-2-pyrrolidinone; isopropylamine; 2-methylbenzylamine; 3-methylbenzylamine; 3-fluorobenzylamine; 4-fluorobenzylamine; N,N-dimethyl-1,3-propanediamine; 4-(3-aminopropyl)morpholine; DL-1-amino-2-propanol; cyclopropylamine; 2-methoxyethylamine; histamine; piperonylamine; 1-phenylpiperazine; 4-piperazinoacetophenone; 1-(2-pyridyl)piperazine; 4-hydroxy-4-phenylpiperidine; 4-acetyl-4-phenylpiperidine; 1-(3-methoxyphenyl)piperazine; 1-(4-methoxyphenyl)piperazine; 1-methylpiperazine; 1-(2-methoxyphenyl)piperazine; 1-(2-hydroxyethyl)piperazine; 1-(2,4-dimethoxyphenyl)piperazine; 1-piperazinepropanol; 1-(2-morpholinoethyl)piperazine; 1-(4-hydroxyphenyl)piperazine; 1-(2-furoyl)piperazine; 1-ethylpiperazine; 1-acetylpiperazine; 2-piperazin-1-yl-1-pyrrolidin-1-ylethanone; N,N-dimethylethylenediamine; 4-benzylpiperidine; 4-cyano-4-phenylpiperidine hydrochloride; 1-(2-dimethylaminoethyl)piperazine; 4-benzyl-4-hydroxypiperidine; 1-(4-pyridyl)piperazine; N-(3-hydroxyphenyl)piperazine; N-(2-hydroxyphenyl)piperazine; 1-(2-cyanophenyl)piperazine; 4-(hydroxymethyl) piperidine; 4-hydroxypiperidine; 4-piperidinopiperidine; 4-(1-pyrrollidino)piperidine; isonipecotamide; piperidine; N,N-diethylnipecotamide; 3-piperidinemethanol; 3-hydroxypiperidine; 4-piperazinoindole; 1-(2-pyrazinyl)piperazine; 4-(aminomethyl)pyridine; 4-(trifluoromethoxy)benzylamine; 4-methoxybenzylamine; 4-chlorobenzylamine; 1-(tetrahydro-2-furoyl)piperazine; 1-(2-(6-methylpyridyl)) piperazine; 1-(4-cyanophenyl)piperazine; 3-chloro-4-methylbenzylamine; pyrrolidine; diethylamine; 4-piperazinoindole; 1,2,3,6-tetrahydropyridine; 2-(2-methylaminoethyl) pyridine; 1-methyl-4-(methylamino)piperidine; 1-(2-Pyrrolidinylmethyl)pyrrolidine; N,N,N'-trimethylethylenediamine; 2,6-dimethylmorpholine; 8-aza-1,4-dioxaspiro [4.5]decane(4-piperidone ethylene ketal); N-(4-aminophenyl)-N-methylacetamide; 2-(4-aminophenyl) ethanol; 3-fluoro-P-anisidine; p-toluidine; 3,4-ethylenedioxyaniline; 1-acetyl-6-aminoindoline; 4-fluoroaniline; 3-fluoro-4-methylaniline; p-anisidine; 3-chloro-4-fluoroaniline; m-anisidine; 3,4-difluoroaniline; 3-methoxybenzylamine; 4-methylbenzylamine; 3-chloro-4-methylaniline; 3-(trifluoromethyl)benzylamine; 2-chlorobenzylamine; 3,5-dimethoxybenzylamine; 2-fluorobenzylamine; 3-(trifluoromethoxy)benzylamine; 4-aminoacetanilide; 3-amino-o-cresol; N1-(4-amino-2-methylphenyl)acetamide; 1-(2-piperidinoethyl)piperazine; 1-morpholin-4-yl-2-piperazin-1-yl-ethanone; 1-(4-pyridylmethyl)piperazine; N,N-dimethyl-2-piperazin-1-yl-acetamide; 1-(3-dimethylaminopropyl)piperazine; 1-(3-morpholinopropyl) piperazine; 1-(3-pyrrolidinopropyl)piperazine; 1-(2-ethoxyethyl)piperazine; 1-pyridin-2-ylmethylpiperazine; (4-fluorophenyl)piperazin-1-ylmethanone; (3-fluorophenyl) piperazin-1-ylmethanone; 2-aminobenzyl alcohol; 4-aminotetrahydropyran; ethylamine; methylamine; benzylamine; cyclohexanemethylamine; 3-(aminomethyl)pyridine; butylamine; 2-piperidineethanol; morpholine; 1-(3-methoxyphenyl)piperazine; n-methylcyclohexylamine; or 2,4-dimethoxyaniline.

The present invention includes a combinatorial library comprising at least three benzimidazoles formed from the Suzuki Reaction of a boronic acid with a N-bromophenyl benzimidazole carboxylic acid:

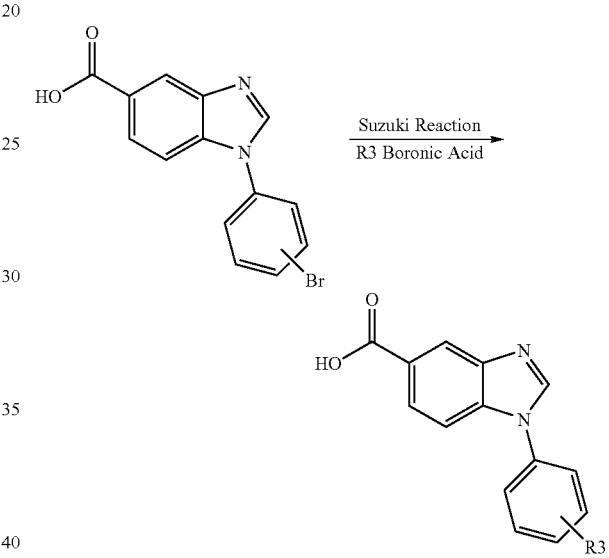

to form an R3 substituted N-phenyl benzimidazole carboxylic acid, wherein R3 is an aryl or hetaryl group, optionally substituted with 1-4 independent $C_{0-8}$alkyl, $C_{0-8}$alkyl-cyclyl, halo, OH, —$NR^{31}S(O)_{0-2}R^{32}$, —$S(O)_{0-2}NR^{31}R^{32}$, —$NR^{31}COR^{32}$, —$NR^{31}CONR^{33}$, —$CONR^{31}R^{32}$, $S(O)_{0-2}R^{31}$, —O-aryl, —O-hetaryl, $NO_2$, CN, $CF_3$, $OCF_3$, $OCHF_2$; $R^{31}$, $R^{32}$, and $R^{33}$ are each independently $C_{0-8}$alkyl optionally substituted with a heterocyclyl substituent, $C_{0-8}$alkyl optionally substituted with 1-6 independent halo, —CON($C_{0-8}$alkyl)($C_{0-8}$alkyl), —N($C_{0-8}$alkyl ) CON($C_{0-8}$alkyl)($C_{0-8}$alkyl), —N($C_{0-8}$alkyl)$CO_2$ ($C_{0-8}$alkyl), $S(O)_{0-2}$N($C_{0-8}$alkyl)($C_{0-8}$alkyl), —$NR^{11}S(O)_{0-2}$($C_{0-8}$alkyl), CN, OH, or optionally substituted aryl substituents;

—$C_{0-8}$alkyl-$C_{3-8}$cycloalkyl,

—$C_{0-8}$alkyl-O—$C_{0-8}$alkyl,

—$C_{0-8}$-alkyl-N($C_{0-8}$alkyl)($C_{0-8}$alkyl),

—$C_{0-8}$-alkyl-$S(O)_{0-2}$—$C_{0-8}$alkyl; or heterocyclyl optionally substituted with 1-4 independent $C_{0-8}$alkyl, cyclyl, or substituted cyclyl substituents;

followed by the reaction of the R3 substituted N-phenyl benzimidazole carboxylic acid with an amine selected from (aminomethyl)cyclopropane; 2-(2-aminoethyl)

pyridine; 2-(aminomethyl)pyridine; 4-(2-aminoethyl)morpholine; tetrahydrofurfurylamine; veratrylamine; 1-(2-aminoethyl)-2-imidazolone; 5-amino-2-methoxyphenol; 3-aminobenzyl alcohol; 4-amino-m-cresol; 5-chloro-2-methylbenzylamine; 2-(aminoethyl)-5-methylpyrazine; 3-(2- aminoethyl)pyridine; 4-(trifluoromethyl)piperidine; 3-picolylmethylamine; 1-(3-aminopropyl)imidazole; 1-(3-aminopropyl)-2-pyrrolidinone; isopropylamine; 2-methylbenzylamine; 3-methylbenzylamine; 3-fluorobenzylamine; 4-fluorobenzylamine; N,N-dimethyl-1,3-propanediamine; 4-(3-aminopropyl)morpholine; DL-1-amino-2-propanol; cyclopropylamine; 2-methoxyethylamine; histamine; piperonylamine; 1-phenylpiperazine; 4-piperazinoacetophenone; 1-(2-pyridyl)piperazine; 4-hydroxy-4-phenylpiperidine; 4-acetyl-4-phenylpiperidine; 1-(3-methoxyphenyl)piperazine; 1-(4-methoxyphenyl)piperazine; 1-methylpiperazine; 1-(2-methoxyphenyl)piperazine; 1-(2-hydroxyethyl)piperazine; 1-(2,4-dimethoxyphenyl)piperazine; 1-piperazinepropanol; 1-(2-morpholinoethyl)piperazine; 1-(4-hydroxyphenyl)piperazine; 1-(2-furoyl)piperazine; 1-ethylpiperazine; 1-acetylpiperazine; 2-piperazin-1-yl-1-pyrrolidin-1-ylethanone; N,N-dimethylethylenediamine; 4-benzylpiperidine; 4-cyano-4-phenylpiperidine hydrochloride; 1-(2-dimethylaminoethyl)piperazine; 4-benzyl-4-hydroxypiperidine; 1-(4-pyridyl)piperazine; N-(3-hydroxyphenyl)piperazine; N-(2-hydroxyphenyl)piperazine; 1-(2-cyanophenyl)piperazine; 4-(hydroxymethyl)piperidine; 4-hydroxypiperidine; 4-piperidinopiperidine; 4-(1-pyrollidino)piperidine; isonipecotamide; piperidine; N,N-diethylnipecotamide; 3-piperidinemethanol; 3-hydroxypiperidine; 4-piperazinoindole; 1-(2-pyrazinyl)piperazine; 4-(aminomethyl)pyridine; 4-(trifluoromethoxy)benzylamine; 4-methoxybenzylamine; 4-chlorobenzylamine; 1-(tetrahydro-2-furoyl)piperazine; 1-(2-(6-methylpyridyl))piperazine; 1-(4-cyanophenyl)piperazine; 3-chloro-4-methylbenzylamine; pyrrolidine; diethylamine; 4-piperazinoindole; 1,2,3,6-tetrahydropyridine; 2-(2-methylaminoethyl)pyridine; 1-methyl-4-(methylamino)piperidine; 1-(2-Pyrrolidinylmethyl)pyrrolidine; N,N,N'-trimethylethylenediamine; 2,6-dimethylmorpholine; 8-aza-1,4-dioxaspiro[4.5]decane(4-piperidone ethylene ketal); N-(4-aminophenyl)-N-methylacetamide; 2-(4-aminophenyl)ethanol; 3-fluoro-P-anisidine; p-toluidine; 3,4-ethylenedioxyaniline; 1-acetyl-6-aminoindoline; 4-fluoroaniline; 3-fluoro-4-methylaniline; p-anisidine; 3-chloro-4-fluoroaniline; m-anisidine; 3,4-difluoroaniline; 3-methoxybenzylamine; 4-methylbenzylamine; 3-chloro-4-methylaniline; 3-(trifluoromethyl)benzylamine; 2-chlorobenzylamine; 3,5-dimethoxybenzylamine; 2-fluorobenzylamine; 3-(trifluoromethoxy)benzylamine; 4-aminoacetanilide; 3-amino-o-cresol; N1-(4-amino-2-methylphenyl)acetamide; 1-(2-piperidinoethyl)piperazine; 1-morpholin-4-yl-2-piperazin-1-yl-ethanone; 1-(4-pyridylmethyl)piperazine; N,N-dimethyl-2-piperazin-1-yl-acetamide; 1-(3-dimethylaminopropyl)piperazine; 1-(3-morpholinopropyl)piperazine; 1-(3-pyrrolidinopropyl)piperazine; 1-(2-ethoxyethyl)piperazine; 1-pyridin-2-ylmethylpiperazine; (4-fluorophenyl)piperazin-1-ylmethanone; (3-fluorophenyl)piperazin-1-ylmethanone; 2-aminobenzyl alcohol; 4-aminotetrahydropyran; ethylamine; methylamine; benzylamine; cyclohexanemethylamine; 3-(aminomethyl)pyridine; butylamine; 2-piperidineethanol; morpholine; 1-(3-methoxyphenyl)piperazine; n-methylcyclohexylamine; or 2,4-dimethoxyaniline.

The boronic acid used in the present invention include thiophene-3-boronic acid; 1-(t-butoxycarbonyl)-2-pyrrole boronic acid; 4,4,5,5-tetramethyl-2-(1H-pyrazol-4-yl)-1,3,2-dioxaborolane; 3,5-dimethylisoxazole-4-boronic acid; pyridine-3-boronic acid; thiophene-2-boronic acid; 1-(t-butoxycarbonyl)-2-pyrrole boronic acid; 4,4,5,5-tetramethyl-2-(1H-pyrazol-4-yl)-1,3,2-dioxaborolane; 3,5-dimethylisoxazole-4-boronic acid; and pyridine-3-boronic acid.

The present invention includes a combinatorial library comprising at least three benzimidazoles formed from the amination of an N-bromophenyl benzimidazole carboxylic acid, thereby replacing the bromine with an amine, wherein the amine includes morpholine, 3-chlorobenzylamine, 3-(aminomethyl)pyridine, and 2,6-dimethylaniline.

What is claimed is:
1. A compound represented by Formula (I)

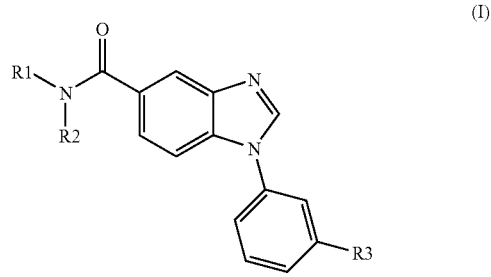

or a pharmaceutically acceptable salt or N-oxide thereof, wherein:
R1 and R2 are independently:
  $C_{0-8}$alkyl optionally substituted with a heterocyclyl group;
  $C_{0-8}$alkyl optionally substituted with 1-6 independent halo, —$CONR^{11}R^{12}$, —$NR^{13}CONR^{11}R^{12}$, —$NR^{13}CO_2R^{11}$, —$S(O)_{0-2}NR^{11}R^{12}$, —$NR^{11}S(O)_{0-2}R^{12}$, CN, OH, or optionally substituted aryl groups;
  —$C_{0-8}$alkyl-$C_{3-8}$cycloalkyl;
  —$C_{0-8}$alkyl-O—$C_{0-8}$alkyl;
  —$C_{0-8}$alkyl-N($C_{0-8}$alkyl)($C_{0-8}$alkyl);
  —$C_{0-8}$alkyl-$S(O)_{0-2}$—$C_{0-8}$alkyl; or
  heterocyclyl optionally substituted with 1-4 independent $C_{0-8}$alkyl, cyclyl, or substituted cyclyl groups;
or R1 and R2, taken together with the nitrogen to which they are joined, form a heterocyclic group optionally substituted with 1-4 independent $C_{0-8}$alkyl, —$C_{0-8}$alkyl-O—$C_{0-8}$alkyl, —$C_{0-8}$alkyl-aryl, or —$C_{0-8}$alkyl-heteroaryl groups, provided that the heterocyclic group formed is not piperazine;
R3 is an aryl or hetaryl group, optionally substituted with 1-4 independent $C_{0-8}$alkyl, $C_{0-8}$alkyl-cyclyl, halo, OH, —$NR^{31}S(O)_{0-2}R^{32}$, —$S(O)_{0-2}NR^{31}R^{32}$, —$NR^{31}COR^{32}$, —$NR^{31}CONR^{32}R^{33}$, —$CONR^{31}R^{32}$, $S(O)_{0-2}R^{31}$, —O-aryl, —O-hetaryl, $NO_2$, CN, $CF_3$, $OCF_3$, or $OCHF_2$ groups; provided that R3 is not a tetrazolyl, 5-pyrimidinyl, or 4-biphenyl;

$R^{11}$, $R^{12}$, $R^{13}$, $R^{31}$, $R^{32}$, and $R^{33}$ are each independently:
  $C_{0-8}$alkyl optionally substituted with a heterocyclyl group;
  $C_{0-8}$alkyl optionally substituted with 1-6 independent halo, —CON($C_{0-8}$alkyl )($C_{0-8}$alkyl), —N($C_{0-8}$alkyl) CON($C_{0-8}$alkyl)($C_{0-8}$alkyl), —N($C_{0-8}$alkyl)CO$_2$ ($C_{0-8}$alkyl), S(O)$_{0-2}$N($C_{0-8}$alkyl)($C_{0-8}$alkyl), —NR$^{11}$S(O)$_{0-2}$($C_{0-8}$alkyl), CN, OH, or optionally substituted aryl groups;
  —$C_{0-8}$alkyl-$C_{3-8}$cycloalkyl;
  —$C_{0-8}$alkyl-O—$C_{0-8}$alkyl;
  —$C_{0-8}$alkyl-N($C_{0-8}$alkyl)($C_{0-8}$alkyl);
  —$C_{0-8}$alkyl-S(O)$_{0-2}$—$C_{0-8}$alkyl; or
  heterocyclyl optionally substituted with 1-4 independent $C_{0-8}$alkyl, cyclyl, or substituted cyclyl groups.

2. The compound according to claim 1, or a pharmaceutically acceptable salt or N-oxide thereof, wherein R3 is aryl that is optionally substituted with 1-4 independent $C_{0-8}$alkyl, $C_{0-8}$alkyl-cyclyl, halo, OH, —NR$^{31}$S(O)$_{0-2}$R$^{32}$, —S(O)$_{0-2}$NR$^{31}$R$^{32}$, —NR$^{31}$COR$^{32}$, —NR$^{31}$CONR$^{32}$R$^{33}$, —CONR$^{31}$R$^{32}$, S(O)$_{0-2}$R$^{31}$, —O-aryl, —O-hetaryl, NO$_2$, CN, CF$_3$, OCF$_3$, or OCHF$_2$ groups.

3. The compound according to claim 2, or a pharmaceutically acceptable salt or N-oxide thereof, wherein R1 is heterocyclyl optionally substituted with 1-4 independent $C_{0-8}$alkyl, cyclyl, or substituted cyclyl groups.

4. The compound according to claim 2, or a pharmaceutically acceptable salt or N-oxide thereof, wherein:
  R1 is $C_{0-8}$alkyl optionally substituted with a heterocyclyl group;
  or R1 is $C_{0-8}$alkyl optionally substituted with 1-6 independent halo, —CONR$^{11}$R$^{12}$, —NR$^{13}$CONR$^{11}$R$^{12}$, —NR$^{13}$CO$_2$R$^{11}$, —S(O)$_{0-2}$NR$^{11}$R$^{12}$, —NR$^{11}$S(O)$_{0-2}$R$^{12}$, CN, OH, or optionally substituted aryl groups.

5. The compound according to claim 2, or a pharmaceutically acceptable salt or N-oxide thereof, wherein R1 is —$C_{0-8}$alkyl-N($C_{0-8}$alkyl)($C_{0-8}$alkyl).

6. The compound according to claim 1, or a pharmaceutically acceptable salt or N-oxide thereof, wherein R3 is hetaryl that is optionally substituted with 1-4 independent $C_{0-8}$alkyl, $C_{0-8}$alkyl-cyclyl, halo, OH, —NR$^{31}$S(O)$_{0-2}$R$^{32}$, —S(O)$_{0-2}$NR$^{31}$R$^{32}$, —NR$^{31}$COR$^{32}$, —NR$^{31}$CONR$^{32}$R$^{33}$, —CONR$^{31}$R$^{32}$, S(O)$_{0-2}$R$^{31}$, —O-aryl, —O-hetaryl, NO$_2$, CN, CF$_3$, OCF$_3$, or OCHF$_2$ groups.

7. The compound according to claim 6, or a pharmaceutically acceptable salt or N-oxide thereof, wherein R1 is heterocyclyl optionally substituted with 1-4 independent $C_{0-8}$alkyl, cyclyl, or substituted cyclyl groups.

8. The compound according to claim 6, or a pharmaceutically acceptable salt or N-oxide thereof, wherein:
  R1 is $C_{0-8}$alkyl optionally substituted with a heterocyclyl group;
  or R1 is $C_{0-8}$alkyl optionally substituted with 1-6 independent halo, —CONR$^{11}$R$^{12}$, —NR$^{13}$CONR$^{11}$R$^{12}$, —NR$^{13}$CO$_2$R$^{11}$, —S(O)$_{0-2}$NR$^{11}$R$^{12}$, —NR$^{11}$S(O)$_{0-2}$R$^{12}$, CN, OH, or optionally substituted aryl groups.

9. The compound according to claim 6, or a pharmaceutically acceptable salt or N-oxide thereof, wherein R1 is —$C_{0-8}$alkyl-N($C_{0-8}$alkyl)($C_{0-8}$alkyl).

10. A compound according to claim 1, which is selected from:
  1-(4'-cyano-1,1'-biphenyl-3-yl)-N-pyridin-3-ylmethyl-1H-benzimidazole-5-carboxamide,
  N-(pyridin-3-ylmethyl)-1-(3-thien-3-ylphenyl)-1H-benzimidazole-5-carboxamide,
  N-(pyridin-3-ylmethyl)-1-[3-(1H-pyrrol-2-yl)phenyl]-1H-benzimidazole-5-carboxamide,
  1-(3'-chloro-4'-fluoro-1,1'-biphenyl-3-yl)-N-(pyridin-3-ylmethyl)-1H-benzimidazole-5-carboxamide,
  1-(3'-cyano-1,1'-biphenyl-3-yl)-N-(pyridin-3-ylmethyl)-1H-benzimidazole-5-carboxamide,
  1-(3'-nitro-1,1'-biphenyl-3-yl)-N-(pyridin-3-ylmethyl)-1H-benzimidazole-5-carboxamide,
  N-(pyridin-3-ylmethyl)-1-(3-pyridin-3-ylphenyl)-1H-benzimidazole-5-carboxamide,
  1-[3-(1-benzyl-1H-pyrazol-4-yl)phenyl]-N-(pyridin-3-ylmethyl)-1H-benzimidazole-5-carboxamide,
  N-(pyridin-3-ylmethyl)-1-[3-(1H-pyrrol-3-yl)phenyl]-1H-benzimidazole-5-carboxamide,
  1-[3-(1-methyl-1H-pyrrol-2-yl)phenyl]-N-(Pyridin-3ylmethyl)-1H-benzimidazole-5-carboxamide,
  1-(2'-nitro-1,1'-biphenyl-3-yl)-N-(pyridin-3-ylmethyl)-1H-benzimidazole-5-carboxamide,
  N-(pyridin-3-ylmethyl)-1-[3-(1,3-thiazol-2-yl)phenyl]-1H-benzimidazole-5-carboxamide,
  N-methyl-1-(3-thien-3-ylphenyl-1H-benzimidazole-5-carboxamide,
  N-methyl-1-[3-(1H-pyrrol-2-yl)phenyl]-1H-benzimidazole-5-carboxamide,
  N-ethyl-1-(3-thien-3-ylphenyl)-1H-benzimidazole-5-carboxamide,
  N-ethyl-1-[3-(1H-pyrrol-2-yl)phenyl]-1H-benzimidazole-5-carboxamide,
  N-methyl-1-(3-pyridin-3-ylphenyl)-1H-benzimidazole-5-carboxamide,
  N-[2-(dimethylamino)ethyl]-1-(3-thien-3-ylphenyl)-1H-benzimidazole-5-carboxamide,
  1-[3'-(acetylamino)-1,1'-biphenyl-3-yl]-N-methyl-1H-benzimidazole-5-carboxamide,
  1-(3'-chloro-4'-fluoro-1,1'-biphenyl-3-yl)-N-methyl-1H-benzimidazole-5-carboxamide,
  1-[3-(1,3-benzodioxol-5-yl)phenyl]-N-methyl-1H-benzimidazole-5-carboxamide,
  1-(1,1'-biphenyl-3-yl)-N-methyl-1H-benzimidazole-5-carboxamide,
  N-methyl-1-(2'-phenoxy-1,1'-biphenyl-3-yl)-1H-benzimidazole-5-carboxamide,
  1-[3-(2,3-dihydro-1-benzofuran-5-yl)phenyl]-N-methyl-1H-benzimidazole-5-carboxamide,
  N-methyl-1-{3'-[(methylsulfonyl)amino]-1,1'-biphenyl-3-yl}-1H-benzimidazole-5-carboxamide,
  1-[3-(5-chlorothien-2-yl)phenyl]-N-methyl-1H-benzimidazole-5-carboxamide,
  N-methyl-1-(3-thien-2-ylphenyl)-1H-benzimidazole-5-carboxamide,
  1-(1,1'-biphenyl-3-yl)-N-methyl-1H-benzimidazole-5-carboxamide,
  N-methyl-1-(4'-methyl-1,1'-biphenyl-3-yl)-1H-benzimidazole-5-carboxamide,
  1-(3'-fluoro-1,1'-biphenyl-3-yl)-N-methyl-1H-benzimidazole-5-carboxamide,
  1-(3-thien-3-ylphenyl)-1H-benzimidazole-5-carboxamide,
  N-(tert-butyl)-1-(3-thien-3-ylphenyl)-1H-benzimidazole-5-carboxamide,
  1-[3-(3,5-dimethylisoxazol-4-yl)phenyl]-N-methyl-1H-benzimidazole-5-carboxamide,
  1-[3-(3,5-dimethylisoxazol-4-yl)phenyl]-N-ethyl-1H-benzimidazole-5-carboxamide,
  N-[2-(dimethylamino)ethyl]-1-[3-(3,5-dimethylisoxazol-4-yl)phenyl]-1H-benzimidazole-5-carboxamide,
  1-[3-(3,5-dimethylisoxazol-4-yl)phenyl]-N-tetrahydro-2H-pyran-4-yl-1H-benzimidazole-5-carboxamide, N-tetrahydro-2H-pyran-4-yl-1-(3-thien-3-ylphenyl)-1H-benzimidazole-5-carboxamide,
N-tetrahydro-2H-pyran-4-yl-1-(3-pyrrol-2-ylphenyl)-1H-benzimidazole-5-carboxamide,
N-methyl-1-[3-(2-naphthyl)phenyl]-1H-benzimidazole-5-carboxamide,
N-methyl-1-[4'-(methylsulfonyl)-1,1'-biphenyl-3-yl]-1H-benzimidazole-5-carboxamide,
1-[3-(1-benzothien-2-yl)phenyl]-N-methyl-1H-benzimidazole-5-carboxamide,
N-[2-(dimethylamino)ethyl]-1-(3-pyrrol-2-ylphenyl)-1H-benzimidazole-5-carboxamide,
N-(pyridin-3-ylmethyl)-1-[3-(1H-pyrrol-1-yl)phenyl]-1H-benzimidazole-5-carboxamide,
N-(1,3-benzodioxol-5-ylmethyl)-1-[3-(1H-pyrrol-1-yl)phenyl]-1H-benzimidazole-5-carboxamide,
or a pharmaceutically acceptable salt or N-oxide thereof.

11. A compound according to claim 1, which is selected from:
1-(4'-cyano-1,1'-biphenyl-3-yl)-N-pyridin-3-ylmethyl-1H-benzimidazole-5-carboxamide,
N-(pyridin-3-ylmethyl)-1-(3-thien-3-ylphenyl)-1H-benzimidazole-5-carboxamide,
1-(3'-chloro-4'-fluoro-1,1'-biphenyl-3-yl)-N-(pyridin-3-ylmethyl)-1H-benzimidazole-5-carboxamide,
1-(3'-cyano-1,1'-biphenyl-3-yl)-N-(pyridin-3-ylmethyl)-1H-benzimidazole-5-carboxamide,
1-(3'-nitro-1,1'-biphenyl-3-yl)-N-(pyridin-3-ylmethyl)-1H-benzimidazole-5-carboxamide,
1-(2'-nitro-1,1'-biphenyl-3-yl)-N-(pyridin-3-ylmethyl)-1H-benzimidazole-5-carboxamide,
or a pharmaceutically acceptable salt or N-oxide thereof.

12. A compound according to claim 1, which is selected from:
1-[3'-(acetylamino)-1,1'-biphenyl-3-yl]-N-methyl-1H-benzimidazole-5-carboxamide,
1-(3'-chloro-4'-fluoro-1,1'-biphenyl-3-yl)-N-methyl-1H-benzimidazole-5-carboxamide,
1-(1,1'-biphenyl-3-yl)-N-methyl-1H-benzimidazole-5-carboxamide,
N-methyl-1-(2'-phenoxy-1,1'-biphenyl-3-yl)-1H-benzimidazole-5-carboxamide,
N-methyl-1-{3'-[(methylsulfonyl)amino]-1,1'-biphenyl-3-yl}-1H-benzimidazole-5- carboxamide,
1-(1,1'-biphenyl-3-yl)-N-methyl-1H-benzimidazole-5-carboxamide,
N-methyl-1-(4'-methyl-1,1'-biphenyl-3-yl)-1H-benzimidazole-5-carboxamide,
1-(3'-fluoro-1,1'-biphenyl-3-yl)-N-methyl-1H-benzimidazole-5-carboxamide,
N-methyl-1-[4'-(methylsulfonyl)-1,1'-biphenyl-3-yl]-1H-benzimidazole-5-carboxamide,
or a pharmaceutically acceptable salt or N-oxide thereof.

13. A compound according to claim 1, which is selected from:
N-(pyridin-3-ylmethyl)-1-(3-(1H-pyrrol-2-yl)phenyl]-1H-benzimidazole-5-carboxamide,
N-(pyridin-3-ylmethyl)-1-(3-pyridin-3-ylphenyl)-1H-benzimidazole-5-carboxamide,
1-[3-(1-benzyl-1H-pyrazol-4-yl)phenyl]-N-(pyridin-3-ylmethyl)-1H-benzimidazole-5-carboxamide,
N-(pyridin-3-ylmethyl)-1-[3-(1H-pyrrol-3-yl)phenyl]-1H-benzimidazole-5-carboxamide,
1-[3-(1-methyl-1H-pyrrol-2-yl)phenyl]-N-(Pyridin-3-ylmethyl)-1H-benzimidazole-5-carboxamide,
N-(pyridin-3-ylmethyl)-1-[3-(1,3-thiazol-2-yl)phenyl]-1H-benzimidazole-5-carboxamide,
1-[3-(3,5-dimethylisoxazol-4-yl)phenyl]-N-tetrahydro-2H-pyran-4-yl-1H-benzimidazole-5-carboxamide,
N-tetrahydro-2H-pyran-4-yl-1-(3-thien-3-ylphenyl)-1H-benzimidazole-5-carboxamide,
N-tetrahydro-2H-pyran-4-yl-1-(3-pyrrol-2-ylphenyl)-1H-benzimidazole-5-carboxamide,
N-(1,3-benzodioxol-5-ylmethyl)-1-[3-(1H-pyrrol-1-yl)phenyl]-1H-benzimidazole-5-carboxamide,
or a pharmaceutically acceptable salt or N-oxide thereof.

14. A compound according to claim 1, which is selected from:
N-methyl-1-(3-thien-3-ylphenyl)-1H-benzimidazole-5-carboxamide,
N-methyl-1-[3-(1H-pyrrol-2-yl)phenyl]-1H-benzimidazole-5-carboxamide,
N-ethyl-1-(3-thien-3-ylphenyl)-1H-benzimidazole-5-carboxamide,
N-ethyl-1-[3-(1H-pyrrol-2-yl)phenyl]-1H-benzimidazole-5-carboxamide,
N-methyl-1-(3-pyridin-3-ylphenyl)-1H-benzimidazole-5-carboxamide,
1-[3-(1,3-benzodioxol-5-yl)phenyl]-N-methyl-1H-benzimidazole-5-carboxamide,
1-[3-(2,3-dihydro-1-benzofuran-5-yl)phenyl]-N-methyl-1H-benzimidazole-5-carboxamide,
1-[3-(5-chlorothien-2-yl)phenyl]-N-methyl-1H-benzimidazole-5-carboxamide,
N-methyl-1-(3-thien-2-ylphenyl)-1H-benzimidazole-5-carboxamide,
1-(3-thien-3-ylphenyl)-1H-benzimidazole-5-carboxamide,
N-(tert-butyl)-1-(3-thien-3-ylphenyl)-1H-benzimidazole-5-carboxamide,
1-[3-(3,5-dimethylisoxazol-4-yl)phenyl]-N-methyl-1H-benzimidazole-5-carboxamide,
1-[3-(3,5-dimethylisoxazol-4-yl)phenyl]-N-ethyl-1H-benzimidazole-5-carboxamide,
N-methyl-1-[3-(2-naphthyl)phenyl]-1H-benzimidazole-5-carboxamide,
1-[3-(1-benzothien-2-yl)phenyl]-N-methyl-1H-benzimidazole-5-carboxamide,
N-(pyridin-3-ylmethyl)-1-[3-(1H-pyrrol-1-yl)phenyl]-1H-benzimidazole-5-carboxamide,
or a pharmaceutically acceptable salt or N-oxide thereof.

15. A compound according to claim 1, which is selected from:
N-[2-(dimethylamino)ethyl]-1-(3-thien-3-ylphenyl)-1H-benzimidazole-5-carboxamide,
N-[2-(dimethylamino)ethyl]-1-[3-(3,5-dimethylisoxazol-4-yl)phenyl]-1H-benzimidazole-5-carboxamide,
N-[2-(dimethylamino)ethyl]-1-(3-pyrrol-2-ylphenyl)-1H-benzimidazole-5-carboxamide,
or a pharmaceutically acceptable salt or N-oxide thereof.

16. A pharmaceutical composition comprising a compound according to claim 1, or a pharmaceutically acceptable salt or N-oxide thereof, and a pharmaceutically acceptable carrier.

* * * * *